(12) United States Patent
Lönn et al.

(10) Patent No.: US 11,680,049 B2
(45) Date of Patent: *Jun. 20, 2023

(54) CERTAIN (2S)-N-[(1S)-1-CYANO-2-PHENYLETHYL]-1,4-OXAZEPANE-2-CARBOXAMIDES AS DIPEPTIDYL PEPTIDASE 1 INHIBITORS

(71) Applicant: AstraZeneca AB, Södertälje (SE)

(72) Inventors: Hans Roland Lönn, Cheshire (GB); Stephen Connolly, Cheshire (GB); Steven Swallow, Cheshire (GB); Staffan Po Karlsson, Mölndal (SE); Carl-Johan Aurell, Mölndal (SE); John Fritiof Pontén, Cheshire (GB); Kevin James Doyle, Essex (GB); Amanda Jane Van De Poël, Essex (GB); Graham Peter Jones, Essex (GB); David Wyn Watson, Essex (GB); Jaqueline Anne Macritchie, Essex (GB); Nicholas John Palmer, Cheshire (GB)

(73) Assignee: AstraZeneca AB, Södertälje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 17/946,024

(22) Filed: Sep. 15, 2022

(65) Prior Publication Data

US 2023/0062646 A1 Mar. 2, 2023

Related U.S. Application Data

(63) Continuation of application No. 17/170,641, filed on Feb. 8, 2021, which is a continuation of application No. 16/855,522, filed on Apr. 22, 2020, now Pat. No. 11,117,874, which is a continuation of application No. 16/358,091, filed on Mar. 19, 2019, now Pat. No. 10,669,245, which is a continuation of application No. 15/708,634, filed on Sep. 19, 2017, now Pat. No. 10,287,258, which is a continuation of application No. 15/346,411, filed on Nov. 8, 2016, now Pat. No. 9,815,805, which is a continuation of application No. 14/601,371, filed on Jan. 21, 2015, now Pat. No. 9,522,894.

(60) Provisional application No. 61/931,090, filed on Jan. 24, 2014.

(51) Int. Cl.

| C07D 267/10 | (2006.01) |
| C07D 409/10 | (2006.01) |
| C07D 413/10 | (2006.01) |
| C07D 413/12 | (2006.01) |
| C07D 413/14 | (2006.01) |
| C07D 417/12 | (2006.01) |
| A61P 11/00 | (2006.01) |
| A61K 31/553 | (2006.01) |
| A61K 45/06 | (2006.01) |

(52) U.S. Cl.
CPC .......... *C07D 267/10* (2013.01); *A61K 31/553* (2013.01); *A61K 45/06* (2013.01); *C07D 413/12* (2013.01); *C07D 413/14* (2013.01); *C07D 417/12* (2013.01)

(58) Field of Classification Search
CPC .. C07D 267/10; C07D 409/10; C07D 413/10; C07D 413/12; C07D 413/14; C07D 417/12; A61P 11/00; A61K 31/553; A61K 45/06

See application file for complete search history.

(56) References Cited

U.S. PATENT DOCUMENTS

| 8,552,034 B2 | 10/2013 | Verwijs et al. |
| 8,871,783 B2 | 10/2014 | Anderskewitz et al. |
| 8,877,775 B2 | 11/2014 | Anderskewitz et al. |
| 8,889,708 B2 | 11/2014 | Grauert et al. |
| 8,987,249 B2 | 3/2015 | Anderskewitz et al. |
| 8,999,975 B2 | 4/2015 | Grundl et al. |
| 9,073,869 B2 | 7/2015 | Anderskewitz et al. |

(Continued)

FOREIGN PATENT DOCUMENTS

| CN | 101945851 A | 1/2011 |
| CN | 102574830 A | 7/2012 |

(Continued)

OTHER PUBLICATIONS

Clinical Trials Identifier: NCT03218917, ClinicalTrials.gov submitted on Aug. 15, 2017, 5 pages.

(Continued)

*Primary Examiner* — Brenda L Coleman
(74) *Attorney, Agent, or Firm* — Cooley LLP

(57) ABSTRACT

The present disclosure relates to certain (2S)—N-[(1S)-1-cyano-2-phenylethyl]-1,4-oxazepane-2-carboxamide compounds (including pharmaceutically acceptable salts thereof), (I)

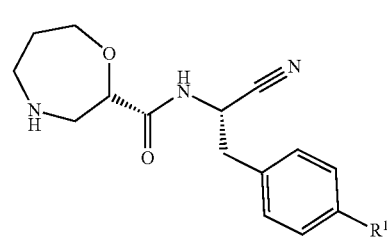

that inhibit dipeptidyl peptidase 1 (DPP1) activity, to their utility in treating and/or preventing clinical conditions including respiratory diseases, such as asthma and chronic obstructive pulmonary disease (COPD), to their use in therapy, to pharmaceutical compositions containing them and to processes for preparing such compounds.

14 Claims, 5 Drawing Sheets

(56) References Cited

U.S. PATENT DOCUMENTS

| | | | |
|---|---|---|---|
| 9,440,960 | B2 | 9/2016 | Grauert et al. |
| 9,522,894 | B2 | 12/2016 | Lonn et al. |
| 9,713,606 | B2 | 7/2017 | Anderskewitz et al. |
| 9,815,805 | B2 | 11/2017 | Lonn et al. |
| 9,856,228 | B2 | 1/2018 | Lauritzen et al. |
| 9,879,026 | B2 | 1/2018 | Vintonyak et al. |
| 10,238,633 | B2 | 3/2019 | Anderskewitz et al. |
| 10,287,258 | B2 | 5/2019 | Lonn et al. |
| RE47,636 | E | 10/2019 | Vintonyak et al. |
| 10,479,781 | B2 | 11/2019 | Lauritzen et al. |
| 10,669,245 | B2 | 6/2020 | Lonn et al. |
| 11,117,874 | B2 | 9/2021 | Lonn et al. |
| 2008/0221093 | A1 | 9/2008 | Gege et al. |
| 2012/0315271 | A1 | 12/2012 | Shelton et al. |
| 2012/0329775 | A1 | 12/2012 | Ford et al. |
| 2014/0275159 | A1 | 9/2014 | Anderskewitz et al. |
| 2015/0025058 | A1 | 1/2015 | Deutsch et al. |
| 2015/0105375 | A1 | 4/2015 | Anderskewitz et al. |
| 2015/0210655 | A1 | 7/2015 | Lonn et al. |
| 2015/0346203 | A1 | 12/2015 | Xu et al. |
| 2016/0061824 | A1 | 3/2016 | Hahn et al. |
| 2017/0057938 | A1 | 3/2017 | Lonn et al. |
| 2018/0028541 | A1 | 2/2018 | Lonn et al. |
| 2018/0044328 | A1 | 2/2018 | Lauritzen et al. |
| 2018/0169017 | A1 | 6/2018 | Desai et al. |
| 2018/0251436 | A1 | 9/2018 | Lonn et al. |
| 2019/0091236 | A1 | 3/2019 | Lonn et al. |
| 2019/0167636 | A1 | 6/2019 | Anderskewitz et al. |
| 2019/0247400 | A1 | 8/2019 | Dipetrillo et al. |
| 2020/0017455 | A1 | 1/2020 | Lonn et al. |
| 2020/0138780 | A1 | 5/2020 | Anderskewitz et al. |
| 2020/0179398 | A1 | 6/2020 | Lonn et al. |
| 2020/0247765 | A1 | 8/2020 | Lonn et al. |
| 2020/0390781 | A1 | 12/2020 | Dipetrillo et al. |
| 2021/0186984 | A1 | 6/2021 | Dipetrillo et al. |
| 2021/0238152 | A1 | 8/2021 | Lonn et al. |
| 2021/0252015 | A1 | 8/2021 | Zhang |
| 2021/0322438 | A1 | 10/2021 | Zhang |
| 2021/0369732 | A1 | 12/2021 | Wikstrom et al. |
| 2022/0133737 | A1 | 5/2022 | Lonn et al. |
| 2023/0025351 | A1 | 1/2023 | Lönn et al. |
| 2023/0028726 | A1 | 1/2023 | Lönn et al. |
| 2023/0033573 | A1 | 2/2023 | Lönn et al. |

FOREIGN PATENT DOCUMENTS

| | | |
|---|---|---|
| EP | 1317555 B1 | 11/2007 |
| EP | 2840083 A1 | 2/2015 |
| JP | 2006527704 A | 12/2006 |
| JP | 2008501692 A | 1/2008 |
| JP | 2008504307 A | 2/2008 |
| JP | 2010540526 A | 12/2010 |
| JP | 2011506421 A | 3/2011 |
| JP | 2011522011 A | 7/2011 |
| JP | 2012522764 A | 9/2012 |
| JP | 2012526093 A | 10/2012 |
| JP | 2016515576 A | 5/2016 |
| JP | 2017503832 A | 2/2017 |
| TW | 201041889 A | 12/2010 |
| WO | WO-9917777 A1 | 4/1999 |
| WO | WO-0116108 A2 | 3/2001 |
| WO | WO-0196285 A1 | 12/2001 |
| WO | WO-02051831 A1 | 7/2002 |
| WO | WO-03048123 A1 | 6/2003 |
| WO | WO-2004076434 A1 | 9/2004 |
| WO | WO-2004087153 A2 | 10/2004 |
| WO | WO-2004106289 A1 | 12/2004 |
| WO | WO-2004110988 A1 | 12/2004 |
| WO | WO-2005106012 A2 | 11/2005 |
| WO | WO-2005107762 A2 | 11/2005 |
| WO | WO-2005120465 A2 | 12/2005 |
| WO | WO-2006000228 A2 | 1/2006 |
| WO | WO-2006020145 A2 | 2/2006 |
| WO | WO-2007005668 A2 | 1/2007 |
| WO | WO-2008109180 A2 | 9/2008 |
| WO | WO-2008109181 A2 | 9/2008 |
| WO | WO-2009026701 A1 | 3/2009 |
| WO | WO-2009042187 A1 | 4/2009 |
| WO | WO-2009074829 A1 | 6/2009 |
| WO | WO-2009147238 A1 | 12/2009 |
| WO | WO-2010077680 A2 | 7/2010 |
| WO | WO-2010114405 A2 | 10/2010 |
| WO | WO-2010128324 A1 | 11/2010 |
| WO | WO-2010142985 A1 | 12/2010 |
| WO | WO-2011154677 A1 | 12/2011 |
| WO | WO-2012064715 A1 | 5/2012 |
| WO | WO-2012119941 A1 | 9/2012 |
| WO | WO-2013041497 A1 | 3/2013 |
| WO | WO-2014091443 A1 | 6/2014 |
| WO | WO-2014140075 A1 | 9/2014 |
| WO | WO-2014140081 A1 | 9/2014 |
| WO | WO-2014140091 A1 | 9/2014 |
| WO | WO-2014151784 A1 | 9/2014 |
| WO | WO-2014165303 A1 | 10/2014 |
| WO | WO-2015032942 A1 | 3/2015 |
| WO | WO-2015032943 A1 | 3/2015 |
| WO | WO-2015032945 A1 | 3/2015 |
| WO | WO-2015110826 A1 | 7/2015 |
| WO | WO-2015175939 A1 | 11/2015 |
| WO | WO-2016075240 A1 | 5/2016 |
| WO | WO-2018022978 A1 | 2/2018 |
| WO | WO-2019157050 A1 | 8/2019 |
| WO | WO-2019166626 A1 | 9/2019 |
| WO | WO-2020018547 A1 | 1/2020 |
| WO | WO-2020018551 A1 | 1/2020 |
| WO | WO-2020247665 A1 | 12/2020 |
| WO | WO-2022140516 A1 | 6/2022 |
| WO | WO-2022232420 A1 | 11/2022 |
| WO | WO-2022232573 A1 | 11/2022 |

OTHER PUBLICATIONS

Clinical Trials Identifier: NCT03218917, ClinicalTrials.gov submitted on Aug. 20, 2018, 17 pages.
Clinical Trials Identifier: NCT03218917, ClinicalTrials.gov submitted on Dec. 11, 2020, 10 pages.
Clinical Trials Identifier: NCT03218917, ClinicalTrials.gov submitted on Dec. 17, 2018, 17 pages.
Clinical Trials Identifier: NCT03218917, ClinicalTrials.gov submitted on Dec. 17, 2019, 10 pages.
Clinical Trials Identifier: NCT03218917, ClinicalTrials.gov submitted on Dec. 4, 2019, 10 pages.
Clinical Trials Identifier: NCT03218917, ClinicalTrials.gov submitted on Dec. 8, 2018, 17 pages.
Clinical Trials Identifier: NCT03218917, ClinicalTrials.gov submitted on Feb. 11, 2019, 17 pages.
Clinical Trials Identifier: NCT03218917, ClinicalTrials.gov submitted on Feb. 12, 2019, 17 pages.
Clinical Trials Identifier: NCT03218917, ClinicalTrials.gov submitted on Feb. 5, 2018, 5 pages.
Clinical Trials Identifier: NCT03218917, ClinicalTrials.gov submitted on Jan. 14, 2019, 17 pages.
Clinical Trials Identifier: NCT03218917, ClinicalTrials.gov submitted on Jan. 28, 2019, 17 pages.
Clinical Trials Identifier: NCT03218917, ClinicalTrials.gov submitted on Jan. 3, 2019, 17 pages.
Clinical Trials Identifier: NCT03218917, ClinicalTrials.gov submitted on Jan. 31, 2019, 17 pages.
Clinical Trials Identifier: NCT03218917, ClinicalTrials.gov submitted on Jul. 12, 2017, 7 pages.
Clinical Trials Identifier: NCT03218917, ClinicalTrials.gov submitted on Jul. 30, 2018, 5 pages.
Clinical Trials Identifier: NCT03218917, ClinicalTrials.gov submitted on Mar. 28, 2019, 16 pages.
Clinical Trials Identifier: NCT03218917, ClinicalTrials.gov submitted on May 28, 2019, 10 pages.
Clinical Trials Identifier: NCT03218917, ClinicalTrials.gov submitted on Nov. 13, 2018, 17 pages.
Clinical Trials Identifier: NCT03218917, ClinicalTrials.gov submitted on Nov. 28, 2018, 17 pages.

(56) References Cited

OTHER PUBLICATIONS

Clinical Trials Identifier: NCT03218917, ClinicalTrials.gov submitted on Nov. 6, 2018, 17 pages.
Clinical Trials Identifier: NCT03218917, ClinicalTrials.gov submitted on Oct. 16, 2018, 17 pages.
Clinical Trials Identifier: NCT03218917, ClinicalTrials.gov submitted on Sep. 12, 2018, 17 pages.
Clinical Trials Identifier: NCT03218917, ClinicalTrials.gov submitted on Sep. 24, 2018, 17 pages.
Clinical Trials Identifier: NCT04594369. ClinicalTrials.gov submitted on Apr. 12, 2022, 33 pages.
Clinical Trials Identifier: NCT04594369. ClinicalTrials.gov submitted on Apr. 22, 2021, 14 pages.
Clinical Trials Identifier: NCT04594369. ClinicalTrials.gov submitted on Apr. 22, 2022, 32 pages.
Clinical Trials Identifier: NCT04594369. ClinicalTrials.gov submitted on Apr. 5, 2022, 32 pages.
Clinical Trials Identifier: NCT04594369. ClinicalTrials.gov submitted on Apr. 9, 2021, 13 pages.
Clinical Trials Identifier: NCT04594369. ClinicalTrials.gov submitted on Aug. 1, 2022, 32 pages.
Clinical Trials Identifier: NCT04594369. ClinicalTrials.gov submitted on Aug. 18, 2022, 32 pages.
Clinical Trials Identifier: NCT04594369. ClinicalTrials.gov submitted on Aug. 23, 2021, 24 pages.
Clinical Trials Identifier: NCT04594369. ClinicalTrials.gov submitted on Aug. 30, 2022, 32 pages.
Clinical Trials Identifier: NCT04594369. ClinicalTrials.gov submitted on Aug. 9, 2021, 23 pages.
Clinical Trials Identifier: NCT04594369. ClinicalTrials.gov submitted on Dec. 1, 2020, 6 pages.
Clinical Trials Identifier: NCT04594369. ClinicalTrials.gov submitted on Dec. 10, 2020, 6 pages.
Clinical Trials Identifier: NCT04594369. ClinicalTrials.gov submitted on Dec. 10, 2021, 28 pages.
Clinical Trials Identifier: NCT04594369. ClinicalTrials.gov submitted on Jul. 11, 2022, 32 pages.
Clinical Trials Identifier: NCT04594369. ClinicalTrials.gov submitted on Jul. 23, 2021, 21 pages.
Clinical Trials Identifier: NCT04594369. ClinicalTrials.gov submitted on Jul. 27, 2022, 32 pages.
Clinical Trials Identifier: NCT04594369. ClinicalTrials.gov submitted on Jul. 9, 2021, 21 pages.
Clinical Trials Identifier: NCT04594369. ClinicalTrials.gov submitted on Jun. 20, 2022, 32 pages.
Clinical Trials Identifier: NCT04594369. ClinicalTrials.gov submitted on Jun. 21, 2021, 19 pages.
Clinical Trials Identifier: NCT04594369. ClinicalTrials.gov submitted on Jun. 24, 2021, 19 pages.
Clinical Trials Identifier: NCT04594369. ClinicalTrials.gov submitted on Jun. 30, 2021, 20 pages.
Clinical Trials Identifier: NCT04594369. ClinicalTrials.gov submitted on Jun. 7, 2021, 19 pages.
Clinical Trials Identifier: NCT04594369. ClinicalTrials.gov submitted on Jun. 7, 2022, 32 pages.
Clinical Trials Identifier: NCT04594369. ClinicalTrials.gov submitted on Mar. 11, 2021, 9 pages.
Clinical Trials Identifier: NCT04594369. ClinicalTrials.gov submitted on May 13, 2022, 33 pages.
Clinical Trials Identifier: NCT04594369. ClinicalTrials.gov submitted on Mar. 25, 2021, 11 pages.
Clinical Trials Identifier: NCT04594369. ClinicalTrials.gov submitted on May 25, 2022, 31 pages.
Clinical Trials Identifier: NCT04594369. ClinicalTrials.gov submitted on Mar. 25, 2022, 34 pages.
Clinical Trials Identifier: NCT04594369. ClinicalTrials.gov submitted on Mar. 4, 2022, 32 pages.
Clinical Trials Identifier: NCT04594369. ClinicalTrials.gov submitted on Nov. 10, 2021, 29 pages.
Clinical Trials Identifier: NCT04594369. ClinicalTrials.gov submitted on Nov. 15, 2022, 30 pages.
Clinical Trials Identifier: NCT04594369. ClinicalTrials.gov submitted on Nov. 19, 2020, 6 pages.
Clinical Trials Identifier: NCT04594369. ClinicalTrials.gov submitted on Nov. 23, 2022, 30 pages.
Clinical Trials Identifier: NCT04594369. ClinicalTrials.gov submitted on Oct. 10, 2022, 31 pages.
Clinical Trials Identifier: NCT04594369. ClinicalTrials.gov submitted on Oct. 14, 2020, 6 pages.
Clinical Trials Identifier: NCT04594369. ClinicalTrials.gov submitted on Oct. 27, 2022, 31 pages.
Clinical Trials Identifier: NCT04594369. ClinicalTrials.gov submitted on Oct. 28, 2021, 29 pages.
Clinical Trials Identifier: NCT04594369. ClinicalTrials.gov submitted on Oct. 29, 202, 29 pages.
Clinical Trials Identifier: NCT04594369. ClinicalTrials.gov submitted on Oct. 8, 2021, 28 pages.
Clinical Trials Identifier: NCT04594369. ClinicalTrials.gov submitted on Sep. 12, 2022, 31 pages.
Clinical Trials Identifier: NCT04594369. ClinicalTrials.gov submitted on Sep. 27, 2022, 31 pages.
Clinical Trials Identifier: NCT04594369. ClinicalTrials.gov submitted on Sep. 7, 2021, 25 pages.
Clinical Trials Identifier: NCT04817332. ClinicalTrials.gov submitted on Aug. 12, 2021, 8 pages.
Clinical Trials Identifier: NCT04817332. ClinicalTrials.gov submitted on Mar. 25, 2021, 8 pages.
Clinical Trials Identifier: NCT05090904. ClinicalTrials.gov submitted on Apr. 14, 2022, 6 pages.
Clinical Trials Identifier: NCT05090904. ClinicalTrials.gov submitted on Apr. 5, 2022, 6 pages.
Clinical Trials Identifier: NCT05090904. ClinicalTrials.gov submitted on Aug. 23, 2022, 7 pages.
Clinical Trials Identifier: NCT05090904. ClinicalTrials.gov submitted on Dec. 3, 2021, 6 pages.
Clinical Trials Identifier: NCT05090904. ClinicalTrials.gov submitted on Jul. 27, 2022, 7 pages.
Clinical Trials Identifier: NCT05090904. ClinicalTrials.gov submitted on Jul. 29, 2022, 7 pages.
Clinical Trials Identifier: NCT05090904. ClinicalTrials.gov submitted on Jul. 4, 2022, 7 pages.
Clinical Trials Identifier: NCT05090904. ClinicalTrials.gov submitted on Jun. 22, 2022, 7 pages.
Clinical Trials Identifier: NCT05090904. ClinicalTrials.gov submitted on Jun. 7, 2022, 7 pages.
Clinical Trials Identifier: NCT05090904. ClinicalTrials.gov submitted on Mar. 8, 2022, 6 pages.
Clinical Trials Identifier: NCT05090904. ClinicalTrials.gov submitted on May 13, 2022, 7 pages.
Clinical Trials Identifier: NCT05090904. ClinicalTrials.gov submitted on May 25, 2022, 7 pages.
Clinical Trials Identifier: NCT05090904. ClinicalTrials.gov submitted on Nov. 10, 2022, 7 pages.
Clinical Trials Identifier: NCT05090904. ClinicalTrials.gov submitted on Oct. 12, 2022, 7 pages.
Clinical Trials Identifier: NCT05090904. ClinicalTrials.gov submitted on Oct. 14, 2021, 5 pages.
Clinical Trials Identifier: NCT05090904. ClinicalTrials.gov submitted on Oct. 29, 2021 ,5 pages.
Clinical Trials Identifier: NCT05090904. ClinicalTrials.gov submitted on Sep. 9, 2022, 7 pages.
Clinical Trials Identifier: NCT05344508. ClinicalTrials.gov submitted on Apr. 18, 2022, 3 pages.
Clinical Trials Identifier: NCT05344508. ClinicalTrials.gov submitted on Aug. 3, 2022, 3 pages.
Clinical Trials Identifier: NCT05344508. ClinicalTrials.gov submitted on Oct. 6, 2022, 3 pages.
Clinical Trials Identifier: NCT05355935. ClinicalTrials.gov submitted on Apr. 26, 2022, 6 pages.
Clinical Trials Identifier: NCT05355935. ClinicalTrials.gov submitted on Aug. 16, 2022, 6 pages.

(56) References Cited

OTHER PUBLICATIONS

Clinical Trials Identifier: NCT05355935. ClinicalTrials.gov submitted on Jul. 27, 2022, 6 pages.
Clinical Trials Identifier: NCT05355935. ClinicalTrials.gov submitted on Jul. 5, 2022, 6 pages.
Clinical Trials Identifier: NCT05355935. ClinicalTrials.gov submitted on Jun. 7, 2022, 6 pages.
Clinical Trials Identifier: NCT05355935. ClinicalTrials.gov submitted on May 16, 2022, 6 pages.
Clinical Trials Identifier: NCT05355935. ClinicalTrials.gov submitted on Oct. 19, 2022, 5 pages.
Clinical Trials Identifier: NCT05355935. ClinicalTrials.gov submitted on Sep. 9, 2022, 6 pages.
Clinical Trials Identifier: NCT05517525. ClinicalTrials.gov submitted on Aug. 24, 2022, 5 pages.
Clinical Trials Identifier: NCT05517525. ClinicalTrials.gov submitted on Nov. 7, 2022, 4 pages.
Clinical Trials Identifier: NCT05517525. ClinicalTrials.gov submitted on Oct. 17, 2022, 4 pages.
Clinical Trials Identifier: NCT05517525. ClinicalTrials.gov submitted on Sep. 21, 2022, 5 pages.
Golchert, D. et al. (Sep. 2013), "Evaluation of some compression aids in tableting of roller compacted swellable core drug layer," Int J Pharm., 453(2):322-328.
Karthik, V. V. (Jun. 2016), "Excipients Used in the Formulation of Tablets," RRJCHEM, 5(2):143-154.
U.S. National Library of Medicine, "Randomized, Double-Blind, Placebo-Controlled, Parallel-Group, Multi-Center Study of Efficacy, Safety & Tolerability, and Pharmacokinetics of INS1007 Administered Daily for 24 Weeks in Non-Cystic Fibrosis Bronchiectasis—The Willow Study," Study NCT03218917 [online], Retrieved from the Internet: https://clinicaltrials.gov/ct2/history/NCT03218917?V_1=View#StudyPageTop, Jul. 2017, 8 pages.
Adkison, A. M. et al. (2002), "Dipeptidyl peptidase I activates neutrophil-derived serine proteases and regulates the development of acute experimental arthritis," J. Clin. Invest. 109(3):363-371.
Alpsoy, E. (Apr. 2005), "Behcet's Disease: Treatment of Mucocutaneous Lesions," Clinical and Experimental Rheumatology, vol. 23, No. 4, pp. 532-539.
Avci, D. (Feb. 2019), "Dipeptidyl Peptidase-4 Inhibitors and Inflammation: Dpp-4 Inhibitors Improve Mean Pleatelet Volume and Gamma Glutamyl Transferase Level," Journal of Biosciences and Medicines, vol. 7, No. 2, pp. 42-53.
Bae, S. et al. (Jul. 2012), "Elevated interleukin-32 expression in granulomatosis with polyangiitis," Rheumatology 2012;51:1979-1988, doi:10.1093/rheumatology/kes163, Advance Access publication.
Birmingham Vasculitis Activity Score (version 3), 1 page [No Date].
Birring, S. S. et al. (2003), "Development of a symptom specific health status measure for patients with chronic cough: Leicester Cough Questionnaire (LCQ)," Thorax; 58:339-343.
Bondebjerg, J. et al. (2005), "Novel semicarbazide-derived inhibitors of human dipeptidyl peptidase I (hDPPI)," Bioorg Med Chem; 13:4408-4424.
Bondejberg, J. et al. (2006), "Dipeptidyl Nitriles as Human Dipeptidyl Peptidase 1 Inhibitors," Bioorg Med Chem Lett;16:3614-3617.
Bragg, R. A. et al. (Sep. 2015), "Aortic Binding of AZD5248: Mechanistic Insight and Reactivity Assays To Support Lead Optimization," Chem Res Toxicol. Oct. 19, 2015;28(10):1991-1999.
Cartin-Ceba, R. et al. (Nov. 2012), "Rituximab for Remission Induction and Maintenance in Refractory Granulomatosis With Polyangiitis (Wegener's)," Arthritis & Rheumatism, vol. 64, No. 11, pp. 3770-3778.
Chalmers, J. D. et al. (2017), "Neutrophil Elastase Activity Is Associated with Exacerbations and Lung Function Decline in Bronchiectasis," Am J Respir Crit Care Med, 195(10):1384-1393.
Chalmers, J. D. et al. (Mar. 2014), "The Bronchiectasis Severity Index. An International Derivation and Validation Study," Am. J. Respir. Crit. Care Med., 189(5):576-585.

Chalmers, J. D. et al. (Nov. 2020), "Phase 2 Trial of the DPP-1 Inhibitor Brensocatib in Bronchiectasis," N Engl J Med ;383(22):2127-2137.
Dadoniene, J. et al. (2017), "Clinical characteristics and long-term survival differences of the ANCA-associated vasculitis group: a cross-sectional study of 27 patients," ACTA Medica Lituanica, vol. 24, No. 2, pp. 107-112.
Doyle, K. et al. (Oct. 2016), "Discovery of second generation reversible covalent DPP1 inhibitors leading to an Oxazepane Amidoacetonitrile based clinical candidate (AZD7986)," Journal of Medicinal Chemistry, 59(20):9457-9472.
Everts-Graber, J. et al. (2019), "Proteomic analysis of neutrophils in ANCA-associated vasculitis reveals a dysregulation in proteinase 3-associated proteins such as annexin-A1 involved in apoptotic cell clearance," Kidney International 96, 397-408; https://doi.org/10.1016/j.kint.2019.02.017.
Extended European Search Report for European Application No. 17195612.1, dated Mar. 21, 2018, 5 pages.
Extended European Search Report for European Application No. 17835331.4, dated Feb. 11, 2020, 8 pages.
Extended European Search Report for European Application No. 19751012.6, dated Oct. 4, 2021, 7 pages.
Extended European Search Report for European Application No. 19837016.5, dated Mar. 18, 2022, 10 pages.
Extended European Search Report for European Application No. 19838400.0, dated Mar. 24, 2022, 9 pages.
Extended European Search Report for European Application No. 20173862.2, dated Sep. 11, 2020, 7 pages.
Falk, R. J. et al. (Jun. 1990) "Anti-neutrophil cytoplasmic autoantibodies induce neutrophils to degranulate and produce oxygen radicals in vitro," Proc. Natl. Acad. Sci. USA, vol. 87, pp. 4115-4119.
Floris, A. et al. (Apr. 2016), "Using the Birmingham vasculitis activity score as a screening tool in patients with suspected vasculitis," i174, Poster Viewing III, Retrieved from the Internet: URL: https://academic.oup.com/rheumatology/article-abstract/55/suppl_1/i174/1795586, Retrieved from the Internet on Apr. 23, 2018, 1 page.
Furber, M. et al. (2014), "Cathepsin C Inhibitors: Property Optimization and Identification of a Clinical Candidate," Journal of Medicinal Chemistry, vol. 57, pp. 2357-2367.
Gardiner, P. et al. (2016), "Neutrophil maturation rate determines the effects of dipeptidyl peptidase 1 inhibition on neutrophil serine protease activity," Br J Pharmacol; 173:2390-401.
Geetha, D. et al. (2015), "Current therapy of granulomatosis with polyangiitis and microscopic polyangiitis: the role of rituximab," J Nephrol 28:17-27.
Goeminne, P. C. et al. (Feb. 2014), "Mortality in non-cystic fibrosis bronchiectasis: A prospective cohort analysis," Respir. Med., 108(2):287-296.
Guarino, C. et al. (2017), "Prolonged pharmacological inhibition of cathepsin C results in elimination of neutrophil serine proteases," Biochem Pharmacol; 131:52-67.
Guay, D. et al. (2009), "Design and synthesis of dipeptidyl nitriles as potent, selective, and reversible inhibitors of cathepsin C," Bioorg Med Chem Lett; 19:5392-5396.
Guay, D. et al. (2010), "Therapeutic Utility and Medicinal chemistry of Cathepsin C Inhibitors," Curr Top Med Chem; 10:708-716.
Guillevin, L. et al. (Mar. 1999), "Microscopic Polyangiitis," Arthritis & Rheumatism, vol. 42, No. 3, pp. 421-430.
Insmed, (Feb. 2020), "Insmed Announces Positive Top-Line Results from Phase 2 Willow Study ofINS1007 in Patients with Non-Cystic Fibrosis Bronchiectasis," 5 page.
International Search Report and Written Opinion for International Application No. PCT/EP2019/055138, dated Jul. 19, 2019, 11 pages.
International Search Report and Written Opinion for International Application No. PCT/GB2015/050155, dated Mar. 6, 2015, 7 pages.
International Search Report and Written Opinion for International Application No. PCT/US2017/044343, dated Oct. 12, 2017, 7 pages.
International Search Report and Written Opinion for International Application No. PCT/US2019/016844, dated May 31, 2019, 10 pages.

(56) References Cited

OTHER PUBLICATIONS

International Search Report and Written Opinion for International Application No. PCT/US2019/042021, dated Sep. 4, 2019, 7 pages.
International Search Report and Written Opinion for International Application No. PCT/US2019/042026, dated Sep. 4, 2019, 7 pages.
International Search Report and Written Opinion for International Application No. PCT/US2021/064810, dated Mar. 16, 2022, 8 pages.
International Search Report and Written Opinion for International Application No. PCT/US2022/026769, dated Sep. 9, 2022, 15 pages.
International Search Report and Written Opinion for International Application No. PCT/US2022/027026, dated Sep. 14, 2022, 11 pages.
Invitation to Pay Additional Fees for International Application No. PCT/US2022/026769, mailed Jun. 27, 2022, 3 pages.
Invitation to Pay Additional Fees for International Application No. PCT/US2022/027026, mailed Jul. 8, 2022, 2 pages.
Jarrot, P-A et al. (Jul. 2016), "Review Pathogenesis of ANCA-associated vasculitis: An update," Autoimmunity Reviews, vol. 15, Issue 7, pp. 704-713.
Jenne, D. E. (Aug. 1990), "Wegener's autoantigen decoded," Nature, vol. 346, p. 520.
Jennette, J. C. (2011), "Nomenclature and classification of vasculitis: lessons learned from granulomatosis with polyangiitis (Wegener's granulomatosis)," Clinical and Experimental Immunology, 164 (Suppl. 1), pp. 7-10.
Jones, B. E. et al. (2017), "Gene-Specific DNA Methylation Changes Predict Remission in Patients with ANCA-Associated Vasculitis," J Am Soc Nephrol 28: 1175-1187. doi: 10.1681/ASN.2016050548.
Kallenberg, C. G. M. et al. (Dec. 2006), "Mechanisms of Disease: pathogenesis and treatment of ANCA-associated vasculitides," Nature Clinical Practice Rheumatology, vol. 2, No. 12, pp. 661-670.
Kelly, M. G. et al. (Sep. 2003), "Bronchiectasis in secondary care: A comprehensive profile of a neglected disease," Eur. J. Intern. Med., 14(8):488-492.
Keogh, K. A. et al. (2006), "Rituximab for Refractory Wegener's Granulomatosis. Report of a Prospective, Open-Label Pilot Trial," Am J Respir Crit Care Med vol. 173. pp. 180-187.
Kettritz, R. (Jun. 2008), "Autoimmunity in kidney diseases," The Scandinavian Journal of Clinical & Laboratory Investigation, vol. 68, No. S241, 99-103.
Knopf, A. et al. (2015), "Clinical aspects of granulomatosis with polyangiitis affecting the head and neck," Eur Arch Otorhinolaryngol 272:185-193.
Kono, H., et al. (Oct. 2012), "The IL-1-dependent sterile inflammatory response has a substantial caspase-1-independent component that requires cathepsin C," The Journal of Immunology, vol. 189, No. 7, pp. 3734-3740.
Korkmaz, B. et al. (2013), "Neutrophil proteinase 3 and dipeptidyl peptidase I (cathepsin C)as pharmacological targets in granulomatosis with polyangiitis (Wegener granulomatosis)," Semin Immunopathol, 35:411-421.
Korkmaz, B. et al. (2018) "Therapeutic targeting of cathepsin C: from pathophysiology to treatment," Pharmacol Ther; 190:202-236.
Korkmaz, B. et al. (2019), "Structure-based design and in vivo anti-arthritic activity evaluation of a potent dipeptidyl cyclopropyl nitrile inhibitor of cathepsin C," Biochem Pharmacol ;164:349-367.
Korkmaz, B. et al. (2020), "Lung Protection by Cathepsin C Inhibition: A New Hope for COVID-19 and ARDS?" J Med Chem ;63:13258-13265. doi:10.1021/acs.jmedchem.0c00776.
Korkmaz, B. et al. (Nov. 2010), "Neutrophil Elastase, Proteinase 3, and Cathepsin G as Therapeutic Targets in Human Diseases," Pharmacological Reviews, vol. 62, No. 4, pp. 726-759.
Laine, D. I. et al. (2010), "Discovery of novel cyanamide-based inhibitors of cathepsin C," ACS Med Chem Lett.;2(2):142-147.
Laine, D. I. et al. (2010), "Inhibitors of Cathepsin C (DPPI)," Expert Rev. Ther Pat; 20: 497-506.
Lins, L. et al. (2016), "SF-36 total score as a single measure of health-related quality of life: Scoping review," SAGE Open Medicine, vol. 4:1-12.
Luqmani, R. A. et al. (1994), "Birmingham Vasculitis Activity Score (BVAS) in Systemic Necrotizing Vasculitis," Q. J. Med; 87:671-678.
McShane, P. J. et al. (2013), "Non-cystic fibrosis bronchiectasis," Am J Respir Crit Care Med; 188(6):647-656. doi: 10.1164/rccm.201303-0411Cl.
Methot, N. et al. (2008), "In Vivo Inhibition of Serine Protease Processing Requires a High Fractional Inhibition of Cathepsin C," Mol. Pharm; 73(6):1857-1865.
Methot, N. et al. (Jul. 2007), "Inhibition of the activation of multiple serine proteases with a cathepsin C inhibitor requires sustained exposure to prevent proenzyme processing," J. Biol. Chem., 282(29):20836-20846.
Miller, B. E. et al. (2017), "Epithelial desquamation observed in a Phase I study of an oral cathepsin C inhibitor (GSK2793660)," Br J Clin Pharmacol;83(12):2813-2820. doi:10.1111/bcp.13398.
Miller, M. R. et al. (2005), "Standardisation of spirometry," Eur. Respir. J; 26:319-338.
Mukhtyar, C. et al. (2009), "Modification and validation of the Birmingham Vasculitis Activity Score (version 3)," Ann Rheum Dis;68:1827-1832.
Murray, M. P. et al. (2009), "Sputum colour: a useful clinical tool in non-cystic fibrosis bronchiectasis," Eur Respir J; 34: 361-364.
Murray, M. P. et al. (2009), "Validation of the Leicester Cough Questionnaire in non-cystic fibrosis bronchiectasis," Eur Respir J; 34: 125-131.
Pagnoux, C. et al. (2015), "Treatment of granulomatosis with polyangiitis (Wegener's)," Expert Review of Clinical Immunology, 11:3, 339-348.
Pagnoux, C. et al. (2016), "Optimal therapy and prospects for new medicines in eosinophilic granulomatosis with polyangiitis (Churg-Strauss syndrome)," Expert Review of Clinical Immunology, vol. 12, No. 10, pp. 1059-1067.
Palmer, R. et al. (2018), "Dipeptidyl Peptidase 1 Inhibitor AZD7986 Induces a Sustained, Exposure-Dependent Reduction in Neutrophil Elastase Activity in Healthy Subjects," Clin Pharmacol Ther; 104(6):1155-1164. doi:10.1002/cpt.1053.
Pham, C. T. (Jul. 2006), "Neutrophil serine proteases: specific regulators of inflammation," Nat. Rev. Immunol;6:541-550.
Popa, E. R. et al. (1999), "Differential B- and T-cell activation in Wegener's granulomatosis," J Allergy Clin Immunol ;103:885-894.
Pubchem, CID 134527801, "(2S)-2-[[Hydroxy-[(2S)-1,4-oxazepan-2-yl]methyl]amino]-3-[4-(3-methyl-2-oxo-1,3-benzoxazol-5-yl)phenyl]propanenitrile," Jun. 23, 2018, Retrieved from the Internet: URL: https://pubchem.ncbi.nlm.nih.gov/compound/134527801, 6 pages.
Rawn, S. et al. (2014), "Purpura, petechiae, and bullae as first signs of juvenile granulomatosis with polyangiitis," Eur J Pediatr 173:1685-1689.
Rehm, S. R. T. et al. (2019), "Premedication with a cathepsin C inhibitor alleviates early primary graft dysfunction in mouse recipients after lung transplantation," Sci Rep;9(1):9925-9933.
Schirmer, J. H. et al. (2016), "Clinical presentation and long-term outcome of 144 patients with microscopic polyangiitis in a monocentric German cohort," Rheumatology ;55:71-79.
Schreiber, A. et al. (Mar. 2012), "Neutrophil serine proteases promote IL-1β generation and injury in necrotizing crescentic glomerulonephritis," Journal of the American Society of Nephrology, vol. 23, No. 3, pp. 470-482.
Selga, D. et al. (2006), "Polyarteritis nodosa when applying the Chapel Hill nomenclaturea descriptive study on ten patients," Rheumatology;45:1276-1281.
Shapiro, S. C. et al. (2016), "Inflammatory bowel disease mimicking granulomatosis with polyangiitis: a case report," Journal of Medical Case Reports 10:214, 5 pages.
Stenton, C., (2008), "The MRC breathlessness scale," Occupational Medicine; 58:226-227.
Stockley, R. et al., (Feb. 2013), "Phase II study of a neutrophil elastase inhibitor (AZD9668) in patients with bronchiectasis," Respiratory Medicine, vol. 107, No. 4, pp. 524-533.

(56) References Cited

OTHER PUBLICATIONS

Stone, J. H. et al., (Apr. 2001), "A Disease-Specific Activity Index for Wegener's Granulomatosis," Arthritis & Rheumatism, vol. 44, No. 4, pp. 912-920.

Suka, M. et al. (2012), "Improvement in health-related quality of life in MPO-ANCA-associated vasculitis patients treated with cyclophosphamide plus prednisolone: an analysis of 18 months of follow-up data from the JMAAV study," Mod Rheumatol 22:877-884.

Sunamoto et al. (1984), "Unexpected Tissue Distribution of Liposomes Coated With Amylopectin Derivatives And Successful Use In The Treatment Of Experimental Legionnaires' Diseases," Receptor-Mediated Targeting of Drugs, vol. 82, pp. 359-371 (G. Gregoriadis et al. eds.).

Trouvin, A.-P. et al. (2014), "Usefulness of monitoring of B cell depletion in rituximab-treated rheumatoid arthritis patients in order to predict clinical relapse: a prospective observational study," Clinical and Experimental Immunology, vol. 180, pp. 11-18.

Von Vietinghoff, S. et al., (2005), "Membrane proteinase 3 and Wegener's granulomatosis," Clinical Nephrology, vol. 64, No. 4, pp. 453-459.

Wickremasinghe, M. et al. (2005), "Non-tuberculous mycobacteria in patients with bronchiectasis," Thorax, 60(12):1045-1051.

Yates, M. et al. (2016), "EULAR/ERA-EDTA recommendations for the management of ANCA-associated vasculitis," Ann Rheum Dis 75:1583-1594.

Zhang, J. et al. (2019), "INS1007, a Reversible Dipeptidyl Peptidase 1 Inhibitor, Ameliorates Interferon-alpha-Accelerated Lupus Nephritis in Mice," Abstract Review, 17th International Congress of Immunology. Abstract: A-1059-0027-00953, 1 page.

Zhang, J. et al. (2019), "The Reversible Dipeptidyl Peptidase 1 Inhibitor, INS1007, Decreases Surface Proteinase 3 Expression and Neutrophil Serine Protease Activities in Human Neutrophils," Rheumatology. 58(Supplement 2), p. ii24.

CERTAIN (2S)-N-[(1S)-1-CYANO-2-PHENYLETHYL]-1,4-OXAZEPANE-2-CARBOXAMIDES AS DIPEPTIDYL PEPTIDASE 1 INHIBITORS

RELATED APPLICATIONS

This application is a continuation of U.S. application Ser. No. 17/170,641, filed Feb. 8, 2021, which is a continuation of U.S. application Ser. No. 16/855,522, filed Apr. 22, 2020, now U.S. Pat. No. 11,117,874, which is a continuation of U.S. application Ser. No. 16/358,091, filed Mar. 19, 2019, now U.S. Pat. No. 10,669,245, which is a continuation of U.S. application Ser. No. 15/708,634, filed Sep. 19, 2017, now U.S. Pat. No. 10,287,258, which is a continuation of U.S. application Ser. No. 15/346,411, filed Nov. 8, 2016, now U.S. Pat. No. 9,815,805, which is a continuation of U.S. application Ser. No. 14/601,371, filed Jan. 21, 2015, now U.S. Pat. No. 9,522,894, which claims the benefit of priority under 35 U.S.C. § 119(e) of U.S. Provisional Patent Application No. 61/931,090, filed Jan. 24, 2014. The contents of the foregoing application are hereby incorporated by reference in their entirety.

TECHNICAL FIELD

The technical field relates to certain (2S)—N-[(1S)-1-cyano-2-phenylethyl]-1,4-oxazepane-2-carboxamide compounds (including pharmaceutically acceptable salts thereof) that inhibit dipeptidyl peptidase 1 (DPP1; EC 3.4.14.1) activity, to their utility in treating and/or preventing clinical conditions including respiratory diseases, such as asthma and chronic obstructive pulmonary disease (COPD), to their use in therapy, to pharmaceutical compositions containing them and to processes for preparing such compounds.

BACKGROUND

Dipeptidyl peptidase 1 (DPP1; EC 3.4.14.1), also known as cathepsin C, is a lysosomal cysteine protease belonging to the papain family having a molecular weight of 200 kDa. DPP1 was first discovered by Gutman and Fruton in 1948 (*J Biol Chem*, 174, 851-858); however, the cDNA of the human enzyme was first described in 1995 (Paris et al. 1995, *FEBS Lett*, 369, 326-330). DPP1 is the only member of the papain family that is functional as a tetramer, consisting of four identical subunits. Each subunit is composed of an N-terminal fragment, a heavy chain and a light chain (Dolenc et al. 1995, *J Biol Chem*, 270, 21626-21631).

DPP1 is constitutively expressed in many tissues with highest levels in lung, kidney, liver and spleen. DPP1 catalyses the removal of dipeptides from the N-terminal end of polypeptide substrates with broad specificity. Recent data suggest that besides being an important enzyme in lysosomal protein degradation, DPP1 also functions as a key enzyme in the activation of granule serine proteases in cytotoxic T lymphocytes and natural killer cells (granzymes A and B), mast cells (chymase and tryptase) and neutrophils (cathepsin G, neutrophil elastase and proteinase-3).

Mast cells are found in many tissues but are present in greater numbers along the epithelial linings of the body, such as the skin, respiratory tract and gastrointestinal tract. In humans, two types of mast cells have been identified. The T-type, which expresses only tryptase, and the MC-type, which expresses both tryptase and chymase. In humans, the T-type mast cells are located primarily in alveolar tissue and intestinal mucosa while the TC-type cells predominate in skin and conjunctiva. Tryptase and chymase appear to be important mediators of allergic diseases, being involved in processes of inflammation, bronchoconstriction and mucus secretion.

Neutrophils play a critical role in host defence against invading pathogens. Neutrophils are produced in the bone marrow and are fully mature when released into the circulation to take up their role as the first line of cellular defence. Pro-inflammatory mediators and chemotactic attractants activate neutrophils and draw them to the site of infection, where they act to engulf bacteria by phagocytosis, assaulting them with an arsenal of anti-bacterial compounds that use both oxidative and non-oxidative methods of attack. The powerful serine protease, neutrophil elastase, is one of those anti-bacterial compounds that are clearly involved in destroying bacteria. Neutrophil elastase is released into the phagolysome surrounding the microorganism, which it proceeds to destroy. Neutrophil elastase is able to attack the outer membrane protein, OmpA, in gram-negative bacteria, helping to directly kill the pathogen by degrading its membrane, as well as enabling other anti-bacterial compounds to gain access to the pathogen. In addition, neutrophil elastase may help process other anti-bacterial compounds, converting them from inactive pro-peptides into their active states, such as for cathelicidin.

Yet neutrophil elastase can also cause problems for its host. It is one of the most destructive enzymes in the body, with the capability of degrading extracellular matrix proteins (including collagens, proteoglycan, fibronectin, platelet receptors, complement receptor, thrombomodulin, lung surfactant and cadherins) and key plasma proteins (including coagulation and complement factors, immunoglobulin, several proteases and protease inhibitors). Under physiological conditions, endogenous protease inhibitors, such as α1-antitrypsin, tightly regulate the activity of neutrophil elastase. However, at inflammatory sites, neutrophil elastase is able to evade regulation, and once unregulated it can induce the release of pro-inflammatory cytokines, such as interleukin-6 and interleukin-8, leading to acute lung injury. It can even impair host defence against infection by degrading phagocyte surface receptors and opsonins. Its negative role is illustrated by its involvement in the tissue destruction and inflammation that characterise numerous diseases, including hereditary emphysema, chronic obstructive pulmonary disease, cystic fibrosis, adult respiratory distress syndrome, ischemic-reperfusion injury and rheumatoid arthritis.

There is strong evidence associating tryptase and chymase with a number of mast cell mediated allergic, immunological and inflammatory diseases. The fact that neutrophil elastase, cathepsin G and proteinase 3 also seem to play significant roles in these types of diseases point to DPP1 being a valid therapeutic target due to its central role in activating these proteases (Adkison et al. 2002, *J Clin Invest*, 109, 363-271; Pham et al. 2004, *J Immunol*, 173, 7277-7281).

WO2004/110988 relate to certain nitrile derivatives and their use as DPP1 inhibitors.
WO2009/074829 relate to peptidyl nitriles and their use as DPP1 inhibitors.
WO2010/128324 relate to α-amino amide nitriles and their use as DPP1 inhibitors.
WO2012/119941 relate to peptidyl nitrile compounds and their use as DPP1 inhibitors.
WO2013/041497 relate to N-[1-cyano-2-(phenyl)ethyl]-2-azabicyclo[2.2.1]heptane-3-carboxamide and their use as DPP1 inhibitors.

WO2001/096285 and WO2003/048123 relate to β-amino amide nitriles that have an inhibitory activity on cysteine proteases.

There is no disclosure of an amide nitrile compound which bears a β-amino acid in the form of the disclosed (2S)—N-[(1S)-1-cyano-2-phenylethyl]-1,4-oxazepane-2-carboxamide compounds. We have now found that such compounds possess potent DPP1 activity and/or have desirable pharmacological activity profiles (for example a decreased risk of binding to elastin rich tissues, such as the aorta).

SUMMARY

There are provided compounds that are inhibitors of dipeptidyl peptidase 1 (DPP1), their use as medicaments, pharmaceutical compositions containing them and synthetic routes to their production.

According to a first aspect, there is provided a compound of formula (I),

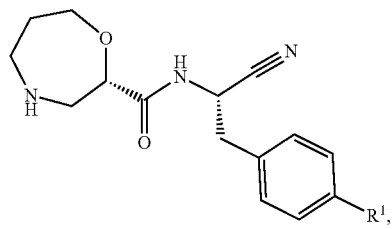

(I)

wherein
$R^1$ is

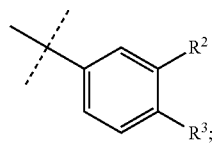

$R^2$ is selected from hydrogen, F, Cl, Br, $OSO_2C_{1-3}$alkyl or $C_{1-3}$alkyl;
$R^3$ is selected from hydrogen, F, Cl, Br, CN, $CF_3$, $SO_2C_{1-3}$alkyl, $CONH_2$ or $SO_2NR^4R^5$, wherein $R^4$ and $R^5$ together with the nitrogen atom to which they are attached form a azetidine, pyrrolidine or piperidine ring; or
$R^1$ is selected from

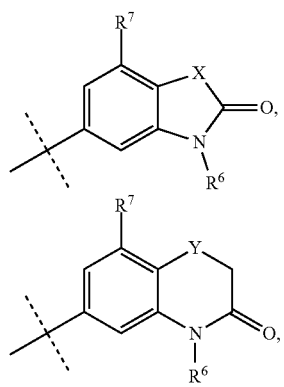

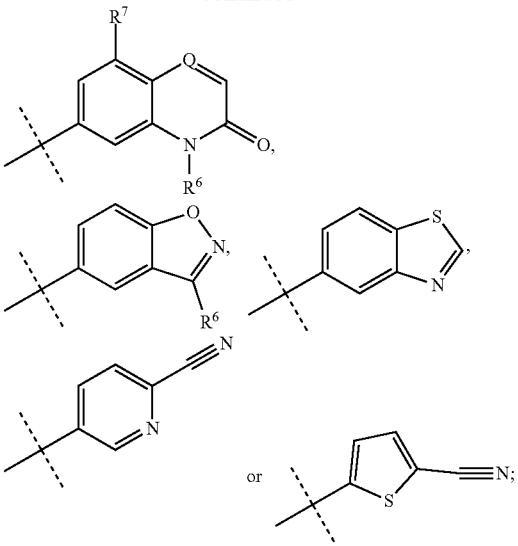

X is selected from O, S or $CF_2$;
Y is selected from O or S;
Q is selected from CH or N;
$R^6$ is selected from $C_{1-3}$alkyl, wherein said $C_{1-3}$alkyl is optionally substituted by 1, 2 or 3 F and optionally by one substituent selected from OH, $OC_{1-3}$alkyl, $N(C_{1-3}alkyl)_2$, cyclopropyl, or tetrapydropyran;
$R^7$ is selected from hydrogen, F, Cl or $CH_3$;
or a pharmaceutically-acceptable salt thereof.

The compounds disclosed are inhibitors of DPP1. Thus, the disclosed compounds can be used as a medicament, in particular for disorders, disease or conditions responsive to inhibition of DPP1, and more specifically respiratory diseases (such as COPD and asthma).

In another aspect, there is provided a compound of formula (I), or a pharmaceutically acceptable salt of a compound of formula (I), wherein the stereochemistry is undefined, e.g. a racemate or a mixture of diastereomers.

In another aspect, there is provided a pharmaceutical formulation comprising a therapeutically effective amount of a compound of formula (I), or a pharmaceutically acceptable salt of a compound of formula (I), and a pharmaceutically acceptable diluent, excipient and/or inert carrier.

In a further embodiment, there is provided a pharmaceutical formulation comprising a compound of formula (I), or a pharmaceutically acceptable salt of a compound of formula (I), for use in the treatment of a condition where inhibition of dipeptidyl peptidase 1 (DPP1) would be beneficial.

In a further embodiment, there is provided a compound of formula (I), or a pharmaceutically acceptable salt of a compound of formula (I), for use in therapy, especially in the prevention or treatment of respiratory disease in a mammal, particularly a human.

In a further embodiment, there is provided a compound of formula (I), or a pharmaceutically acceptable salt of a compound of formula (I), for use in therapy, especially in the prevention or treatment of asthma in a mammal, particularly a human.

In a further embodiment, there is provided a compound of formula (I), or a pharmaceutically acceptable salt of a compound of formula (I), for use in therapy, especially in the prevention or treatment of COPD in a mammal, particularly a human.

In a further embodiment, there is provided the use of a compound of formula (I), or a pharmaceutically acceptable salt of a compound of formula (I), for the manufacture of a medicament for the treatment and prevention of respiratory disease.

In a further embodiment, there is provided the use of a compound of formula (I), or a pharmaceutically acceptable salt of a compound of formula (I), for the manufacture of a medicament for the treatment and prevention of asthma.

In a further embodiment, there is provided the use of a compound of formula (I), or a pharmaceutically acceptable salt of a compound of formula (I), for the manufacture of a medicament for the treatment and prevention of COPD.

In still a further embodiment, administration of a compound of formula (I), or a pharmaceutically acceptable salt of a compound of formula (I) results in reduction in levels of DPP1 in a mammal, particularly a human.

In still a further embodiment, administration of a compound of formula (I), or a pharmaceutically acceptable salt of a compound of formula (I), results in reduction in levels of DPP1, neutrophil elastase, cathepsin G and proteinase-3 in a mammal, particularly a human.

In still a further embodiment, administration of a compound of formula (I), or a pharmaceutically acceptable salt of a compound of formula (I), results in a reduction of DPP1 activity in a mammal, particularly a human.

In still a further embodiment, administration of a compound of formula (I), or a pharmaceutically acceptable salt of a compound of formula (I), results in a reduction of DPP1 activity, neutrophil elastase activity, cathepsin G activity and proteinase-3 activity in a mammal, particularly a human.

According to another aspect, there is provided a process for the preparation of compounds of formula (I), or pharmaceutically acceptable salts of compounds of formula (I), and the intermediates used in the preparation thereof.

According to another aspect, there is provided a compound of formula (XXIV),

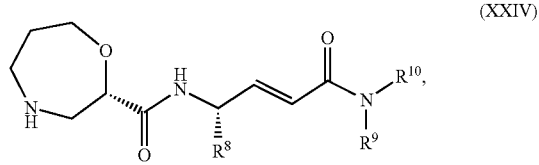

(XXIV)

wherein
$R^8$ is selected from $C_{1-4}$ alkyl or aryl, wherein said aryl is optionally substituted by $R^1$;
$R^9$ and $R^{10}$ taken together with the nitrogen to which they are attached represent a 5- to 7-membered saturated or unsaturated ring optionally containing one other heteroatom which is oxygen, nitrogen or sulfur, wherein said ring is optionally fused to a $(C_3-C_8)$cycloalkyl, heterocycloalkyl, aryl or heteroaryl ring;
or $R^9$ and $R^{10}$ taken together with the nitrogen to which they are attached represent a 6- to 10-membered bridged bicyclic ring optionally fused to a $(C_3-C_8)$cycloalkyl, heterocycloalkyl, aryl or heteroaryl ring;
or a pharmaceutically-acceptable salt thereof.

In still a further embodiment, there is provided a compound of formula (XXIV), or a pharmaceutically acceptable salt of a compound of formula (XXIV), for use in therapy, especially in the prevention or treatment of respiratory disease in a mammal, particularly a human.

The compounds of formula (I) herein exemplified have an $IC_{50}$ of less than 100 nmol/L for DPP1 in enzyme activity assays, for example Test A1 or Test A2 described below. The compounds of formula (I) also display a promising pharmacological profiles by separating desired and undesired effects in vivo.

DETAILED DESCRIPTION

Figure 1:
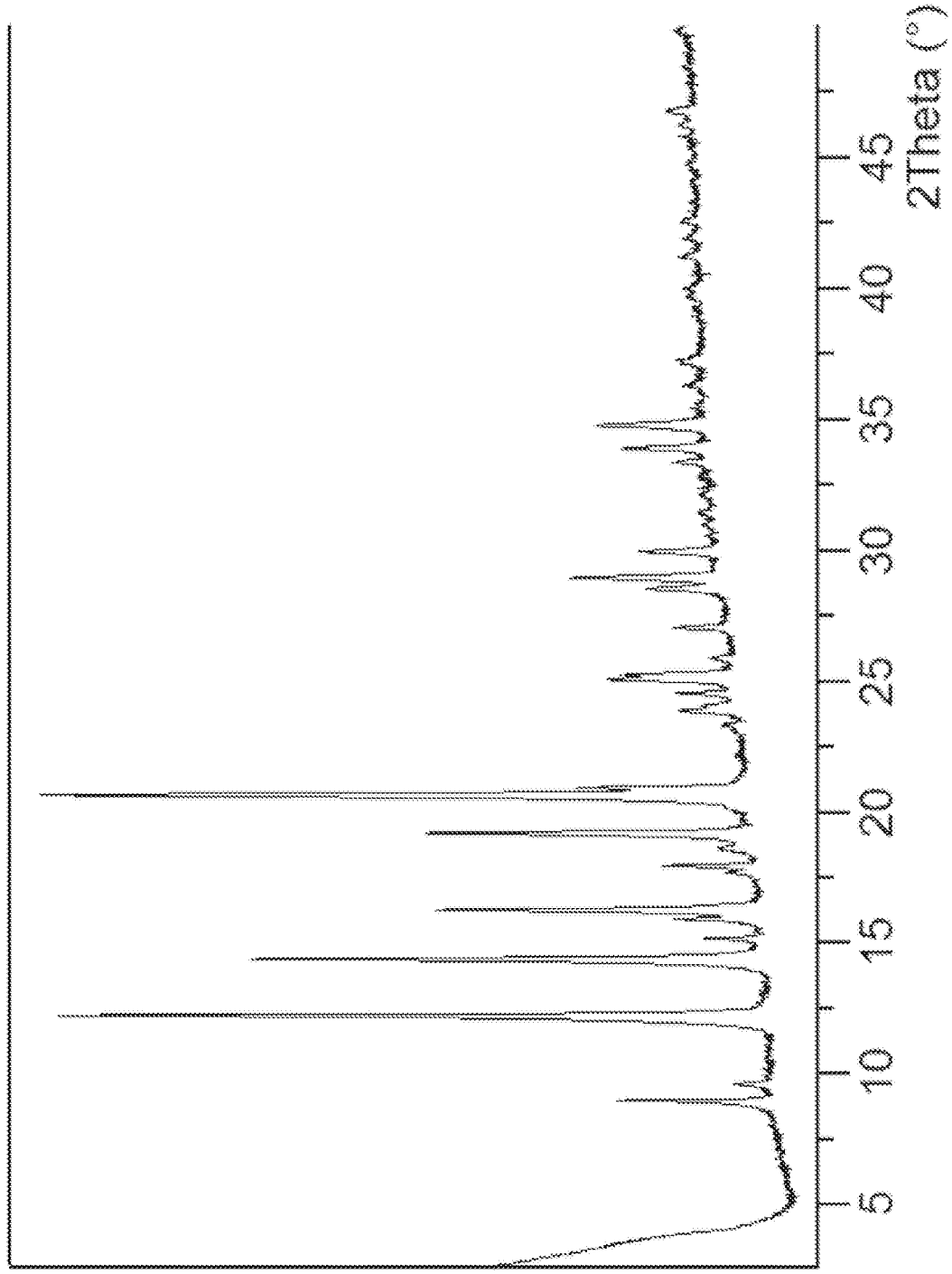
FIG. 1 shows the X-ray powder diffraction pattern for Example 2: (2S)—N-{(1S)-1-Cyano-2-[4-(3-methyl-2-oxo-2,3-dihydro-1,3-benzoxazol-5-yl)phenyl]ethyl}-1,4-oxazepane-2-carboxamide, Form A.
Figure 2:
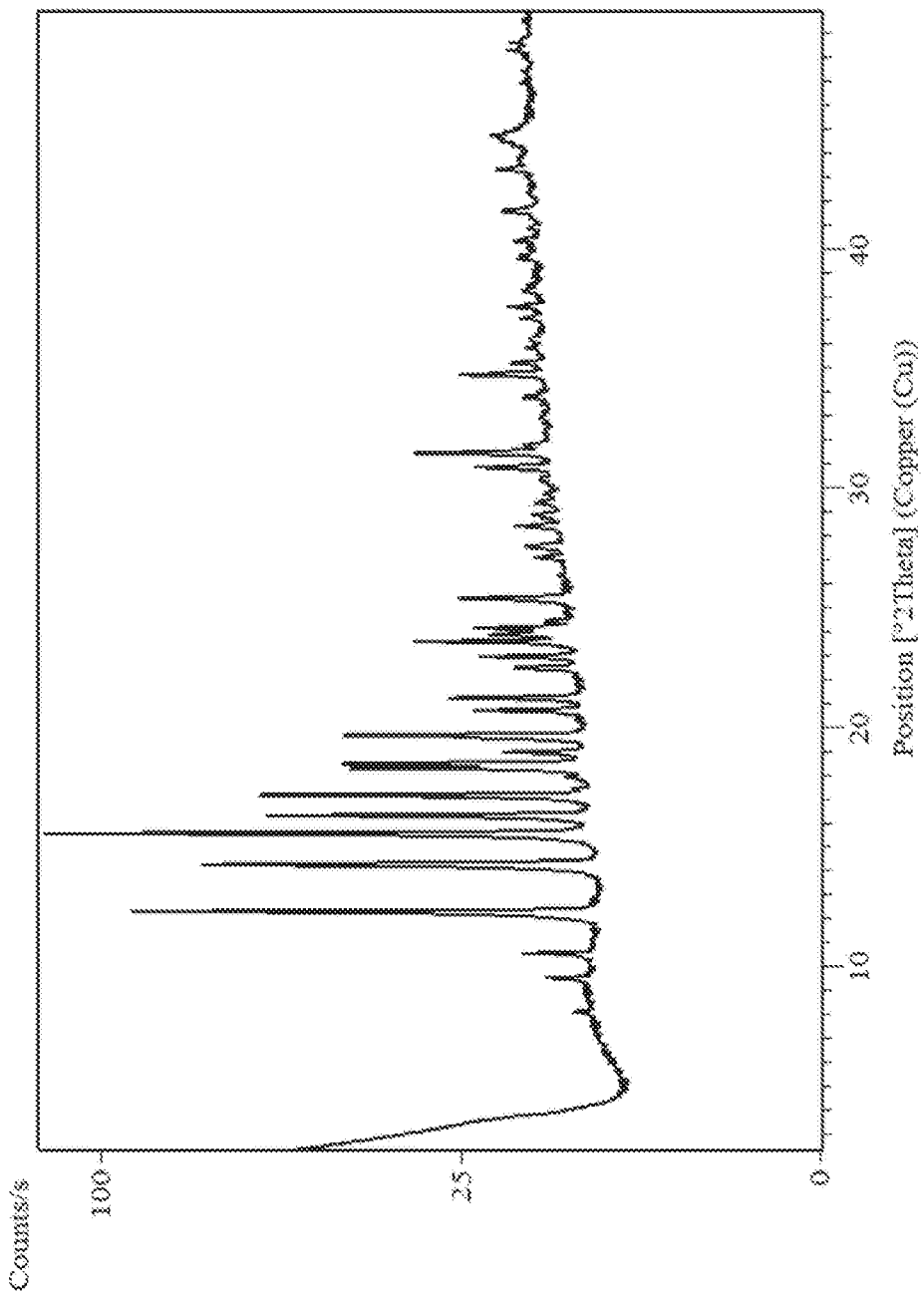
FIG. 2 shows the X-ray powder diffraction pattern for Example 2: (2S)—N-{(1S)-1-Cyano-2-[4-(3-methyl-2-oxo-2,3-dihydro-1,3-benzoxazol-5-yl)phenyl]ethyl}-1,4-oxazepane-2-carboxamide, Form B.
Figure 3:
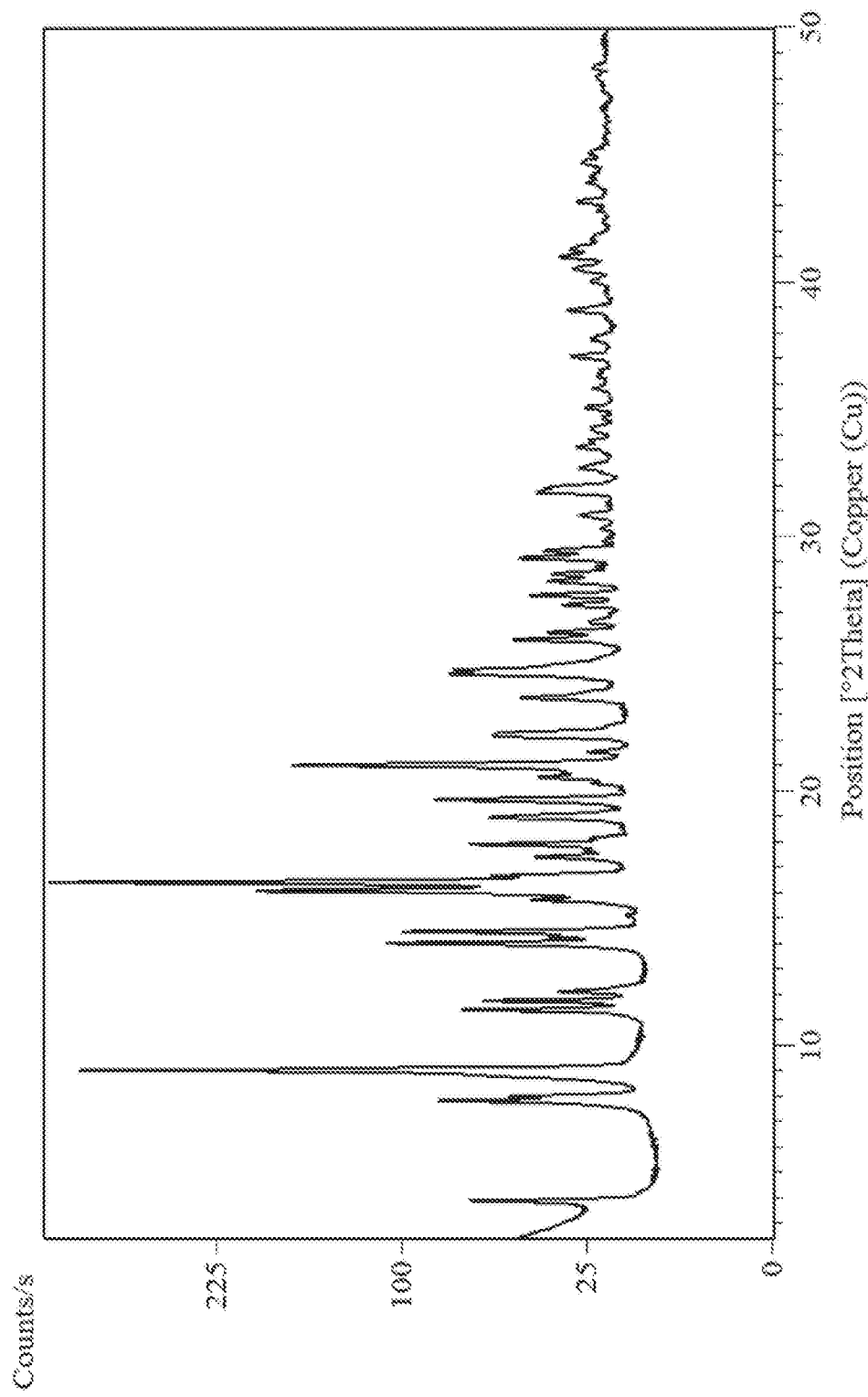
FIG. 3 shows the X-ray powder diffraction pattern for Example 2: (2S)—N-{(1S)-1-Cyano-2-[4-(3-methyl-2-oxo-2,3-dihydro-1,3-benzoxazol-5-yl)phenyl]ethyl}-1,4-oxazepane-2-carboxamide, Form C.
Figure 4:
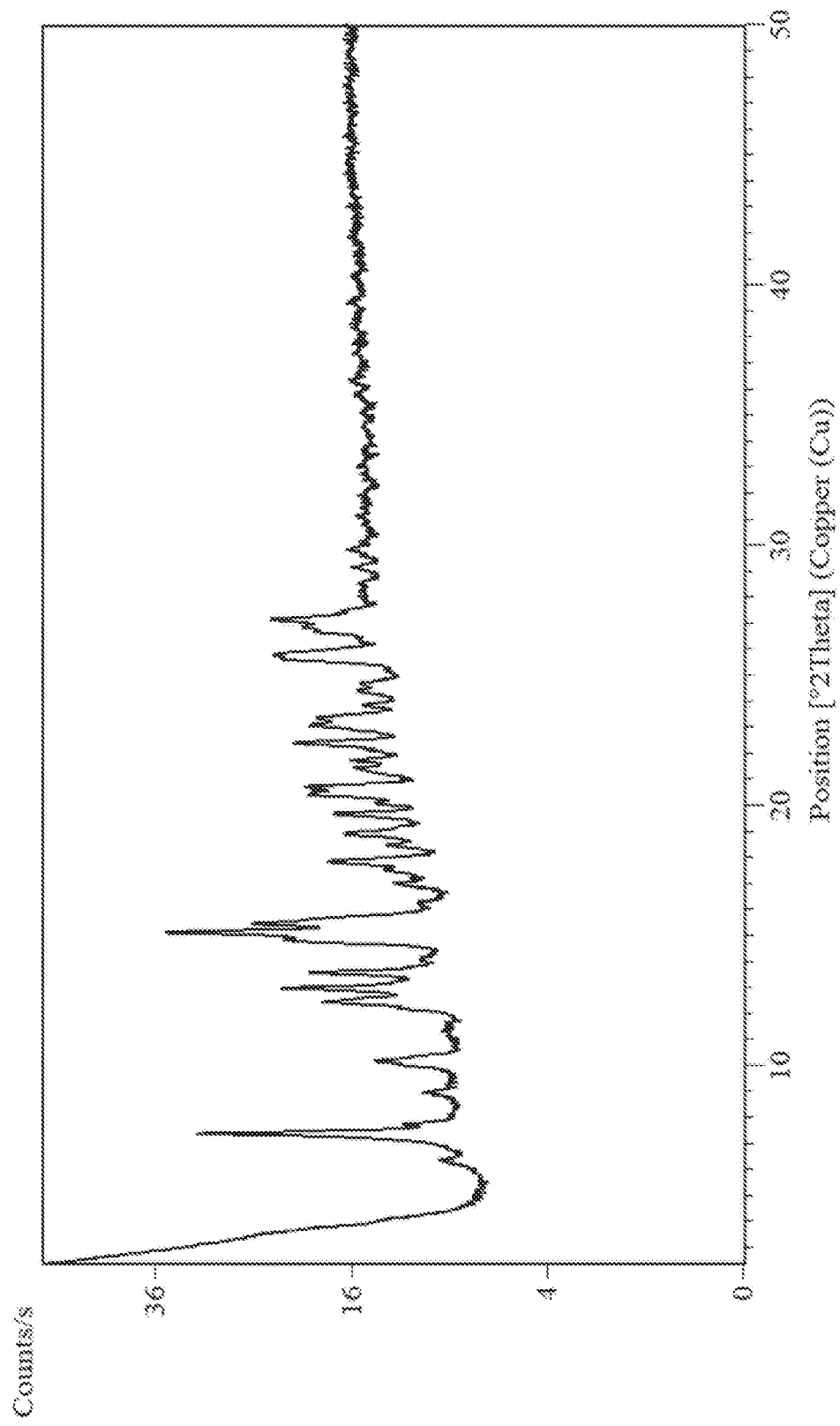
FIG. 4 shows the X-ray powder diffraction pattern for Example 2: (2S)—N-{(1S)-1-Cyano-2-[4-(3-methyl-2-oxo-2,3-dihydro-1,3-benzoxazol-5-yl)phenyl]ethyl}-1,4-oxazepane-2-carboxamide, xinafoate salt, Form A.
Figure 5:
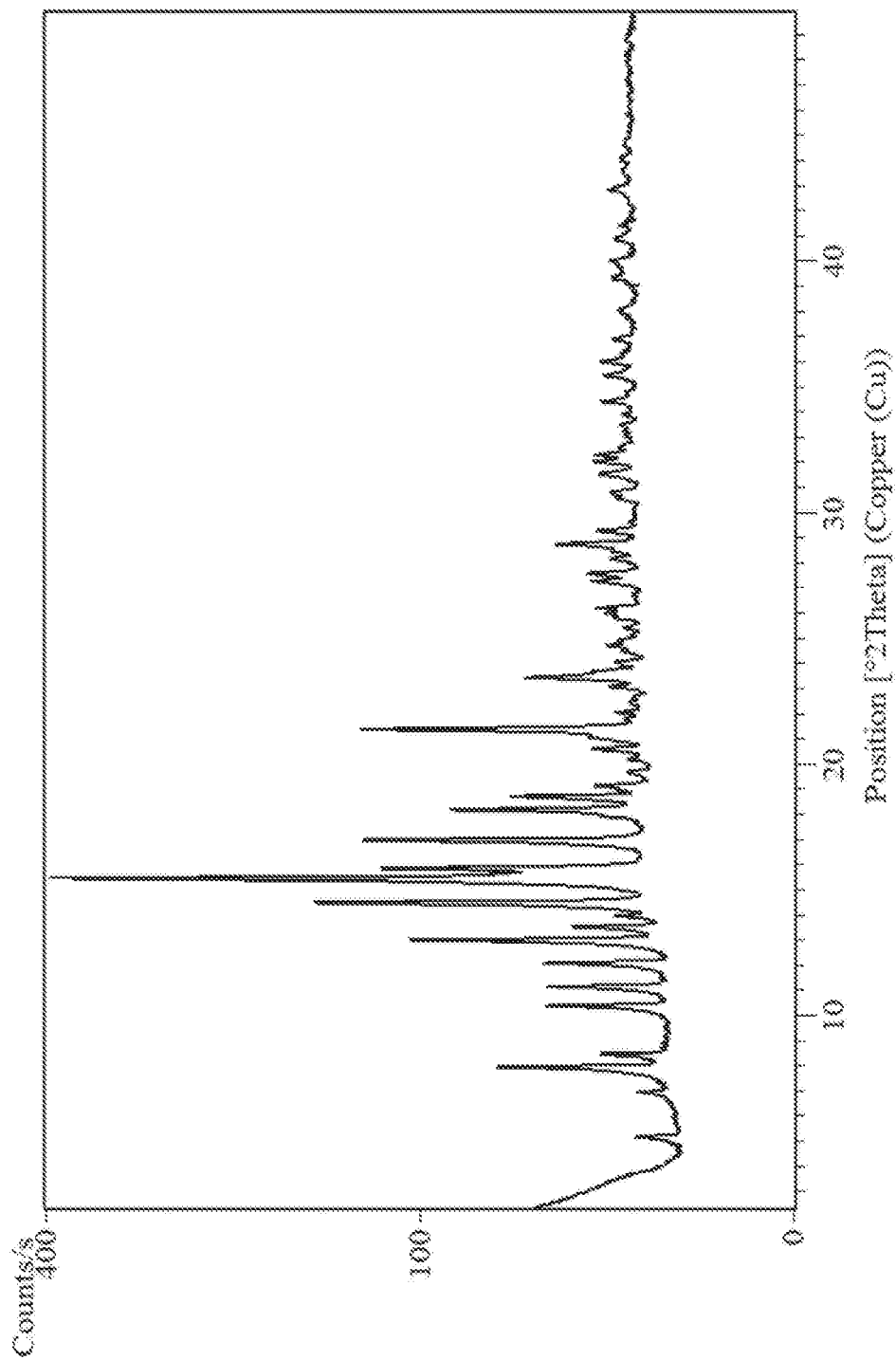
FIG. 5 shows the X-ray powder diffraction pattern for Example 2: (2S)—N-{(1S)-1-Cyano-2-5 [4-(3-methyl-2-oxo-2,3-dihydro-1,3-benzoxazol-5-yl)phenyl]ethyl}-1,4-oxazepane-2-carboxamide, R-mandalate salt, Form A.

This detailed description is intended to acquaint others skilled in the art with the disclosure, its principles, and its practical application so that others skilled in the art may readily apply the disclosures. This description and its specific examples, while indicating embodiments of the disclosures, are intended for purposes of illustration only. Therefore, the disclosure is not limited to the illustrative embodiments described in this specification. In addition, it is to be appreciated that various features of the disclosure that are, for clarity reasons, described in the context of separate embodiments, also may be combined to form a single embodiment. Conversely, various features of the disclosure that are, for brevity reasons, described in the context of a single embodiment, also may be combined to form subcombinations thereof.

Listed below are definitions of various terms used in the specification and claims to describe the present disclosure.

For the avoidance of doubt it is to be understood that where in this specification a group is qualified by "defined above" the said group encompasses the first occurring and broadest definition as well as each and all of the other definitions for that group.

For the avoidance of doubt it is to be understood that in this specification "$C_{1-3}$" means a carbon group having 1, 2 or 3 carbon atoms.

In this specification, unless stated otherwise, the term "alkyl" includes both straight and branched chain alkyl groups and may be, but is not limited to, methyl, ethyl, n-propyl or i-propyl.

In this specification, unless stated otherwise, the term "pharmaceutically acceptable" is used to characterize a moiety (e.g. a salt, dosage form, or excipient) as being appropriate for use in accordance with sound medical judgment. In general, a pharmaceutically acceptable moiety has one or more benefits that outweigh any deleterious effect that the moiety may have. Deleterious effects may include, for example, excessive toxicity, irritation, allergic response, and other problems and complications.

There are disclosed compounds of formula (I) wherein $R^1$-$R^7$, X, Y and Q are as defined in formula (I).

In one embodiment $R^1$ is

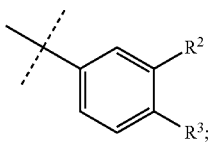

$R^2$ is selected from hydrogen, F, Cl, Br, $OSO_2C_{1-3}$alkyl, or $C_{1-3}$alkyl;
$R^3$ is selected from hydrogen, F, Cl, Br, CN, $CF_3$, $SO_2C_{1-3}$alkyl, $CONH_2$ or $SO_2NR^4R^5$,
wherein $R^4$ and $R^5$ together with the nitrogen atom to which they are attached form a azetidine, pyrrolidine or piperidine ring.

In a further embodiment $R^1$ is

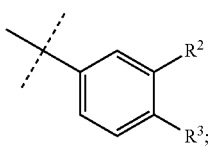

$R^2$ is selected from hydrogen, F, Cl or $C_{1-3}$alkyl;
$R^3$ is selected from hydrogen, F, Cl, CN or $SO_2C_{1-3}$alkyl.

In still a further embodiment $R^1$ is

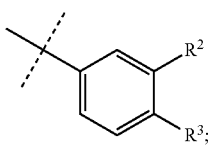

$R^2$ is selected from hydrogen, F or $C_{1-3}$alkyl;
$R^3$ is selected from hydrogen, F or CN.

In still a further embodiment $R^1$ is selected from

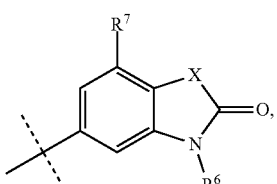

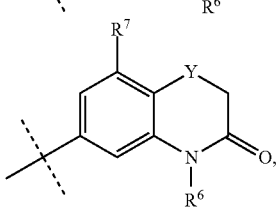

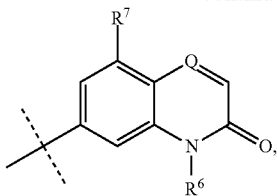

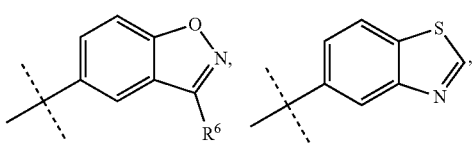

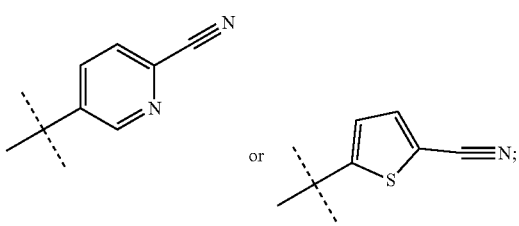

X is selected from O, S or $CF_2$;
Y is selected from O or S;
Q is selected from CH or N;
$R^6$ is selected from $C_{1-3}$alkyl, wherein said $C_{1-3}$alkyl is optionally substituted by 1, 2 or 3 F and optionally by one substituent selected from OH, $OC_{1-3}$alkyl, $N(C_{1-3}alkyl)_2$, cyclopropyl, or tetrahydropyran;
$R^7$ is selected from hydrogen, F, Cl or $CH_3$.

In still a further embodiment $R^1$ is selected from

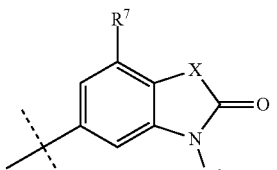

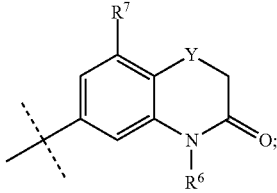

X is selected from O, S or $CF_2$;
Y is selected from O or S;
$R^6$ is selected from $C_{1-3}$alkyl, wherein said $C_{1-3}$alkyl is optionally substituted by 1, 2 or 3 F and optionally by one substituent selected from OH, $OC_{1-3}$alkyl, $N(C_{1-3}alkyl)_2$, cyclopropyl, or tetrahydropyran;
$R^7$ is selected from hydrogen, F, Cl or $CH_3$.

In still a further embodiment $R^1$ is selected from

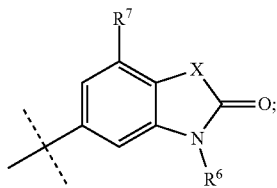

X is selected from O, S or $CF_2$;
$R^6$ is selected from $C_{1-3}$alkyl, wherein said $C_{1-3}$alkyl is optionally substituted by 1, 2 or 3 F;
$R^7$ is selected from hydrogen, F, Cl or $CH_3$.

In still a further embodiment $R^1$ is selected from

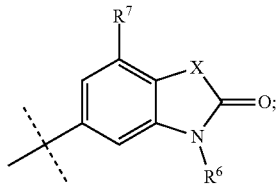

X is O;
$R^6$ is selected from $C_{1-3}$alkyl, wherein said $C_{1-3}$alkyl is optionally substituted by 1, 2 or 3 F;
$R^7$ is hydrogen.

In one embodiment $R^2$ is selected from hydrogen, F, Cl, Br, $OSO_2C_{1-3}$alkyl or $C_{1-3}$alkyl;

In a further embodiment $R^2$ is selected from hydrogen, F, Cl or $C_{1-3}$alkyl.

In still a further embodiment $R^2$ is selected from hydrogen, F or $C_{1-3}$alkyl.

In one embodiment $R^3$ is selected from hydrogen, F, Cl, Br, CN, $CF_3$, $SO_2C_{1-3}$alkyl, $CONH_2$ or $SO_2NR^4R^5$, wherein $R^4$ and $R^5$ together with the nitrogen atom to which they are attached form a azetidine, pyrrolidine or piperidine ring.

In a further embodiment $R^3$ is selected from hydrogen, F, Cl, CN or $SO_2C_{1-3}$alkyl.

In still a further embodiment $R^3$ is selected from hydrogen, F or CN.

In one embodiment $R^6$ is selected from $C_{1-3}$alkyl, wherein said $C_{1-3}$alkyl is optionally substituted by 1, 2 or 3 F and optionally by one substituent selected from OH, $OC_{1-3}$alkyl, $N(C_{1-3}alkyl)_2$, cyclopropyl, or tetrapydropyran.

In a further embodiment $R^6$ is selected from $C_{1-3}$alkyl, wherein said $C_{1-3}$alkyl is optionally substituted by 1, 2 or 3 F;

In still a further embodiment $R^6$ is selected from methyl and ethyl.

In still a further embodiment $R^6$ is methyl.

In one embodiment $R^7$ is selected from hydrogen, F, Cl or $CH_3$.

In a further embodiment $R^7$ is hydrogen.

One or more above embodiments may be combined to provide further specific embodiments of the disclosure.

In one embodiment the compound of formula (I) is selected from:
(2S)—N-[(1S)-1-Cyano-2-(4'-cyanobiphenyl-4-yl)ethyl]-1,4-oxazepane-2-carboxamide,
(2S)—N-{(1S)-1-Cyano-2-[4-(3-methyl-2-oxo-2,3-dihydro-1,3-benzoxazol-5-yl)phenyl]ethyl}-1,4-oxazepane-2-carboxamide,
(2S)—N-{(1S)-1-Cyano-2-[4-(3,7-dimethyl-2-oxo-2,3-dihydro-1,3-benzoxazol-5-yl)phenyl]ethyl}-1,4-oxazepane-2-carboxamide,
4'-[(2S)-2-Cyano-2-{[(2S)-1,4-oxazepan-2-ylcarbonyl]amino}ethyl]biphenyl-3-yl methanesulfonate,
(2S)—N-{(1S)-1-Cyano-2-[4-(3-methyl-1,2-benzoxazol-5-yl)phenyl]ethyl}-1,4-oxazepane-2-carboxamide,
(2S)—N-{(1S)-1-Cyano-2-[4'-(trifluoromethyl)biphenyl-4-yl]ethyl}-1,4-oxazepane-2-carboxamide,
(2S)—N-[(1S)-1-Cyano-2-(3',4'-difluorobiphenyl-4-yl)ethyl]-1,4-oxazepane-2-carboxamide,
(2S)—N-{(1S)-1-Cyano-2-[4-(6-cyanopyridin-3-yl)phenyl]ethyl}-1,4-oxazepane-2-carboxamide,
(2S)—N-{(1S)-1-Cyano-2-[4-(4-methyl-3-oxo-3,4-dihydro-2H-1,4-benzothiazin-6-yl)phenyl]ethyl}-1,4-oxazepane-2-carboxamide,
(2S)—N-{(1S)-1-Cyano-2-[4-(3-ethyl-7-methyl-2-oxo-2,3-dihydro-1,3-benzoxazol-5-yl)phenyl]ethyl}-1,4-oxazepane-2-carboxamide,
(2S)—N-[(1S)-1-Cyano-2-{4-[3-(2-hydroxy-2-methylpropyl)-2-oxo-2,3-dihydro-1,3-benzoxazol-5-yl]phenyl}ethyl]-1,4-oxazepane-2-carboxamide,
(2S)—N-[(1S)-1-Cyano-2-{4-[3-(2,2-difluoroethyl)-7-fluoro-2-oxo-2,3-dihydro-1,3-benzoxazol-5-yl]phenyl}ethyl]-1,4-oxazepane-2-carboxamide,
(2S)—N-[(1S)-1-Cyano-2-(4-{3-[2-(dimethylamino)ethyl]-2-oxo-2,3-dihydro-1,3-benzoxazol-5-yl}phenyl)ethyl]-1,4-oxazepane-2-carboxamide,
(2S)—N-{(1S)-1-Cyano-2-[4-(3,3-difluoro-1-methyl-2-oxo-2,3-dihydro-1H-indol-6-yl)phenyl]ethyl}-1,4-oxazepane-2-carboxamide,
(2S)—N-{(1S)-1-Cyano-2-[4-(7-fluoro-3-methyl-2-oxo-2,3-dihydro-1,3-benzoxazol-5-yl)phenyl]ethyl}-1,4-oxazepane-2-carboxamide,
(2S)—N-{(1S)-1-Cyano-2-[4-(3-ethyl-2-oxo-2,3-dihydro-1,3-benzoxazol-5-yl)phenyl]ethyl}-1,4-oxazepane-2-carboxamide,
(2S)—N-[(1S)-1-Cyano-2-{4-[3-(cyclopropylmethyl)-2-oxo-2,3-dihydro-1,3-benzoxazol-5-yl]phenyl}ethyl]-1,4-oxazepane-2-carboxamide,
(2S)—N-[(1S)-1-Cyano-2-{4-[3-(2-methoxyethyl)-2-oxo-2,3-dihydro-1,3-benzothiazol-5-yl]phenyl}ethyl]-1,4-oxazepane-2-carboxamide,
(2S)—N-[(1S)-1-Cyano-2-{4-[2-oxo-3-(propan-2-yl)-2,3-dihydro-1,3-benzoxazol-5-yl]phenyl}ethyl]-1,4-oxazepane-2-carboxamide,
(2S)—N-{(1S)-1-Cyano-2-[4-(4-methyl-3-oxo-3,4-dihydro-2H-1,4-benzoxazin-6-yl)phenyl]ethyl}-1,4-oxazepane-2-carboxamide,
(2S)—N-[(1S)-1-Cyano-2-{4-[3-(2-methoxyethyl)-2-oxo-2,3-dihydro-1,3-benzoxazol-5-yl]phenyl}ethyl]-1,4-oxazepane-2-carboxamide,
(2S)—N-{(1S)-1-Cyano-2-[4-(5-cyanothiophen-2-yl)phenyl]ethyl}-1,4-oxazepane-2-carboxamide,
(2S)—N-[(1S)-2-(4'-Carbamoyl-3'-fluorobiphenyl-4-yl)-1-cyanoethyl]-1,4-oxazepane-2-carboxamide,
(2S)—N-{(1S)-1-Cyano-2-[4-(1-methyl-2-oxo-1,2-dihydroquinolin-7-yl)phenyl]ethyl}-1,4-oxazepane-2-carboxamide,
(2S)—N-[(1S)-1-Cyano-2-{4-[2-oxo-3-(tetrahydro-2H-pyran-4-ylmethyl)-2,3-dihydro-1,3-benzoxazol-5-yl]phenyl}ethyl]-1,4-oxazepane-2-carboxamide,
(2S)—N-{(1S)-2-[4-(7-Chloro-3-methyl-2-oxo-2,3-dihydro-1,3-benzoxazol-5-yl)phenyl]-1-cyanoethyl}-1,4-oxazepane-2-carboxamide, (2S)—N-[(1S)-1-Cyano-2-{4-[3-(2,2-difluoroethyl)-2-oxo-2,3-dihydro-1,3-benzoxazol-5-yl]phenyl}ethyl]-1,4-oxazepane-2-carboxamide, (2S)—N-[(1S)-1-Cyano-2-{4-[2-oxo-3-(2,2,2-trifluoroethyl)-2,3-dihydro-1,3-benzoxazol-5-yl]phenyl}ethyl]-1,4-oxazepane-2-carboxamide, (2S)—N-{(1S)-1-Cyano-2-[4-(3-methyl-2-oxo-2,3-dihydro-1,3-benzothiazol-5-yl)phenyl]ethyl}-1,4-oxazepane-2-carboxamide, (2S)—N-{(1S)-1-Cyano-2-[4'-(methylsulfonyl)biphenyl-4-yl]ethyl}-1,4-oxazepane-2-carboxamide, (2S)—N-{(1S)-2-[4'-(Azetidin-1-ylsulfonyl)biphenyl-4-yl]-1-cyanoethyl}-1,4-oxazepane-2-carboxamide, (2S)—N-[(1S)-1-Cyano-2-(4'-fluorobiphenyl-4-yl)ethyl]-1,4-oxazepane-2-carboxamide, (2S)—N-{(1S)-2-[4-(1,3-Benzothiazol-5-yl)phenyl]-1-cyanoethyl}-1,4-oxazepane-2-carboxamide, (2S)—N-[(1S)-1-Cyano-2-(4'-cyanobiphenyl-4-yl)ethyl]-1,4-oxazepane-2-carboxamide, or (2S)—N-{(1S)-1-Cyano-2-[4-(4-methyl-3-oxo-1,2,3,4-tetrahydroquinoxalin-6-yl)phenyl]ethyl}-1,4-oxazepane-2-carboxamide, and pharmaceutically acceptable salts thereof.

It shall be noted that any one of these specific compounds may be disclaimed from any of the herein mentioned embodiments of the disclosure.

Another embodiment is a product obtainable by any of the processes or examples disclosed herein.

Pharmacological Properties

The compounds of formula (I) and their pharmaceutically acceptable salts have activity as pharmaceuticals, in particular as inhibitors of dipeptidyl peptidase 1 activity, and thus may be used in the treatment of obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; alpha-1 antitrypsin deficiency; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus, acute lung injury, acute respiratory distress syndrome (ARDS), as well as exacerbations of each of the foregoing respiratory tract disease states, in particular exacerbations of all types of asthma or COPD.

Thus, there is provided a compound of formula (I), or a pharmaceutically acceptable salt thereof, as hereinbefore defined for use in therapy.

In a further aspect, there is provided the use of a compound of formula (I), or a pharmaceutically acceptable salt thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

In particular, the compounds of the disclosure (including pharmaceutically acceptable salts) may be used in the treatment of asthma {such as bronchial, allergic, intrinsic, extrinsic or dust asthma, particularly chronic or inveterate asthma (for example late asthma or airways hyper-responsiveness)}, chronic obstructive pulmonary disease (COPD) or allergic rhinitis.

There is also provided a method of treating, or reducing the risk of, an obstructive airways disease or condition (e.g. asthma or COPD) which comprises administering to a patient in need thereof a therapeutically effective amount of a compound of formula (I), or a pharmaceutically acceptable salt thereof, as hereinbefore defined.

In a further aspect, there is provided the use of a compound of formula (I), or a pharmaceutically acceptable salt thereof, as hereinbefore defined in the manufacture of a medicament for use in treating COPD.

In a further aspect, there is provided the use of a compound of formula (I), or a pharmaceutically acceptable salt thereof, as hereinbefore defined in the manufacture of a medicament for use in treating asthma.

In a further aspect, there is provided the use of a compound of formula (I), or a pharmaceutically acceptable salt thereof, as hereinbefore defined in the manufacture of a medicament for use in treating allergic rhinitis.

In a further aspect, there is provided a compound of formula (I), or a pharmaceutically acceptable salt thereof as hereinbefore defined for use in treating allergic rhinitis.

In a further aspect, there is provided a compound of formula (I), or a pharmaceutically acceptable salt thereof, as hereinbefore defined for use in treating COPD.

In a further aspect, there is provided a compound of formula (I), or a pharmaceutically acceptable salt thereof, as hereinbefore defined for use in treating asthma.

Combination Therapy

The compounds of formula (I), or a pharmaceutically acceptable salt thereof, may also be administered in conjunction with other compounds used for the treatment of the above conditions.

The disclosure further relates to a combination therapy wherein a compound of the disclosure, or a pharmaceutically acceptable salt thereof, and a second active ingredient are administered concurrently, sequentially or in admixture, for the treatment of one or more of the conditions listed above. Such a combination may be used in combination with one or more further active ingredients.

The present disclosure still further relates to the combination of a compound of the disclosure, or a pharmaceutically acceptable salt thereof, together with a glucocorticoid receptor agonist (steroidal or non-steroidal) such as triamcinolone, triamcinolone acetonide, prednisone, mometasone furoate, loteprednol etabonate, fluticasone propionate, fluticasone furoate, fluocinolone acetonide, dexamethasone cipecilate, desisobutyryl ciclesonide, clobetasol propionate, ciclesonide, butixocort propionate, budesonide, beclomethasone dipropionate, alclometasone dipropionate, 2,2,2-trifluoro-N-[(1S,2R)-2-[1-(4-fluorophenyl)indazol-5-yl]oxy-2-(3-methoxyphenyl)-1-methyl-ethyl]acetamide, or 3-[5-[(1R,2S)-2-(2,2-difluoropropanoylamino)-1-(2,3-dihydro-1,4-benzodioxin-6-yl)propoxy]indazol-1-yl]-N-[(3R)-tetrahydrofuran-3-yl]benzamide.

The present disclosure still further relates to the combination of a compound of the disclosure, or a pharmaceutically acceptable salt thereof, together with a p38 antagonist such as PH797804 (3-[3-Bromo-4-(2,4-difluoro-benzyloxy)-6-methyl-2-oxo-2H-pyridin-1-yl]-4,N-dimethyl-benzamide), losmapimod, PF03715455 (1-[5-tert-butyl-2-(3-chloro-4-hydroxy-phenyl)pyrazol-3-yl]-3-[[2-[[3-[2-(2-hydroxyethylsulfanyl)phenyl]-[1,2,4]triazolo[4,3-a]pyridin-6-yl]sulfanyl]phenyl]methyl]urea) or N-cyclopropyl-3-fluoro-4-methyl-5-[3-[[1-[2-[2-(methylamino)ethoxy]phenyl]cyclopropyl]amino]-2-oxo-pyrazin-1-yl]benzamide.

The present disclosure still further relates to the combination of a compound of the disclosure, or a pharmaceutically acceptable salt thereof, together with a phosphodiesterase (PDE) inhibitor such as a methylxanthanine including theophylline and aminophylline or a selective PDE isoenzyme inhibitor (including a PDE4 inhibitor or an inhibitor of the isoform PDE4D) such as tetomilast, roflumilast, oglemilast, ibudilast, GPD-1116 (3-benzyl-5-phenyl-1H-pyrazolo[4,3-c][1,8]naphthyridin-4-one), ronomilast, NVP ABE 171 (4-[8-(2,1,3-benzoxadiazol-5-yl)-1,7-naphthyridin-6-yl]benzoic acid), RPL554 (2-[(2E)-9,10-dimethoxy-4-oxo-2-(2,4,6-trimethylphenyl)imino-6,7-dihydropyrimido[6,1-a]isoquinolin-3-yl]ethylurea), CHF5480 ([(Z)-2-(3,5-dichloro-4-pyridyl)-1-(3,4-dimethoxyphenyl)vinyl](2S)-2-(4-isobutylphenyl)propanoate), or GSK256066 (6-[3-(dimethylcarbamoyl)phenyl]sulfonyl-4-(3-methoxyanilino)-8-methyl-quinoline-3-carboxamide).

The present disclosure still further relates to the combination of a compound of the disclosure, or a pharmaceutically acceptable salt thereof, together with a modulator of chemokine receptor function such as an antagonist of CCR1, CCR2, CCR2A, CCR2B, CCR3, CCR4, CCR5, CCR6, CCR7, CCR8, CCR9, CCR10 or CCR11 (for the C—C family), for example a CCR1, CCR2B or CCR5 receptor antagonist; CXCR1, CXCR2, CXCR3, CXCR4 or CXCR5 (for the C—X—C family), for example a CXCR2 or CXCR3 receptor antagonist; or CX$_3$CR1 for the C—X$_3$—C family. For example, the present disclosure relates to the combination of a compound of the disclosure with PS-031291 (pyrrolidine-1,2-dicarboxylic acid 2-[(4-chlorobenzyl)-methyl-amide] 1-[(4-trifluoromethyl-phenyl)-amide]), CCX-354 (1-[4-(4-chloro-3-methoxy-phenyl)piperazin-1-yl]-2-[3-(1H-imidazol-2-yl)pyrazolo[3,4-b]pyridin-1-yl]ethanone), vicriviroc, maraviroc, cenicriviroc, navarixin (2-hydroxy-N,N-dimethyl-3-[[2-[[(1R)-1-(5-methyl-2-furyl)propyl]amino]-3,4-dioxo-cyclobuten-1-yl]amino]benzamide), SB656933 (1-(2-chloro-3-fluoro-phenyl)-3-(4-chloro-2-hydroxy-3-piperazin-1-ylsulfonyl-phenyl)urea), N-[2-[(2,3-difluorophenyl)methylsulfanyl]-6-[(1R,2S)-2,3-dihydroxy-1-methyl-propoxy]pyrimidin-4-yl]azetidine-1-sulfonamide, N-[6-[(1R,2S)-2,3-dihydroxy-1-methyl-propoxy]-2-[(4-fluorophenyl)methylsulfanyl]pyrimidin-4-yl]-3-methyl-azetidine-1-sulfonamide or N-[2-[(2,3-difluorophenyl)methylsulfanyl]-6-[[(1R,2R)-2,3-dihydroxy-1-methyl-propyl]amino]pyrimidin-4-yl]azetidine-1-sulfonamide.

The present disclosure still further relates to the combination of a compound of the disclosure, or a pharmaceutically acceptable salt thereof, together with a leukotriene biosynthesis inhibitor, 5-lipoxygenase (5-LO) inhibitor or 5-lipoxygenase activating protein (FLAP) antagonist such as TA270 (4-hydroxy-1-methyl-3-octyloxy-7-sinapinoylamino-2(1H)-quinolinone), PF-4191834 (2H-pyran-4-carboxamide, tetrahydro-4-[3-[[4-(1-methyl-1H-pyrazol-5-yl)phenyl]thio]phenyl]-), setileuton, CMI977 (1-[4-[(2S,5S)-5-[(4-fluorophenoxy)methyl]tetrahydrofuran-2-yl]but-3-ynyl]-1-hydroxy-urea), fiboflapon (3-[3-tert-butylsulfanyl-1-[[4-(6-ethoxy-3-pyridyl)phenyl]methyl]-5-[(5-methyl-2-pyridyl)methoxy]indol-2-yl]-2,2-dimethyl-propanoic acid), GSK2190915 (1H-indole-2-propanoic acid, 3-[(1,1-dimethylethyl)thio]-1-[[4-(6-methoxy-3-pyridinyl)phenyl]methyl]-α,α-dimethyl-5-[(2-pyridinyl)methoxy]-), licofelone, quiflapon (3-[3-tert-butylsulfanyl-1-[(4-chlorophenyl)methyl]-5-(2-quinolylmethoxy)indol-2-yl]-2,2-dimethyl-propanoic acid), veliflapon ((2R)-2-cyclopentyl-2-[4-(2-quinolylmethoxy)phenyl]acetic acid), ABT080 (4,4-bis[4-(2-quinolylmethoxy)phenyl]pentanoic acid), zileuton, zafirlukast, or montelukast.

The present disclosure still further relates to the combination of a compound of the disclosure, or a pharmaceutically acceptable salt thereof, together with a CRTh2 antagonist or a DP2 antagonist such as ACT129968 (2-[2-[(5-acetyl-2-methoxy-phenyl)methylsulfanyl]-5-fluoro-benzimidazol-1-yl]acetic acid), AMG853 (2-[4-[4-(tert-butylcarbamoyl)-2-[(2-chloro-4-cyclopropyl-phenyl)sulfonylamino]phenoxy]-5-chloro-2-fluoro-phenyl]acetic acid), AM211 (2-[3-[2-[[benzylcarbamoyl(ethyl)amino]methyl]-4-(trifluoromethyl)phenyl]-4-methoxy-phenyl]acetic acid), 2-[4-acetamido-3-(4-chlorophenyl)sulfanyl-2-methyl-indol-1-yl]acetic acid, (2S)-2-[4-chloro-2-(2-chloro-4-ethylsulfonyl-phenoxy)phenoxy]propanoic acid, 2-[4-chloro-2-[2-fluoro-4-(4-fluorophenyl)sulfonyl-phenyl]phenoxy]acetic acid, or (2S)-2-[2-[3-chloro-4-(2,2-dimethylpyrrolidine-1-carbonyl)phenyl]-4-fluoro-phenoxy]propanoic acid.

The present disclosure still further relates to the combination of a compound of the disclosure, or a pharmaceutically acceptable salt thereof, together with a myeloperoxidase antagonist such as resveratrol, piceatannol, or 1-(2-isopropoxyethyl)-2-thioxo-5H-pyrrolo[3,2-d]pyrimidin-4-one.

In a further aspect of the present disclosure, there is provided a pharmaceutical composition (for example, for use as a medicament for the treatment of one of the diseases or conditions listed herein, such as COPD, asthma or allergic rhinitis) comprising a compound of the disclosure, or a pharmaceutically acceptable salt thereof, and at least one active ingredient selected from:
  a) a toll-like receptor agonist (such as a TLR7 or TLR9 agonist)
  b) an adenosine antagonist;
  c) a glucocorticoid receptor agonist (steroidal or nonsteroidal);
  d) a p38 antagonist;
  e) a PDE4 antagonist;
  f) a modulator of chemokine receptor function (such as a CCR1, CCR2B, CCR5, CXCR2 or CXCR3 receptor antagonist); or
  g) a CRTh2 antagonist;
as defined above.

In one embodiment the compound of the disclosure, or a pharmaceutically acceptable salt thereof, is administered concurrently or sequentially with one or more further active ingredients selected from those defined above. For example, the compound of the disclosure, or a pharmaceutically acceptable salt thereof, may be administered concurrently or sequentially with a further pharmaceutical composition for use as a medicament for the treatment of one of the diseases or conditions listed herein, such as a respiratory tract condition (e.g. COPD, asthma or allergic rhinitis). Said further pharmaceutical composition may be a medicament which the patient may already be prescribed (e.g. an existing standard or care medication), and may itself be a composition comprising one or more active ingredients selected from those defined above.

Pharmaceutical Compositions

For the above-mentioned therapeutic uses the dosage administered will vary with the compound employed, the mode of administration, the treatment desired and the disorder indicated. For example, the daily dosage of the compound of the disclosure, if inhaled, may be in the range from 0.05 micrograms per kilogram body weight (μg/kg) to 100 micrograms per kilogram body weight (μg/kg). Alternatively, if the compound is administered orally, then the daily dosage of the compound of the disclosure may be in the range from 0.01 micrograms per kilogram body weight (μg/kg) to 100 milligrams per kilogram body weight (mg/kg).

The compounds of formula (I), or pharmaceutically acceptable salts thereof, may be used on their own but will generally be administered in the form of a pharmaceutical composition in which the formula (I) compound/salt (active ingredient) is in association with pharmaceutically acceptable adjuvant(s), diluents(s) or carrier(s). Conventional procedures for the selection and preparation of suitable pharmaceutical formulations are described in, for example, "Pharmaceuticals—The Science of Dosage Form Designs", M. E. Aulton, Churchill Livingstone, $2^{nd}$ Ed. 2002.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present disclosure also provides pharmaceutical composition(s) comprising a compound of formula (I), or a pharmaceutically acceptable salt thereof, as hereinbefore defined in association with pharmaceutically acceptable adjuvant(s), diluent(s) or carrier(s).

The disclosure further provides a process for the preparation of a pharmaceutical composition of the disclosure which comprises mixing a compound of formula (I), or a pharmaceutically acceptable salt thereof, as hereinbefore defined with a pharmaceutically acceptable adjuvant(s), diluents(s) or carrier(s).

The pharmaceutical compositions may be administered topically (e.g. to the skin or to the lung and/or airways) in the form, e.g., of creams, solutions, suspensions, heptafluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); or by rectal administration in the form of suppositories.

For oral administration the compound of the disclosure may be admixed with adjuvant(s), diluent(s) or carrier(s), for example, lactose, saccharose, sorbitol, mannitol; starch, for example, potato starch, corn starch or amylopectin; cellulose derivative; binder, for example, gelatine or polyvinylpyrrolidone; disintegrant, for example cellulose derivative, and/or lubricant, for example, magnesium stearate, calcium stearate, polyethylene glycol, wax, paraffin, and the like, and then compressed into tablets. If coated tablets are required, the cores, prepared as described above, may be coated with a suitable polymer dissolved or dispersed in water or readily volatile organic solvent(s). Alternatively, the tablet may be coated with a concentrated sugar solution which may contain, for example, gum arabic, gelatine, talcum and titanium dioxide.

For the preparation of soft gelatine capsules, the compound of the disclosure may be admixed with, for example, a vegetable oil or polyethylene glycol. Hard gelatine capsules may contain granules of the compound using pharmaceutical excipients like the above-mentioned excipients for tablets. Also liquid or semisolid formulations of the compound of the disclosure may be filled into hard gelatine capsules.

Liquid preparations for oral application may be in the form of syrups, solutions or suspensions. Solutions, for example may contain the compound of the disclosure, the balance being sugar and a mixture of ethanol, water, glycerol and propylene glycol. Optionally such liquid preparations may contain coloring agents, flavoring agents, saccharine and/or carboxymethylcellulose as a thickening agent. Furthermore, other excipients known to those skilled in art may be used when making formulations for oral use.

Preparation of Compounds

The present disclosure further provides a process for the preparation of a compound of formula (I) as defined above.

General Preparation

The skilled person will recognise that the compounds of the disclosure may be prepared, in known manner, in a variety of ways. The routes below are merely illustrative of some of the methods that can be employed for the synthesis of compounds of formula (I).

The present disclosure further provides a process for the preparation of a compound of formula (I) or a pharmaceutically acceptable salt thereof as defined above which comprises reacting a compound of formula (II),

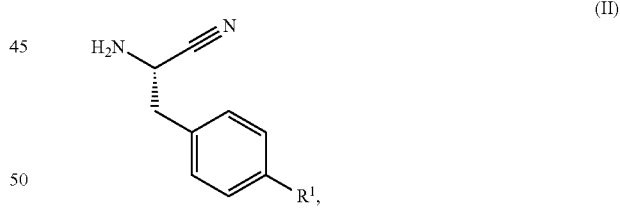

wherein $R^1$ is as defined in formula (I), with a compound of formula (III),

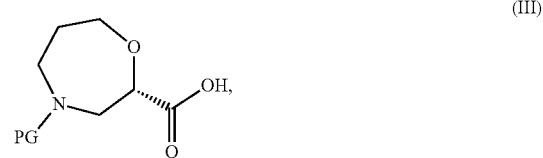

wherein PG represents a protecting group (e.g. tert-butoxycarbonyl), and optionally thereafter carrying out one or more of the following procedures:

converting a compound of formula (I) into another compound of formula (I)

removing any protecting groups forming a pharmaceutically acceptable salt.

The process is conveniently carried out in the presence of a base such as DiPEA or TEA and one or more activating agents such as EDCI, 2-pyridinol-1-oxide, or T3P. The reaction is conveniently carried out in an organic solvent such as DMF or DCM at a temperature, for example, in the range from 20° C. to 100° C., in particular at ambient temperature (25° C.).

Compounds of formula (II) may be prepared by reaction of a compound of formula (IV),

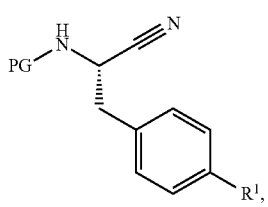

(IV)

wherein PG represents a protecting group (e.g. tert-butoxycarbonyl), with a suitable reagent to remove the protecting group PG. An example of a suitable reagent is formic acid.

Compounds of formula (IV) may be prepared by reacting a compound of formula (V),

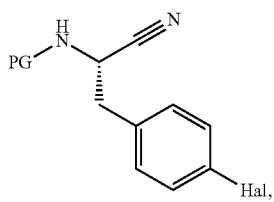

(V)

wherein PG represents a protecting group (e.g. tert-butoxycarbonyl) and Hal represents a halogen (e.g. I or Br), with a compound of formula (VI) or an ester thereof,

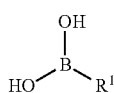

(VI)

wherein $R^1$ is as defined in formula (I), in the presence of a catalyst such as Pd(dppf)Cl$_2$. DCM or 1,1 bis(di-tert-butylphosphino)ferrocene palladium dichloride and a base such as potassium carbonate or sodium carbonate. The reaction is conveniently carried out in a solvent such as dioxane/water mixture or ACN/water mixture at a temperature, for example, in the range from 20° C. to 100° C., particularly at 75° C.

Compounds of formula (V) may be prepared from a compound of formula (VII),

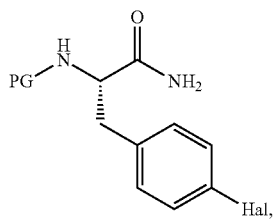

(VII)

in which PG represents a protecting group (e.g. tert-butoxycarbonyl) and Hal represents a halogen (e.g. I or Br), using standard literature procedures for the dehydration of an amide, for example with Burgess reagent, or with a reagent such as T3P with or without a base such as DiPEA, in a solvent such as DCM or DMF at a temperature in the range from −20° C. to 100° C., for example at 0° C.

Compounds of formula (VII) may be prepared by reacting a compound of formula (VIII), (VIII)

in which PG represents a protecting group (e.g. tert-butoxycarbonyl) and Hal represents a halogen (e.g. I or Br), with an aqueous ammonia solution, using standard literature procedures for the formation of an amide, for example, in the presence of a base such as N-ethyl-morpholine or DiPEA and an activating agent such as TBTU or T3P. The reaction is conveniently carried out in an organic solvent such as DMF, at a temperature in the range from −20° C. to 100° C., for example at 0° C.

Compounds of formula (VIII) are either commercially available, are known in the literature (e.g. from *Tetrahedron: Asymmetry*, 1998, 9, 503) or may be prepared using known techniques.

There is further provided a process for the preparation of a compound of formula (I), or a pharmaceutically acceptable salt thereof, as defined above which comprises reacting a compound of formula (IX), (IX)

wherein $R^1$ is as defined above and PG represents a protecting group (e.g. tert-butoxycarbonyl), using standard literature procedures for the dehydration of an amide, for example with Burgess reagent or with a reagent such as T3P with or without a base such as DiPEA, in a solvent such as DCM or DMF at a temperature in the range from −20° C. to 100° C., for example at 25° C., and thereafter reacting with a suitable reagent to remove the protecting group PG. An example of a suitable reagent is formic acid.

A compound of formula (IX) may be prepared by reacting a compound of formula (X), wherein PG represents a protecting group (e.g. tert-butoxycarbonyl), (X)

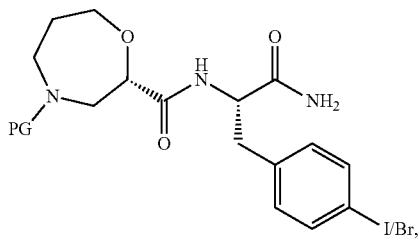

with a halide of formula (XI), wherein R¹ is defined as in formula (I),

R—Br/I    (XI)

in the presence of a catalyst such as bis[bis(1,2-diphenylphosphino)ethane]palladium(0), or Pd(dppf)Cl₂.DCM, and a base such as potassium carbonate or sodium carbonate. The reaction is conveniently carried out in a solvent such as dioxane/water mixture or ACN/water mixture at a temperature, for example, in the range from 20° C. to 100° C., particularly at 80° C.

A compound of formula (X) may be prepared by reacting a compound of formula (XII), wherein PG represents a protecting group (e.g. tert-butoxycarbonyl), (XII)

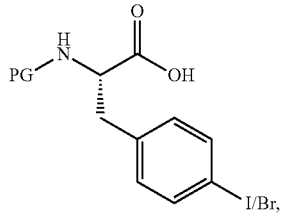

with B₂Pin₂ in the presence of a suitable catalyst such as Pd(dppf)Cl₂.DCM and with or without 1,1'-bis(diphenylphosphino)ferrocene or 1,1-bis(di-tert-butylphosphino)ferrocene palladium dichloride, with a suitable salt such as potassium acetate, in a solvent such as DMSO at a temperature in the range 60° C. to 100° C., for example at 85° C.

A compound of formula (XII) may be prepared by reacting a compound of formula (XIII), (XIII)

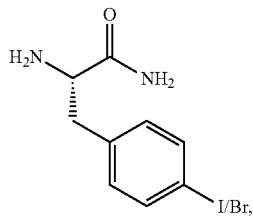

with a compound of formula (III), (III)

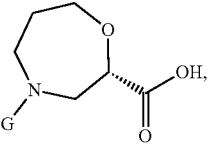

wherein PG represents a protecting group (e.g. tert-butoxycarbonyl) in the presence of a base such as DiPEA or TEA and an activating agent such as EDCI, 2-pyridinol-1-oxide, or T3P. The reaction is conveniently carried out in an organic solvent such as DMF or DCM at a temperature, for example, in the range from 20° C. to 100° C., in particular at ambient temperature (25° C.).

Compounds of formula (XIII) may be prepared by reacting a compound of formula (XIV), (XIV)

in which PG is as defined in formula (VII), with an aqueous ammonia solution, using standard literature procedures for the formation of an amide, for example, in the presence of a base such as N-ethyl-morpholine or DiPEA and an activating agent such as a "uronium" reagent (for example TBTU), or T3P. The reaction is conveniently carried out in an organic solvent such as DMF, at a temperature in the range from −20° C. to 100° C., for example at 0° C.

A compound of formula (IX) may be prepared by reacting a compound of formula (XII) wherein PG represents a protecting group (e.g. tert-butoxycarbonyl), with a compound of formula (VI) or a boronate ester thereof, in the presence of a catalyst such as bis[bis(1,2-diphenylphosphino)ethane]palladium(0) or Pd(dppf)Cl₂.DCM and a base such as potassium carbonate or sodium carbonate. The reaction is conveniently carried out in a solvent such as dioxane/water or ACN/water mixture at a temperature, for example, in the range from 20° C. to 100° C., particularly at 80° C.

There is further provided a process for the preparation of a compound of formula (I), or a pharmaceutically acceptable salt thereof, as defined above which comprises reacting a compound of formula (XV),

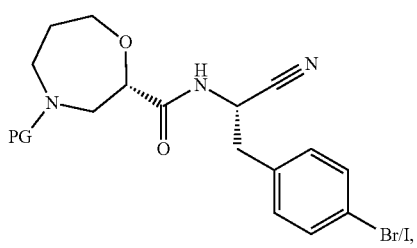

(XV)

wherein PG represents a protecting group (e.g. tert-butoxycarbonyl), with a compound of formula (VI) or an ester thereof, wherein $R^1$ is as defined in formula (I), in the presence of a catalyst such as Pd(dppf)Cl$_2$.DCM or 1,1 bis(di-tert-butylphosphino)ferrocene palladium dichloride and a base such as potassium carbonate or sodium carbonate. The reaction is conveniently carried out in a solvent such as dioxane/water mixture or ACN/water mixture at a temperature, for example, in the range from 20° C. to 100° C., particularly at 75° C., and thereafter reacting with a suitable reagent to remove the protecting group PG. An example of a suitable reagent is formic acid.

Compounds of formula (XV) may be prepared from compounds of formula (XII) using standard literature procedures for the dehydration of an amide, for example with Burgess reagent or a reagent such as TBTU or T3P with or without a base such as DiPEA, in a solvent such as DCM or DMF at a temperature in the range from −20° C. to 100° C., for example at 25° C.

There is further provided a process for the preparation of a compound of formula (I) or a pharmaceutically acceptable salt thereof as defined above which comprises reacting a compound of formula (XVI),

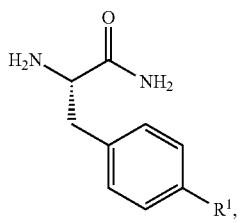

(XVI)

wherein $R^1$ is as defined in formula (I), with a compound of formula (III), conveniently carried out in the presence of a base such as DiPEA or TEA and one or more activating agents such as EDCI, 2-pyridinol-1-oxide, or T3P, followed by a dehydrating reagent such as T3P. The reaction is conveniently carried out in an organic solvent such as DMF or DCM at a temperature, for example, in the range from 20° C. to 100° C., in particular at ambient temperature (25° C.).

Compounds of formula (XVI) can be prepared from reacting compounds of formula (VII) with compounds of formula (VI) or an ester thereof, wherein $R^1$ is as defined in formula (I), in the presence of a catalyst such as Pd(dppf)Cl$_2$.DCM or 1,1 bis(di-tert-butylphosphino)ferrocene palladium dichloride and a base such as potassium carbonate or sodium carbonate. The reaction is conveniently carried out in a solvent such as dioxane/water mixture or ACN/water mixture at a temperature, for example, in the range from 20° C. to 100° C., particularly at 75° C., followed by deprotection of PG.

A compound of formula (III),

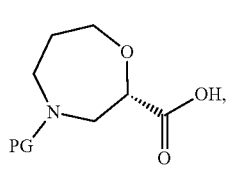

(III)

wherein PG represents a protecting group (e.g. tert-butoxycarbonyl) is either commercially available, or may be prepared from a compound of formula (XVII),

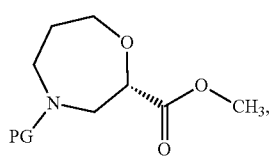

(XVII)

using literature procedures for mild ester hydrolysis (e.g. from Tetr. Lett., 2007, 48, 2497), for example with LiBr and a base such as TEA, in a solvent such as ACN/water mixture, for example at 25° C.

A compound of formula (XVII), wherein PG represents a protecting group (e.g. tert-butoxycarbonyl), may be prepared from a compound of formula (XVIII),

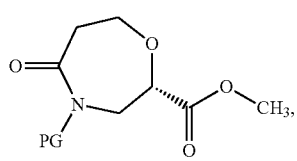

(XVIII)

using a reducing agent, for example BH$_3$-DMS, in a solvent such as THF, at a temperature in the range from 0 to 40° C., for example at 25° C.

A compound of formula (XVIII), wherein PG represents a protecting group (e.g. tert-butoxycarbonyl), may be prepared from a compound of formula (XIX), using a biocatalytic transformation for chemoselective lactam formation, for example using a lipase such as Novozym 435, in a solvent such as an ether, e.g. dioxane, at a temperature in the range from 0 to 80° C., for example at 55° C., followed by conditions for introduction of the protecting group PG.

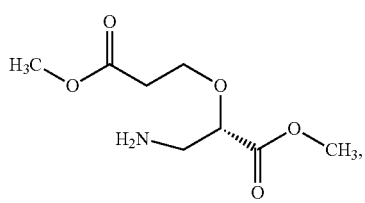

(XIX)

A compound of formula (XIX) may be prepared from a compound of formula (XX),

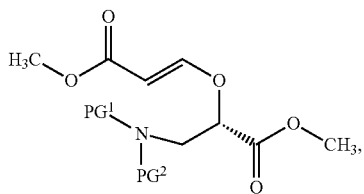

(XX)

wherein PG¹ and PG² represent protecting groups (e.g. bensyl), using conditions for hydrogenation, for example using H$_2$ (g), and a reagent such as palladium dihydroxide on carbon, in a solvent such as methanol or dioxane, under a pressure of for example 10 bar, at a temperature in the range from 25 to 80° C., for example at 40° C.

A compound of formula (XX), wherein PG¹ and PG² represent protecting groups (e.g. bensyl), may be prepared from a compound of formula (XXI),

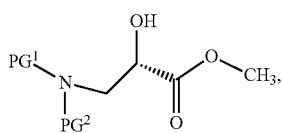

(XXI)

wherein PG¹ and PG² represent protecting groups (e.g. bensyl), using conditions for Oxa-Michael reaction, reacting with methyl propynoate, in presence of a base such as 4-methylmorpholine, in a solvent such as toluene, at a temperature in the range from 0 to 100° C., for example at 25° C.

A compound of formula (XXI), wherein PG¹ and PG² represent protecting groups (e.g. bensyl), may be prepared from reacting a diprotected bensyl amine (e.g. dibenzylamine) with (S)-methyl oxirane-2-carboxylate, in a solvent such as ethanol, at a temperature in the range from 0 to 78° C., for example at 70° C.

Alternatively, a compound of formula (III),

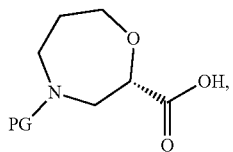

(III)

wherein PG represents a protecting group (e.g. tert-butoxycarbonyl) may be prepared from oxidation of a compound of formula (XXII),

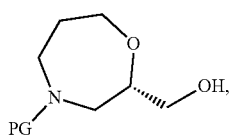

(XXII)

for example using reagents such as TEMPO, and sodium hypochlorite, optionally in presence of a salt such as sodium bromide, in a solvent such as DCM/water, and in presence of a buffer such as NaHCO$_3$, and a phase transfer catalyst such as tetrabutylammonium bisulphate, at a temperature in the range from 0 to 100° C., for example at 25° C.

A compound of formula (XXII), wherein PG represents a protecting group (e.g. tert-butoxycarbonyl) may be prepared from a compound of formula (XXIII),

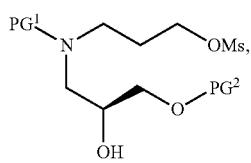

(XXIII)

wherein PG¹ and PG² represent protecting groups (e.g. bensyl), reacting with a base such as sodium hydride, in a solvent such as THF, at a temperature in the range from 0 to 60° C., for example at 25° C., followed by interconversion of protecting groups PG, PG¹ and PG², as defined in formula (XXII) and (XXIII).

A compound of formula (XXIII), wherein PG¹ and PG² represent protecting groups (e.g. bensyl), may be prepared from reacting protected 3-aminopropanol (e.g. N-bensyl-3-aminopropanol) with (S)-2-((benzyloxy)methyl)oxirane, in a solvent such as ethanol or propanol, at a temperature in the range from 0 to 70° C., for example at 40° C., followed by reacting the crude product with methanesulfonyl chloride, in presence of a base such as DiPEA, in a solvent such as DCM, at a temperature in the range from −10 to 25° C., for example at −5° C.

Compounds of formula (VI) or an ester thereof, (VIII), (XI) and (XIV) are either commercially available, are known in the literature or may be prepared using known techniques. It will be appreciated by those skilled in the art that in the processes of the present disclosure certain functional groups such as hydroxyl or amino groups in the reagents may need to be protected by protecting groups. Thus, the preparation of the compounds of formula (I) may involve, at an appropriate stage, the removal of one or more protecting groups.

The skilled person will recognise that at any stage of the preparation of the compounds of formula (I), mixtures of isomers (e.g. racemates) of compounds corresponding to any of formulae (II)-(V), (VII)-(X) and (XXII)-(XVI) may be utilized. At any stage of the preparation, a single stereoisomer may be obtained by isolating it from a mixture of isomers (e.g., a racemate) using, for example, chiral chromatographic separation.

The protection and deprotection of functional groups is described in 'Protective Groups in Organic Synthesis', 4$^{th}$ Ed, T. W. Greene and P. G. M. Wuts, Wiley (2006) and 'Protecting Groups', 3$^{rd}$ Ed P. J. Kocienski, Georg Thieme Verlag (2005).

A further embodiment encompasses pharmaceutically acceptable salts of the compounds of formula (I).

A salt of a compound of formula (I) may be advantageous due to one or more of its chemical or physical properties, such as stability in differing temperatures and humidities, or a desirable solubility in H$_2$O, oil, or other solvent. In some instances, a salt may be used to aid in the isolation or purification of the compound. In some embodiments (particularly where the salt is intended for administration to an animal, e.g. a human, or is a reagent for use in making a compound or salt intended for administration to an animal), the salt is pharmaceutically acceptable.

Where the compound of formula (I) is sufficiently acidic, pharmaceutically acceptable salts include, but are not limited to, an alkali metal salt, e.g. Na or K, an alkali earth metal salt, e.g. Ca or Mg, or an organic amine salt. Where the compound of formula (I) is sufficiently basic, pharmaceutically acceptable salts include, but are not limited to, inorganic or organic acid addition salts.

There may be more than one cation or anion depending on the number of charged functions and the valency of the cations or anions.

For reviews on suitable salts, see Berge et al., *J Pharm. Sci.*, 1977, 66, 1-19 or "Handbook of Pharmaceutical Salts: Properties, selection and use", P. H. Stahl, P. G. Vermuth, IUPAC, Wiley-VCH, 2002.

In a salt proton transfer occurs between the compound of formula (I) and the counter ion of the salt. However, in some cases proton transfer may not be complete and the solid is not therefore a true salt. In such cases the compound of formula (I) and the "co-former" molecules in the solid primarily interact through non-ionic forces such as hydrogen bonding. It is accepted that the proton transfer is in fact a continuum, and can change with temperature, and therefore the point at which a salt is better described as a co-crystal can be somewhat subjective.

Where an acid or base co-former is a solid at rt and there is no or only partial proton transfer between the compound of formula (I) and such an acid or base co-former, a co-crystal of the co-former and compound of formula (I) may result rather than a salt. All such co-crystal forms of the compound of formula (I) are encompassed by the present disclosure.

The compounds of formula (I) may form mixtures of its salt and co-crystal forms. It is also to be understood that the present disclosure encompasses salt/co-crystal mixtures of the compound of formula (I).

Salts and co-crystals may be characterized using well known techniques, for example X-ray powder diffraction, single crystal X-ray diffraction (for example to evaluate proton position, bond lengths or bond angles), solid state NMR, (to evaluate for example, C, N or P chemical shifts) or spectroscopic techniques (to measure for example, O—H, N—H or COOH signals and IR peak shifts resulting from hydrogen bonding).

It is also to be understood that certain compounds of formula (I) may exist in solvated form, e.g. hydrates, including solvates of a pharmaceutically acceptable salt of a compound of formula (I).

In a further embodiment, certain compounds of formula (I) may exist as racemates and racemic mixtures, single enantiomers, individual diastereomers and diastereomeric mixtures. It is to be understood that the present disclosure encompasses all such isomeric forms. Certain compounds of formula (I) may also contain linkages (e.g. carbon-carbon bonds, carbon-nitrogen bonds such as amide bonds) wherein bond rotation is restricted about that particular linkage, e.g. restriction resulting from the presence of a ring bond or double bond. Accordingly, it is to be understood that the present disclosure encompasses all such isomers. Certain compound of formula (I) may also contain multiple tautomeric forms. It is to be understood that the present disclosure encompasses all such tautomeric forms. Stereoisomers may be separated using conventional techniques, e.g. chromatography or fractional crystallization, or the stereoisomers may be made by stereoselective synthesis.

In a further embodiment, the compounds of formula (I) encompass any isotopically-labeled (or "radio-labelled") derivatives of a compound of formula (I). Such a derivative is a derivative of a compound of formula (I) wherein one or more atoms are replaced by an atom having an atomic mass or mass number different from the atomic mass or mass number typically found in nature. Examples of radionuclides that may be incorporated include $^2$H (also written as "D" for deuterium).

In a further embodiment, the compounds of formula (I) may be administered in the form of a prodrug which is broken down in the human or animal body to give a compound of the formula (I). Examples of prodrugs include in vivo hydrolysable esters of a compound of the formula (I). An in vivo hydrolysable (or cleavable) ester of a compound of the formula (I) that contains a carboxy or a hydroxy group is, for example, a pharmaceutically acceptable ester which is hydrolyzed in the human or animal body to produce the parent acid or alcohol. For examples of ester prodrugs derivatives, see: *Curr. Drug. Metab.* 2003, 4, 461.

Various other forms of prodrugs are known in the art. For examples of prodrug derivatives, see: *Nature Reviews Drug Discovery* 2008, 7, 255 and references cited therein.

EXAMPLES

The disclosure will now be further explained by reference to the following non limiting examples.

(i) Unless stated otherwise, $^1$H NMR spectra were recorded on Bruker Avance III spectrometers operating at a field strength of 400, 500 or 600 MHz. Either the central peaks of chloroform-d (CDCl$_3$; $\delta$H 7.27 ppm), dimethylsulfoxide-d$_6$ (d$_6$-DMSO; $\delta$H 2.50 ppm) or methanol-d$_4$ (CD$_3$OD; $\delta$H 3.31 ppm) were used as references.

(ii) MS spectra were either recorded on a Micromass ZQ single quadrapole LC-MS or Quattro Micro LC-MS-MS, following analytical HPLC, using a Phenomenex Luna 5 C$_{18}$ (2), 100×4.6 mm. (plus guard cartridge) column, and a gradient of ACN containing 0.1% formic acid in 0.1% aq formic acid, or a Waters Xterra MS 5µ C18, 100×4.6 mm. (plus guard cartridge) column, and a gradient of ACN in 10 mM aq ammonium hydrogen carbonate. Ionisation was routinely ESCI an option which gives both ESI and APCI data from a single run. Alternatively, LC-MS experiments were performed using a Waters Acquity UPLC system combined with a Waters Xevo Q-ToF Mass Spectrometer in ESI mode. The UPLC system was equipped with both a BEH C18 column (1.7 µm, 2.1×50 mm) in combination with a 46 mM ammonium carbonate/NH$_3$ buffer at pH 10, and an HSS C18 column (1.8 µm, 2.1×50 mm) in combination with 10 mM formic acid, 1 mM ammonium formate buffer at pH 3. Where values for m/z are given, generally only ions which indicate the parent mass are reported, and the mass ions quoted are the positive or negative mass ions: [M]$^+$, [M+H]$^+$, [M–H]$^-$ or [M+2H-BOC]$^+$.

(iii) The title and sub-title compounds of the examples and preparations were named using the IUPAC name program ACD/Name 2012 from Acdlabs.

(iv) Unless stated otherwise, starting materials were commercially available, and all solvents and commercial reagents were of laboratory grade and used as received. Unless stated otherwise, operations were carried out at ambient temperature, i.e. in the range between 17-28° C. and, where appropriate, under an atmosphere of an inert gas such as nitrogen.

(iv) The X-ray diffraction analysis was performed according to standard methods, which can be found in e.g. Kitaigorodsky, A. I. (1973), Molecular Crystals and Molecules, Academic Press, New York; Bunn, C. W. (1948), Chemical Crystallography, Clarendon Press, London; or Klug, H. P. & Alexander, L. E. (1974), X-ray Diffraction Procedures, John Wiley & Sons, New York.

Samples were mounted on single silicon crystal (SSC) wafer mounts and powder X-ray diffraction was recorded with a PANalytical X'Pert PRO (reflection geometry, wavelength of X-rays 1.5418 Å nickel-filtered Cu radiation, Voltage 45 kV, filament emission 40 mA). Automatic variable divergence and anti scatter slits were used and the samples were rotated during measurement. Samples were scanned from 2-50° 2Theta using a 0.0130 step width and 116 or 233 seconds count time using a PIXCEL detector (active length 3.35° 2Theta). It is known in the art that an X-ray powder diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation. For example, persons skilled in the art of X-ray powder diffraction will realise that the relative intensities of peaks may vary according to the orientation of the sample under test and on the type and setting of the instrument used. The skilled person will also realise that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute and any crystalline form that provides a power diffraction pattern substantially identical to those disclosed herein fall within the scope of the present disclosure (for further information see Jenkins, R & Snyder, R. L. 'Introduction to X-Ray Powder Diffractometry' John Wiley & Sons, 1996).

Generally, a measurement error of a diffraction angle in an X-ray powder diffractogram may be approximately plus or minus 0.1° 2-theta, and such a degree of a measurement error should be taken into account when considering the X-ray powder diffraction data. Furthermore, it should be understood that intensities might fluctuate depending on experimental conditions and sample preparation (e.g. preferred orientation). The following definitions have been used for the relative intensity (%): 81-100%, vs (very strong); 41-80%, str (strong); 21-40%, med (medium); 10-20%, w (weak); 1-9%, vw (very weak).

The following abbreviations are used:

| ACN | Acetonitrile |
| --- | --- |
| Burgess reagent | Methyl N-(triethylammoniumsulfonyl)carbamate |
| BH$_3$-DMS | Borane dimethyl sulfide complex |
| CDI | 1,1'-Carbonyldiimidazole |
| DCM | Dichloromethane |
| DMF | N,N-Dimethylformamide |
| DMSO | Dimethyl sulfoxide |
| DiPEA | Diisopropylethylamine (Hunig's base) |
| EDCI | 1-Ethyl-3-(3-dimethylaminopropyl) carbodiimide hydrochloride |
| EtOAc | Ethyl acetate |
| g | Gram(s) |
| h | Hour(s) |
| HATU | (1-[Bis(dimethylamino)methylene]-1H-1,2,3-triazolo[4,5-b]pyridinium 3-oxid hexafluorophosphate) |
| HPLC | High performance liquid chromatography |
| L | Liter(s) |
| LC | Liquid chromatography |
| LCMS | Liquid chromatography-mass spectroscopy |
| min | Minute(s) |
| mL | Milliliter(s) |
| MTBE | Methyl tert-butyl ether |
| Pd(dppf)Cl$_2$•DCM | [1,1'-Bis(diphenylphosphino)ferrocene] dichloropalladium(II), complex with dichloromethane |
| Pin$_2$B$_2$ | Bis (pinacolato) diboron |
| rt | Room temperature |
| T3P | Propylphosphonic anhydride |
| TBTU | O-(Benzotriazol-1-yl)-N,N,N',N'-tetramethyluronium tetrafluoroborate |
| TCNB | 1,2,4,5-Tetrachloro-3-nitrobenzene |
| TEA | Triethylamine |
| TEMPO | 2,2,6,6-Tetramethylpiperidine 1-oxyl |
| THF | Tetrahydrofuran |
| XPhos | 2-Dicyclohexylphosphino-2',4',6'-triisopropylbiphenyl |

Preparation of Boronate Ester Intermediates

Boronate Ester 1

5-(5,5-Dimethyl-1,3,2-dioxaborinan-2-yl)-3,7-dimethyl-1,3-benzoxazol-2(3H)-one i) 5-Chloro-?-methyl-1,3-benzoxazol-2(3H)-one CDI (3.09 g, 19.0 mmol) was added to a solution of 2-amino-4-chloro-6-methylphenol (2.5 g, 15.9 mmol) in THF (65 mL). The reaction was heated at reflux for 2.5 h before cooling to rt. The reaction mixture was transferred to a separating funnel and diluted with EtOAc (100 mL). The mixture was washed sequentially with 2 M hydrochloric acid, saturated aqueous solution of sodium hydrogen carbonate and saturated sodium chloride solution. The organic extract was dried (sodium sulfate), filtered and concentrated under reduced pressure to afford the subtitled compound as a light brown solid (2.89 g, 98%). 1H NMR (400 MHz, DMSO-d$_6$): 11.84 (s, 1H), 7.10 (d, 1H), 7.06 (d, 1H), 2.37 (s, 3H).

ii) 5-Chloro-3,7-dimethyl-1,3-benzoxazol-2(3H)-one

Cesium carbonate (2.65 g, 8.12 mmol) was added to a solution of 5-chloro-7-methyl-1,3-benzoxazol-2(3H)-one (1.50 g, 8.12 mmol) in DMF (100 mL). After 20 min methyl iodide (0.61 mL, 9.84 mmol) was added dropwise and stirred at rt for 2 h before pouring onto ice-water (100 mL). The resultant brown precipitate was collected by filtration and dried in a vacuum oven to afford the subtitled compound as a brown solid (1.6 g, 100%). $^1$H NMR (400 MHz, DMSO-d$_6$): 7.27 (s, 1H), 7.07 (s, 1H), 2.31 (s, 3H) (one CH$_3$ under water peak)

iii) 5-(5,5-Dimethyl-1,3,2-dioxaborinan-2-yl)-3,7-dimethyl-1,3-benzoxazol-2(3H)-one Bis(neopentyl glycolato)diboron (342 mg, 1.52 mmol) and potassium acetate (198 mg, 2.02 mmol) were added to a solution of 5-chloro-3,7-dimethyl-1,3-benzoxazol-2(3H)-one (200 mg, 1.01 mmol) in 1,4-dioxane (5 mL). The reaction mixture was degassed under nitrogen for 15 min before XPhos (19 mg, 0.040 mmol) and chloro(2-dicyclohexylphosphino-2',4',6'-triisopropyl-1,1'-biphenyl)[2-(2'-amino-1,1'-biphenyl)]palladium(II) (XPhos-Pd-G2, 16 mg, 0.020 mmol) were added. The reaction mixture was heated at 80° C. for 3 h. After this time the reaction mixture was concentrated under reduced pressure and purified by silica gel column chromatography eluting with 0-20% EtOAc in iso-hexane to afford the title compound as a light brown oil (184 mg, 66%). $^1$H NMR (400 MHz, CDCl$_3$): δ 7.44 (s, 1H), 7.23 (s, 1H), 3.80 (s, 4H), 3.40 (s, 3H), 2.39 (s, 3H), 1.04 (s, 6H).

Boronate Ester 2

7-(5,5-Dimethyl-1,3,2-dioxaborinan-2-yl)-1-methylquinoxalin-2(1H)-one

Bis(neopentyl glycolato)diboron (1.42 mg, 6.30 mmol) and potassium acetate (823 mg, 8.40 mmol) were added to a solution of 7-bromo-1-methylquinoxalin-2(1H)-one (1.0 g, 4.2 mmol) in 1,4-dioxane (15 mL). The reaction mixture was degassed under nitrogen for 30 min before Pd(dppf) Cl$_2$.DCM (171 mg, 0.21 mmol) was added. The reaction mixture was heated at 80° C. for 3 h. After this time the reaction mixture was concentrated under reduced pressure and purified by silica gel column chromatography eluting with 30% EtOAc in iso-hexane to afford an orange solid. Trituration with diethyl ether afforded the title compound as an off-white solid (340 mg, 30%). $^1$H NMR (400 MHz, CDCl$_3$): δ 8.37-8.30 (m, 1H), 7.79 (m, 3H), 3.82 (s, 4H), 3.75 (s, 3H), 1.06 (s, 6H).

Boronate Ester 3

5-(5,5-Dimethyl-1,3,2-dioxaborinan-2-yl)-3-ethyl-1,3-benzoxazol-2(3H)-one i) 5-Bromo-3-ethyl-1,3-benzoxazol-2(3H)-one Cesium carbonate (1.79 g, 5.5 mmol) was added to a solution of 5-bromo-1,3-benzoxazol-2(3H)-one (1.07 g, 5.0 mmol) in DMF (10 mL). Ethyl iodide (0.44 mL, 5.5 mmol) was added dropwise and the reaction stirred at rt for 24 h. The solvents were removed under reduced pressure and the resultant oil dissolved in EtOAc. The organic extract was washed sequentially with water, saturated sodium chloride solution, dried (magnesium sulfate), filtered and concentrated under reduced pressure. The resultant oil was purified by silica gel column chromatography eluting with a ratio of 1:2 DCM:iso-hexane to afford the subtitled compound as a white solid (1.06 g, 88%). 1H NMR (400 MHz, CDCl$_3$): δ 7.25 (dd, 1H), 7.13 (d, 1H), 7.08 (d, 1H), 3.87 (dd, 2H), 1.39 (t, 3H).

ii) 5-(5,5-Dimethyl-1,3,2-dioxaborinan-2-yl)-3-ethyl-1,3-benzoxazol-2(3H)-one

Bis(neopentyl glycolato)diboron (616 mg, 2.73 mmol) and potassium acetate (487 mg, 4.96 mmol) were added to a solution of 5-bromo-3-ethyl-1,3-benzoxazol-2(3H)-one (600 mg, 2.48 mmol) in 1,4-dioxane (10 mL). The reaction mixture was degassed under nitrogen for 30 min before Pd(dppf)Cl$_2$.DCM (101 mg, 0.12 mmol) was added. The reaction mixture was heated at 80° C. for 4 h. After this time the reaction mixture was concentrated under reduced pressure and purified by silica gel column chromatography eluting with 0-20% EtOAc in iso-hexane to afford the title compound as an off-white solid (338 mg, 57%). $^1$H NMR (400 MHz, CDCl$_3$): δ 7.60 (d, 1H), 7.41 (s, 1H), 7.19 (d, 1H), 3.90 (dd, 2H), 3.79 (s, 4H), 1.43-1.35 (m, 3H), 1.04 (s, 6H).

Boronate Ester 4

5-(5,5-Dimethyl-1,3,2-dioxaborinan-2-yl)-3-ethyl-7-methyl-1,3-benzoxazol-2(3H)-one i) 5-Chloro-3-ethyl-7-methyl-1,3-benzoxazol-2(3H)-one Prepared according to procedure in Boronate ester 3 step i) using 5-chloro-7-methyl-1,3-benzoxazol-2(3H)-one (Boronate ester 1 step i) to afford the subtitled compound as a brown solid (258 mg, 82%). $^1$H NMR (400 MHz, CDCl$_3$): δ 6.93 (s, 1H), 6.82 (d, 1H), 3.85 (q, 2H), 2.35 (s, 3H), 1.37 (t, 3H).

ii) 5-(5,5-Dimethyl-1,3,2-dioxaborinan-2-yl)-3-ethyl-7-methyl-1,3-benzoxazol-2(3H)-one Prepared according to procedure in Boronate ester 1 step iii) using 5-chloro-3-ethyl-7-methyl-1,3-benzoxazol-2(3H)-one to afford the title compound as an orange solid (285 mg, 81%). $^1$H NMR (400 MHz, CDCl$_3$): δ 7.42 (s, 1H), 7.24 (s, 1H), 3.93-3.83 (m, 2H), 3.78 (s, 4H), 2.37 (s, 3H), 1.41-1.32 (m, 3H), 1.04 (s, 6H).

Boronate Ester 5

5-(5,5-Dimethyl-1,3,2-dioxaborinan-2-yl)-3-(2-hydroxy-2-methylpropyl)-1,3-benzoxazol-2(3H)-one i) 5-Bromo-3-(2-oxopropyl)-1,3-benzoxazol-2(3H)-one Prepared according to procedure in Boronate ester 3 step i) using 5-bromo-1,3-benzoxazol-2(3H)-one and chloroacetone to afford the subtitled compound as a yellow solid (1.31 g, 94%). $^1$H NMR (400 MHz, CDCl$_3$): δ 7.28-7.24 (m, 1H), 7.11 (d, 1H), 6.93 (d, 1H), 4.59 (s, 2H), 2.31 (s, 3H).

ii) 5-Bromo-3-(2-hydroxy-2-methylpropyl)-1,3-benzoxazol-2(3H)-one

Methyl magnesium chloride (1.62 mL, 4.87 mmol, 3 M solution in THF) was added to a solution of 5-bromo-3-(2-oxopropyl)-1,3-benzoxazol-2(3H)-one (1.31 g, 4.87 mmol) in THF (20 mL) at 0° C. with stirring. After 1 h additional methyl magnesium chloride (0.81 mL, 2.43 mmol) was added. The reaction was warmed to rt and stirred for 1 h before quenching with ammonium chloride (saturated aqueous solution). The reaction mixture was diluted with EtOAc and the layers separated. The organic extracts were washed sequentially with water, saturated sodium chloride solution, dried (magnesium sulphate), filtered and concentrated under reduced pressure. The crude product was purified by silica gel column chromatography eluting with EtOAc and iso-hexane to afford the subtitled compound as a brown solid (428 mg, 31%). 1H NMR (400 MHz, CDCl$_3$): δ 8.26 (s, 1H), 7.28-7.23 (m, 1H), 7.16-7.03 (m, 1H), 7.00-6.89 (m, 1H), 3.86 (s, 2H), 1.61 (s, 6H).

iii) 5-(5,5-Dimethyl-1,3,2-dioxaborinan-2-yl-3-(2-hydroxy-2-methylpropyl)-1,3-benzoxazol-2(3H)-one Prepared according to procedure in Boronate ester 3 step ii) using 5-bromo-3-(2-hydroxy-2-methylpropyl)-1,3-benzoxazol-2(3H)-one to afford the title compound as an orange solid (269 mg, 56%). 1H NMR (400 MHz, CDCl$_3$): δ 8.53

(s, 1H), 7.62 (dd, 1H), 7.42 (d, 1H), 7.06 (d, 1H), 3.96 (s, 2H), 3.76 (s, 4H), 1.62 (s, 6H), 1.11-0.96 (m, 6H).

Boronate Ester 6

5-(5,5-Dimethyl-1,3,2-dioxaborinan-2-yl)-7-fluoro-3-methyl-1,3-benzoxazol-2(3H)-one i) 5-Bromo-7-fluoro-1_3-benzoxazol-2(3H)-one

CDI (2.38 g, 14.70 mmol) was added to a solution of 2-amino-4-bromo-6-fluorophenol (2.5 g, 12.25 mmol) in THF (65 mL). The reaction was heated at reflux for 2.5 h before cooling to rt. The reaction mixture was transferred to a separating funnel and diluted with EtOAc (100 mL). The mixture was washed sequentially with 2 M hydrochloric acid, saturated aqueous solution of sodium hydrogen carbonate and saturated sodium chloride solution. The organic extracts were dried (sodium sulfate), filtered and concentrated under reduced pressure. The resultant dark brown solid was triturated with diethyl ether and iso-hexane to afford the subtitled compound as a light brown solid (2.01 g, 71%). 1H NMR (400 MHz, DMSO-$d_6$): δ 12.14 (s, 1H), 7.38 (dd, 1H), 7.16-7.15 (m, 1H).

ii) 5-Bromo-7-fluoro-3-methyl-1-=3-benzoxazol-2(3H)-one

A solution of 5-bromo-7-fluoro-1,3-benzoxazol-2(3H)-one (2.01 g, 8.74 mmol) in DMF (30 mL) was added dropwise to a suspension of sodium hydride (419 mg, 10.49 mmol, 60% dispersion in mineral oil) in DMF (50 mL) at 0° C. with stirring. The reaction was warmed to rt for 30 min then re-cooled to 0° C. Methyl iodide (653 μL) was added dropwise and the reaction allowed to warm to rt. After 18 h the reaction was cautiously quenched with water and transferred to a separating funnel. The mixture was extracted with diethyl ether (×3). The organic extracts were washed sequentially with saturated sodium chloride solution, dried (magnesium sulphate), filtered and concentrated under reduced pressure. The resultant material was triturated with diethyl ether and iso-hexane to afford the subtitled compound as a light brown solid (1.38 g, 64%). 1H NMR (400 MHz, DMSO-$d_6$): δ 7.49 (d, 1H), 7.44 (dd, 1H), 3.35 (s, 3H).

iii) 5-(5,5-Dimethyl-1,3,2-dioxaborinan-2-yl)-7-fluoro-3-methyl-1,3-benzoxazol-2(3H)-one Bis(neopentyl glycolato)diboron (1.39 g, 6.17 mmol) and potassium acetate (1.10 g, 11.20 mmol) were added to a solution of 5-bromo-7-fluoro-3-methyl-1,3-benzoxazol-2(3H)-one (1.38 g, 5.60 mmol) in 1,4-dioxane (20 mL). The reaction mixture was degassed with nitrogen for 15 min before Pd(dppf)Cl$_2$.DCM (229 mg, 0.28 mmol) was added. The reaction mixture was heated at 80° C. for 3 h. After this time the reaction mixture was concentrated under reduced pressure and purified by silica gel column chromatography eluting with 20% EtOAc in iso-hexane to afford the title compound as a light brown solid (1.16 g, 75%). $^1$H NMR (400 MHz, CDCl$_3$): δ 7.36 (d, 1H), 7.19 (m, 1H), 3.78 (s, 4H), 3.42 (s, 3H), 1.03 (s, 6H).

Boronate Ester 7

5-(5,5-Dimethyl-1,3,2-dioxaborinan-2-yl)-3-(2,2-difluoroethyl)-1,3-benzoxazol-2(3H)-one i) 5-Bromo-3-(2,2-difluoroethyl)-7-fluoro-1,3-benzoxazol-2(3H)-one

Prepared according to procedure in Boronate ester 3 step i) using 5-bromo-7-fluoro-1,3-benzoxazol-2(3H)-one (Boronate ester 6 step i) and 2,2-difluoroethyl trifluoromethane sulfonate to afford the subtitled compound as a brown solid (2.49 g, 89%). $^1$H NMR (400 MHz, CDCl$_3$): δ 7.16 (dd, 1H), 7.05 (s, 1H), 6.08 (tt, 1H), 4.16 (td, 2H).

ii) 5-(5,5-Dimethyl-1,3,2-dioxaborinan-2-yl)-3-(2,2-difluoroethyl-2-methylpropyl)-1,3-benzoxazol-2(3H)-one Prepared according to procedure in Boronate ester 3 step ii) using 5-bromo-3-(2,2-difluoroethyl)-7-fluoro-1,3-benzoxazol-2(3H)-one to afford the title compound as an off-white solid (1.15 g, 41%). 1H NMR (400 MHz, CDCl$_3$): δ 7.40 (d, 1H), 7.30-7.24 (m, 1H), 6.10 (tt, 1H), 4.23-4.12 (m, 2H), 3.78 (s, 4H), 1.03 (s, 6H).

Boronate Ester 8

5-(5,5-Dimethyl-1,3,2-dioxaborinan-2-yl)-3-(2-(dimethylamino)ethyl)-1,3-benzoxazol-2(3H)-one i) 5-Bromo-3(2-(dimethylamino)ethyl)-1,3-benzoxazol-2(3H)-one

2-Dimethylaminoethyl chloride hydrochloride (1.21 g, 8.41 mmol) was added to 5-bromo-1,3-benzoxazol-2(3H)-one (1.80 g, 8.41 mmol) and potassium carbonate (3.87 g, 28.0 mmol) in DMF (10 mL). The reaction was heated at 125° C. for 3.5 h before cooling to rt and pouring onto ice-water. The aqueous layer was extracted with EtOAc (4×100 mL). The combined organic extracts were dried (magnesium sulphate), filtered and concentrated under reduced pressure. The resultant oil was dissolved in diethyl ether, washed with water, dried (magnesium sulphate), filtered and concentrated under reduced pressure to afford the subtitled compound as a light brown oil (1.63 g, 68%). $^1$H NMR (400 MHz, CDCl$_3$): δ 7.23 (dd, 1H), 7.15 (d, 1H), 7.10-7.02 (m, 1H), 3.93-3.85 (m, 2H), 2.69-2.61 (m, 2H), 2.30 (s, 6H).

ii) 5-(5,5-Dimethyl-1,3,2-dioxaborinan-2-yl)-3-(2-(dimethylaminoethyl)-1,3-benzoxazol-2(3H)-one Prepared according to procedure in Boronate ester 3 step ii) using 5-bromo-3-(2-(dimethylamino)ethyl)-1,3-benzoxazol-2(3H)-one to afford the title compound as an off-white solid (1.15 g, 41%). Used without further purification in the next step.

Boronate Ester 9

6-(5,5-Dimethyl-1,3,2-dioxaborinan-2-yl)-3,3-difluoro-1-methyl-1,3-dihydro-2H-indol-2-one i) 6-Bromo-3,3-difluoro-1,3-dihydro-2H-indol-2-one

Bis(2-methoxyethyl)aminosulfur trifluoride (deoxo-fluor, 44.25 mL, 22.12 mmol, 50% solution in THF) was added dropwise over 30 min to a suspension of 6-bromoisatin (2.0 g, 8.75 mmol) in DCM (90 mL) at rt with stirring. After 24 h the reaction was cautiously quenched with saturated sodium hydrogen carbonate solution (40 mL) solution at 0° C. The layers were separated and the organics extracts dried (hydrophobic frit/phase separator) and concentrated under reduced pressure. The crude material was purified by silica gel column chromatography eluting with 20% EtOAc in iso-hexane to afford the subtitled compound as an orange solid (1.63 g, 74%). $^1$H NMR (400 MHz, CH$_3$OH-d$_4$): δ 7.50-7.46 (m, 1H), 7.36 (dd, 1H), 7.18 (d, 1H), (one exchangeable not observed).

ii) 6-Bromo-3,3-difluoro-1-methyl-1,3-dihydro-2H-indol-2-one

Prepared according to procedure in Boronate ester 3 step i) using 6-bromo-3,3-difluoro-1,3-dihydro-2H-indol-2-one and methyl iodide to afford the subtitled compound as an orange solid (1.39 g, 82%). Used without further purification in the next step.

iii) 6-(5-Dimethyl-1,3,2-dioxaborinan-2-yl-3,3-difluoro-1-methyl-1,3-dihydro-2H-indol-2-one Prepared according to procedure in Boronate ester 3 step ii) using 6-bromo-3,3-difluoro-1-methyl-1,3-dihydro-2H-indol-2-one to afford the title compound as an off-white solid (120 mg, 8%). $^1$H NMR (400 MHz, CDCl$_3$): δ 7.62 (t, 1H), 7.55-7.47 (m, 1H), 7.31-7.28 (m, 1H), 3.80 (s, 4H), 3.22 (s, 3H), 1.04 (s, 6H).

Boronate Ester 10

3-(Cyclopropylmethyl)-5-(5,5-dimethyl-1,3,2-dioxaborinan-2-yl)-1,3-benzoxazol-2(3H)-one i) 5-Bromo-3-(cyclopropylmethyl)-1,3-benzoxazol-2(3H)-one

Cesium carbonate (1.79 g, 5.5 mmol) was added to a solution of 5-bromo-1,3-benzoxazol-2(3H)-one (1.07 g, 5.0 mmol) in DMF (10 mL). (Bromomethyl)cyclopropane (743 mg, 5.5 mmol) was added dropwise and the reaction stirred at rt for 24 h. The solvents were removed under reduced pressure and the resultant oil dissolved in EtOAc. The organic extract was washed with water, saturated sodium chloride solution, dried (magnesium sulfate), filtered and concentrated under reduced pressure. The resultant oil was purified by silica gel column chromatography eluting with a 1:2 ratio of DCM:iso-hexane to afford the subtitled compound as a white solid (918 mg, 68%). $^1$H NMR (400 MHz, CDCl$_3$): δ 7.24 (dd, 1H), 7.17 (d, 1H), 7.13-7.04 (m, 1H), 3.68 (d, 2H), 1.29-1.17 (m, 1H), 0.69-0.54 (m, 2H), 0.51-0.41 (m, 2H).

ii) 3-(Cyclopropylmethyl)-5-(5,5-dimethyl)-1,3,2-dioxaborinan-2-yl)-1,3-benzoxazol-2(3H)-one Prepared according to procedure in Boronate ester 3 step ii) using 5-bromo-3-(cyclopropylmethyl)-1,3-benzoxazol-2 (3H)-one to afford the title compound as a brown solid (520 mg, 62%). Used without further purification in the next step.

Boronate Ester 11

5-(5,5-Dimethyl-1,3,2-dioxaborinan-2-yl)-3-(2-methoxyethyl)-1,3-benzothiazol-2(3H)-one i) 5-Chloro-3-(2-methoxyethyl)-1,3-benzothiazol-2(3H)-one

Prepared according to procedure in Boronate ester 1 step ii) using 5-chloro-1,3-benzothiazol-2(3H)-one and 1-bromo-2-methoxyethane to afford the subtitled compound as a yellow solid (3.5 g, 89%). $^1$H NMR (400 MHz, CDCl$_3$): δ 7.32 (d, 1H), 7.22 (d, 1H), 7.13 (dd, 1H), 4.12-4.06 (m, 2H), 3.71-3.65 (m, 2H), 3.34 (s, 3H).

ii) 5-(5,5-Dimethyl-1,3,2-dioxaborinan-2-yl)-3-(2-methoxyethyl)-1,3-benzothiazol-2(3H)-one Prepared according to procedure in Boronate ester 1 step iii) using 5-chloro-3-(2-methoxyethyl)-1,3-benzothiazol-2(3H)-one to afford the title compound as a pale brown solid (1.02 g, 64%). Used without further purification in the next step.

Boronate Ester 12

5-(5,5-Dimethyl-1,3,2-dioxaborinan-2-yl)-3-isopropyl-1,3-benzoxazol-2(3H)-one i) 5-Bromo-3-isopropyl-1,3-benzoxazol-2(3H)-one

Prepared according to procedure in Boronate ester 3 step i) using 5-bromo-1,3-benzoxazol-2(3H)-one and 2-iodopropane to afford the subtitled compound as a white solid (510 mg, 66%). Used without further purification in the next step.

ii) 5-(5,5-Dimethyl-1,3,2-dioxaborinan-2-yl)-3-isopropyl-1,3-benzoxazol-2(3H)-one Prepared according to procedure in Boronate ester 3 step ii) using 5-bromo-3-isopropyl-1,3-benzoxazol-2(3H)-one to afford the subtitled compound as a brown solid (132 mg, 19%). Used without further purification in the next step.

Boronate Ester 13

6-(5,5-Dimethyl-1,3,2-dioxaborinan-2-yl)-4-methyl-2H-1,4-benzoxazin-3(4H)-one Prepared according to procedure in Boronate ester 3 step ii) using commercially available 6-bromo-4-methyl-2H-1,4-benzoxazin-3(4H)-one to afford the title compound as a brown solid (520 mg, 62%). Used immediately without further purification.

Boronate Ester 14

7-(5,5-Dimethyl-1,3,2-dioxaborinan-2-yl)-1-methylquinolin-2(1H)-one i) 7-Bromoquinolin-2(1H)-one

A stirred solution mixture of 7-bromo-2-chloroquinoline (5.0 g, 20.6 mmol) in 5 M aqueous hydrochloric acid (133 mL) and 1,4-dioxane (14 mL) was heated at reflux for 2 h. The reaction was cooled and the resulting precipitate was collected by filtration and washed with water to afford the subtitled compound as a colourless solid (4.3 g, 93%). $^1$H NMR (400 MHz, DMSO-d$_6$): δ 11.80 (s, 1H), 7.91 (d, 1H), 7.63 (d, 1H), 7.48 (d, 1H), 7.34 (dd, 1H), 6.53 (d, 1H).

ii) 7-Bromo-1-methylquinolin-2(1H)-one

Sodium hydride (320 mg, 7.98 mmol, 60% dispersion on mineral oil) was added to a solution of 7-bromoquinolin-2(1H)-one (1.5 g, 6.64 mmol) in anhydrous THF at rt under an atmosphere of nitrogen with stirring. After 1 h the reaction mixture was cooled to 0° C. and methyl iodide (1.88 g, 0.81 ml, 13.28 mmol) was added and the reaction was allowed to slowly warm to rt. After 18 h the reaction was cautiously quenched with water (1 mL) and concentrated under reduced pressure. The resulting residue was partitioned between EtOAc and water. The layers were separated and the aqueous layer was extracted with EtOAc. The combined organic extracts were dried (magnesium sulfate), filtered and concentrated under reduced pressure. The residue was recrystallized from DCM by addition of isohexane to afford the subtitled compound as a colourless solid (650 mg, 40%). $^1$H NMR (400 MHz, CDCl$_3$): δ 7.62 (d, 1H), 7.53 (d, 1H), 7.40 (s, 1H), 7.35 (dd, 1H), 6.75-6.66 (m, 1H), 3.69 (s, 3H).

ii) 7-(5,5-Dimethyl-1,3,2-dioxaborinan-2-yl)-1-methylquinolin-2(1H)-one

Prepared according to procedure in Boronate ester 2 starting from 7-bromo-1-methylquinolin-2(1H)-one to afford the title compound as a pale pink solid (650 mg, 88%). 1H NMR (400 MHz, CDCl$_3$): δ 7.83 (s, 1H), 7.69-7.60 (m, 2H), 7.53 (d, 1H), 6.73 (d, 1H), 3.82 (s, 4H), 3.78 (s, 3H), 1.05 (s, 6H).

Boronate Ester 15

5-(5,5-Dimethyl-1,3,2-dioxaborinan-2-yl)-3-(tetrahydro-2H-pyran-4-ylmethyl)-1,3-benzoxazol-2(3H)-one i) 5-Bromo-3-(tetrahydro-2H-pyran-4-ylmethyl)-1,3-benzoxazol-2(3H)-one 4-(Chloromethyl)tetrahydro-2H-pyran (500 mg, 3.7 mmol) was added to 5-bromo-2-benzoxazolinone (795 mg, 3.7 mmol) and cesium carbonate (500 mg, 7.4 mmol) in DMF (10 mL). The reaction was heated at 110° C. for 48 h before cooling to rt and pouring onto ice-water. The resultant precipitate was collected by filtration and dried under vacuum to afford the subtitled compound as a light brown oil (840 mg, 73%). 1H NMR (400 MHz, DMSO-d$_6$): δ 7.70 (s, 1H), 7.34-7.27 (m, 2H), 3.88-3.78 (m, 2H), 3.71 (d, 2H), 3.25 (td, 2H), 2.11-1.99 (m, 1H), 1.53 (d, 2H), 1.35-1.22 (m, 2H).

ii) 5-(5,5-Dimethyl-1,3,2-dioxaborinan-2-yl)-3-(tetrahydro-2H-pyran-4-ylmethyl)-1,3-benzoxazol-2(3H)-one Prepared according to procedure in Boronate ester 2 starting from 5-bromo-3-(tetrahydro-2H-pyran-4-ylmethyl)-1,3-benzoxazol-2(3H)-one to afford the title compound as a orange solid (440 mg, 47%). 1H NMR (400 MHz, CDCl$_3$): δ 7.61 (dd, 1H), 7.37 (s, 1H), 3.98 (dd, 2H), 3.79 (s, 3H), 3.75-3.69 (m, 2H), 3.40-3.32 (m, 2H), 2.25-2.11 (m, 1H), 1.66-1.53 (m, 3H), 1.53-1.39 (m, 2H), 1.04 (s, 6H) (one H under CHCl$_3$ peak).

Boronate Ester 16

7-Chloro-5-(5,5-dimethyl-1,3,2-dioxaborinan-2-yl)-3-methyl-1,3-benzoxazol-2(3H)-one i) 4-Bromo-2-chloro-6-nitrophenol 70% aqueous nitric acid (11.5 mL, 190 mol) was added slowly to a solution of 4-bromo-2-chlorophenol (20.0 g, 96.4 mmol) in acetic acid (100 mL) at rt. The resultant precipitate was collected by filtration to afford the subtitled compound as a yellow solid (24.0 g). Used without further purification in the next step.

ii) 2-Amino-4-bromo-6-chlorophenol

Calcium chloride (443 mg, 4 mmol) and iron (11.16 g, 0.2 mol) were added to a solution of 4-bromo-2-chloro-6-nitrophenol (10.0 g) in ethanol (400 mL) and water (100 mL). The suspension was heated at 80° C. for 2 h. The reaction was cooled, filtered and the filtrate was concentrated under reduced pressure. The resulting residue was diluted with saturated sodium chloride solution (500 mL) and extracted with EtOAc (2×500 mL). The combined organic extracts were dried (magnesium sulfate), filtered and concentrated under reduced pressure to afford the subtitled compound as a black solid (4 g, 45%). $^1$H NMR (400 MHz, CDCl$_3$): δ 6.85 (d, 1H), 6.75 (d, 1H), 5.38 (s, 1H), 3.92 (bs, 2H).

iii) 5-Bromo-7-chloro-1,3-benzoxazol-2(3H)-one

CDI (4.0 g, 24.6 mmol) was added to a stirred solution of 2-amino-4-bromo-6-chlorophenol (2.0 g, 9.0 mmol) in anhydrous THF (50 mL). The mixture was heated at reflux for 2.5 h under an atmosphere of nitrogen. The reaction was allowed to cool and the solvents were removed under reduced pressure. The resulting residue was washed with 2 N aqueous hydrochloric acid then triturated with methanol to afford the subtitled compound as a brown solid (0.8 g, 36%). $^1$H NMR (400 MHz, DMSO-d$_6$): δ 12.18 (s, 1H), 7.46 (d, 1H), 7.27 (d, 1H).

iv) 5-Bromo-7-chloro-3-methyl-1,3-benzoxazol-2(3H)-one

Prepared according to procedure in Boronate ester 1 step ii) starting from 5-bromo-7-chloro-1,3-benzoxazol-2(3H)-one and substituting cesium carbonate for potassium carbonate to afford the subtitled compound as brown solid (700 mg, 83%). $^1$H NMR (400 MHz, CDCl$_3$): δ 7.26 (s, 1H), 7.02 (d, 1H), 3.40 (s, 3H).

v) 7-Chloro-5-(5,5-dimethyl-1,3,2-dioxaborinan-2-yl)-3-methyl-1,3-benzoxazol-2(3H)-one Prepared according to procedure in Boronate ester 2 starting from 5-bromo-7-chloro-3-methyl-1,3-benzoxazol-2(3H)-one to afford the title compound as a off-white solid (170 mg, 22%). $^1$H NMR (400 MHz, CDCl$_3$): δ 7.59 (s, 1H), 7.28 (s, 1H), 3.78 (s, 4H), 3.41 (s, 3H), 1.03 (s, 6H).

Boronate Ester 17

3-(2,2-Difluoroethyl)-5-(5,5-dimethyl-1,3,2-dioxaborinan-2-yl)-1,3-benzoxazol-2(3H)-one i) Chloro-3-(2,2-difluoroethyl)-1,3-benzoxazol-2(3H)-one Cesium carbonate (3.83 g, 11.8 mmol) was added to a solution of 5-chloro-1,3-benzoxazol-2(3H)-one (1 g, 5.89 mmol) in DMF (20 mL), followed by 2,2-difluoroethyl trifluoromethanesulfonate (1.38 g, 6.5 mmol) dropwise and the resulting mixture was stirred at rt for 30 min. After this time water (60 mL) was added and the resulting precipitate was collected by filtration, washed with water and dried in vacuo to afford the subtitled compound as a white solid (1.25 g, 91%). 1H NMR (400 MHz, CDCl$_3$): δ 7.24-7.18 (m, 1H), 7.08 (m, 1H), 7.01 (s, 1H), 6.17-5.85 (m, 1H), 4.14-4.04 (m, 2H).

ii) 3-(2,2-Difluoroethyl)-5-(5,5-dimethyl-1,3,2-dioxaborinan-2-yl)-1,3-benzoxazol-2(3H)-one Prepared according to procedure in Boronate ester 1 step iii) using 5-chloro-3-(2,2-difluoroethyl)-1,3-benzoxazol-2(3H)-one to afford the title compound as an off-white solid (670 mg, 40%). $^1$H NMR (400 MHz, CDCl$_3$): δ 7.67-7.61 (m, 1H), 7.48 (s, 1H), 7.21 (d, 1H), 6.26-5.93 (m, 1H), 4.22-4.10 (m, 2H), 3.78 (s, 4H), 1.03 (s, 6H).

Boronate Ester 18

3-(2,2,2-Trifluoroethyl)-5-(5,5-dimethyl-1,3,2-dioxaborinan-2-yl)-1,3-benzoxazol-2(3H)-one i) 5-Chloro-3-(2,2,2-trifluoroethyl)-1,3-benzoxazol-2(3H)-one Cesium carbonate (3.83 g, 11.8 mmol) followed by 2,2,2-trifluoroethyl trifluoromethanesulfonate (1.5 g, 6.5 mmol) were added to a solution of 5-chloro-1,3-benzoxazol-2(3H)-one (1 g, 5.89 mmol) in DMF (20 mL). The resulting mixture was stirred at rt for 30 min. Water (60 mL) was added and the resulting precipitate was collected by filtration, washed with water and dried in vacuo to afford the subtitled compound as a white solid (1.31 g, 89%). $^1$H NMR (400 MHz, CDCl$_3$): δ 7.19-7.15 (m, 2H), 7.08 (s, 1H), 4.40 (q, 2H).

ii) 3-(2,22-Trifluoroethyl)-5-(5,5-dimethyl-1,3,2-dioxaborinan-2-yl)-1,3-benzoxazol-2(3H)-one Prepared according to procedure in Boronate ester 1 step iii) using 5-chloro-3-(2,2,2-trifluoroethyl)-1,3-benzoxazol-2(3H)-one to afford the title compound as an off-white solid (670 mg, 40%). $^1$H NMR (400 MHz, CDCl$_3$): δ 7.67 (dd, 1H), 7.47 (s, 1H), 7.22 (d, 1H), 4.41 (dd, 2H), 3.78 (s, 4H), 1.03 (s, 6H).

Boronate Ester 19

5-(5,5-Dimethyl-1,3,2-dioxaborinan-2-yl)-3-methyl-1,3-benzothiazol-2(3H)-one i) 5-Chloro-3-methyl-1,3-benzthiazol-2(3H)-one Cesium carbonate (17.5 g, 53.8 mmol) was added to a solution of 5-chloro-1,3-benzothiazol-2(3H)-one (5.0 g, 26.9 mmol) in DMF (70 mL). After 20 min methyl iodide (2.51 mL, 40.4 mmol) was added dropwise. Upon complete addition the reaction mixture was stirred at rt for 2 h before pouring onto ice-water (300 mL). The resultant brown precipitate was collected by filtration and dried in a vacuum oven to afford the subtitled compound as a colourless solid (4.42 g, 82%). $^1$H NMR (400 MHz, CDCl$_3$): δ 7.35 (d, 1H), 7.17 (dd, 1H), 7.06 (d, 1H), 3.45 (s, 3H).

ii) 5-(5,5-Dimethyl-1,3,2-dioxaborinan-2-yl)-3-methyl-1,3-benzothiazol-2(3H)-one Prepared according to procedure in Boronate ester 1 step iii) using 5-chloro-3-methyl-1,3-benzothiazol-2(3H)-one to afford the title compound as an off-white solid (620 mg, 15%). $^1$H NMR (400 MHz, CDCl$_3$): δ 7.61 (dd, 1H), 7.50-7.36 (m, 2H), 3.80 (s, 4H), 3.48 (s, 3H), 1.04 (s, 6H).

Boronate Ester 20

6-(5,5-Dimethyl-1,3,2-dioxaborinan-2-yl)-4-methyl-2H-1,4-benzothiazin-3(4H)-one i) 2-((4-Bromo-2-nitrophenyl)thio)acetic acid Potassium carbonate (4.55 g, 33 mmol) and thioacetic acid (1.15 mL, 16.5 mmol) were added sequentially to a solution of 4-bromo-1-fluoro-2-nitrobenzene (3.02 g, 15 mmol) in DMF (20 mL) with stirring at rt. After 18 h the reaction was diluted with EtOAc and water. The layers were separated. The aqueous layer acidified and extracted with EtOAc. The organic extract was dried (magnesium sulphate), filtered and concentrated under reduced pressure to afford the subtitled compound as a yellow solid (2.60 g, 59%). $^1$H NMR (400 MHz, DMSO-d$_6$): δ 13.04 (s, 1H), 8.37 (d, 1H), 7.96-7.91 (m, 1H), 7.54 (d, 1H), 4.05 (s, 2H).

ii) 6-Bromo-2H-1,4-benzothiazin-3(4H)-one

Iron(II) sulfate heptahydrate (18.12 g, 65.17 mmol) in water (25 mL) was added slowly to a solution of ammonium hydroxide (26 mL) and 2-((4-bromo-2-nitrophenyl)thio)acetic acid (2.6 g, 8.93 mmol) at rt. After 3 h the reaction mixture was filtered through celite washing with ammonium hydroxide and water. The filtrate was acidified with concentrated hydrochloric acid and the resultant precipitate was collected by filtration. The solid was dissolved in EtOAc, dried (magnesium sulphate), filtered and concentrated under reduced pressure to afford the subtitled compound as a yellow solid (1.9 g, 93%). $^1$H NMR (400 MHz, DMSO-d$_6$): δ 10.64 (br, 1H), 7.36-7.26 (m, 1H), 7.15 (dd, 2H), 3.49 (s, 2H).

iii) 6-Bromo-4-methyl-2H-1,4-benzothiazin-3(4H)-one

Prepared according to the procedure in Boronate ester 1 step ii) starting with 6-bromo-2H-1,4-benzothiazin-3(4H)-one to afford the subtitled compound as a yellow solid (1.16 g, 86%). 1H NMR (400 MHz, CDCl$_3$): δ 7.25 (d, 1H), 7.21 (d, 1H), 7.15 (dd, 1H), 3.42 (s, 3H), 3.40 (s, 2H).

iv) 6-(5,5-Dimethyl-1,3,2-dioxaborinan-2-yl)-4-methyl-2H-1,4-benzothiazin-3(4H)-one Prepared according to procedure in Boronate ester 3 step ii) using 6-bromo-4-methyl-2H-1,4-benzothiazin-3(4H)-one to afford the title compound as a white solid (655 mg, 45%). $^1$H NMR (400 MHz, CDCl$_3$): δ 7.58-7.44 (m, 1H), 7.45 (dd, 1H), 7.38-7.30 (m, 1H), 3.77 (s, 4H), 3.48 (s, 3H), 3.47-3.35 (m, 2H), 1.03 (s, 6H).

Boronate Ester 21

5-(5,5-Dimethyl-1,3,2-dioxaborinan-2-yl)-3-(2-methoxyethyl)-1,3-benzoxazol-2(3H)-one i) 5-Bromo-3-(2-methoxyethyl)-1,3-benzoxazol-2(3H)-one Prepared according to procedure in Boronate ester 3 step i) using 5-bromo-1,3-benzoxazol-2(3H)-one to afford the subtitled compound as a yellow solid (1.15 g, 85%). 1H NMR (400 MHz, CDCl$_3$): δ 7.27-7.20 (m, 2H), 7.06 (d, 1H), 3.97 (t, 2H), 3.72-3.66 (m, 2H), 3.35 (s, 3H).

ii) 5-(5,5-Dimethyl-1,3,2-dioxaborinan-2-yl)-3-(2-methoxyethyl)-1,3-benzoxazol-2(3H)-one Prepared according to procedure in Boronate ester 3 step ii) using 5-bromo-3-(2-methoxyethyl)-1,3-benzoxazol-2(3H)-one to afford the title compound as a yellow oil. Used without further purification in the next step. (1.15 g, 85%).

Boronate Ester 22

5-(5,5-Dimethyl-1,3,2-dioxaborinan-2-yl)-3-methyl-1,3-benzoxazol-2(3H)-one

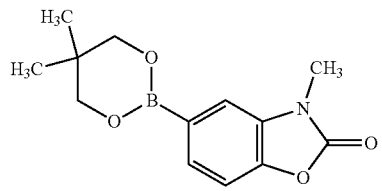 [SMILES: Cn1c(=O)oc2ccc(B3OCC(C)(C)CO3)cc21]

i) 5-Chloro-3-methyl-1,3-benzoxazol-2(3H)-one

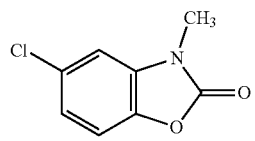

Cesium carbonate (19.21 g, 58.96 mmol) was added to a solution of 5-chloro-1,3-benzoxazol-2(3H)-one (10 g, 58.96 mmol) in DMF (100 mL). After 30 min methyl iodide (4.40 mL, 70.75 mmol) was added dropwise. Upon complete addition the reaction mixture was stirred at rt for 18 h before pouring onto ice-water (500 mL). The resultant white precipitate was collected by filtration and dried in a vacuum oven over P$_2$O$_5$ to afford the subtitled compound as a white solid (9.92 g, 92%). $^1$H NMR (400 MHz, DMSO-d$_6$): δ 7.46 (d, 1H), 7.36 (d, 1H), 7.17 (dd, 1H), 3.34 (s, 3H).

ii) 5-(5,5-Dimethyl-1,3,2-dioxaborinan-2-yl)-3-methyl-1,3-benzoxazol-2(3H)-one

Bis(neopentyl glycolato)diboron (5.54 g, 24.5 mmol) and potassium acetate (3.21 g, 32.7 mmol) were added to a solution of 5-chloro-3-methyl-1,3-benzoxazol-2(3H)-one (3.0 g, 16.3 mmol) in 1,4-dioxane (80 mL). The reaction mixture was degassed under nitrogen for 40 min before XPhos (311 mg, 0.65 mmol) and chloro(2-dicyclohexylphosphino-2',4',6'-triisopropyl-1,1'-biphenyl)[2-(2'-amino-1,1'-biphenyl)]palladium(II) (XPhos-Pd-G2, 257 mg, 0.33 mmol) were added. The reaction mixture was heated at 80° C. for 2 h. After this time the reaction mixture was concentrated under reduced pressure and purified by silica gel column chromatography eluting with 0-10% EtOAc in iso-hexane to afford the title compound as a yellow solid (4.8 mg, >100%). 1H NMR (400 MHz, CDCl$_3$): δ 7.61 (dd, 1H), 7.40 (s, 1H), 7.21-7.13 (m, 1H), 3.79 (s, 4H), 3.41 (s, 3H), 1.04 (s, 6H).

Preparation of Intermediate Building Blocks

Intermediate 1

4'-[(2S)-2-Amino-2-cyanoethyl]biphenyl-4-carbonitrile i) tert-Butyl [(1S)-1-cyano-2-(4'-cyanobiphenyl-4-yl)ethyl]carbamate Potassium carbonate (4.5 g, 36 mmol) was added to a suspension of tert-butyl N-[(1S)-1-cyano-2-(4-iodophenyl)ethyl]carbamate (prepared according to the procedure in WO2009/74829, p 47), (5.99 g, 16 mmol) and (4-cyanophenyl)boronic acid (2.64 g, 18 mmol) in 1,4-dioxane (60 mL) and water (8 mL). The suspension was stirred under a stream of nitrogen for 15 min before Pd(dppf)Cl$_2$.DCM (1.3 g) was added. The reaction was heated at 75° C. for 45 min before concentrating under reduced pressure. The resultant oil was diluted with EtOAc (200 mL), washed with water (100 mL) and saturated sodium chloride solution (50 mL). The organic extracts were dried (magnesium sulfate), filtered and evaporated under reduced pressure to afford a brown oil. The oil was purified by silica gel column chromatography eluting with 20-30% EtOAc in iso-hexane to afford the subtitled compound as a colourless solid (5.9 g, 90%). $^1$H NMR (400 MHz, DMSO-d$_6$): δ 10.63 (s, 1H), 7.96-7.81 (m, 4H), 7.73 (d, 2H), 7.45 (d, 2H), 4.71 (q, 1H), 3.18-3.05 (m, 2H), 1.36 (s, 9H).

ii) 4'-[(2S)-2-Amino-2-cyanoethyl]biphenyl-4-carbonitrile tert-Butyl [(1S)-1-cyano-2-(4'-cyanobiphenyl-4-yl)ethyl] carbamate (5.4 g, 15.5 mmol) was dissolved in formic acid (50 mL) and heated to 50° C. for 15 min on a pre-heated stirrer hotplate. The solution was evaporated under reduced pressure and diluted with EtOAc (150 mL). Saturated aqueous solution of sodium bicarbonate solution was added until the mixture was basic (pH 8). The EtOAc was separated and washed with saturated sodium chloride, dried (magnesium sulfate), filtered and evaporated under reduced pressure to give a yellow oil. The oil was purified by silica gel column chromatography eluting with EtOAc to afford the title compound as a colourless solid (2.88 g, 74%). $^1$H NMR (400 MHz, CDCl$_3$): δ 7.62 (m, 4H), 7.52 (m, 2H), 7.35 (d, 2H), 3.92 (t, 1H), 3.10-2.96 (m, 2H) (two exchangeable protons not observed).

Intermediate 2

(2S)-2-Amino-3-[4-(3-methyl-2-oxo-2,3-dihydro-1,3-benzoxazol-5-yl)phenyl]propanenitrile i) tert-Butyl {(1S)-1-cyano-2-[4-(3-methyl-2-oxo-2,3-dihydro-1,3-benzoxazol-5-yl)phenyl]ethyl}carbamate

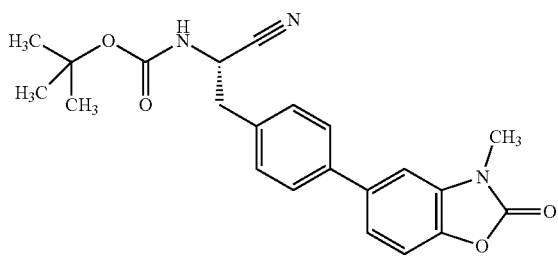 [SMILES: Cn1c(=O)oc2ccc(-c3ccc(C[C@@H](C#N)NC(=O)OC(C)(C)C)cc3)cc21]

5-(5,5-Dimethyl-1,3,2-dioxaborinan-2-yl)-3-methyl-1,3-benzoxazol-2(3H)-one (Boronate ester 22, 3.34 g, 12.81 mmol) and (S)-tert-butyl (1-cyano-2-(4-iodophenyl)ethyl) carbamate (prepared according to the procedure in WO 2009/074829, p. 47), 12.81 mmol were dissolved in 1,4-dioxane (340 mL) and water (12 mL). The reaction mixture was degassed under nitrogen for 30 min before potassium carbonate (2.66 g, 19.21 mmol) and Pd(dppf)Cl$_2$.DCM (1.05 g, 1.28 mmol) were added. The reaction mixture was heated at 80° C. for 1.5 h. After this time the reaction was concentrated under reduced pressure. The residue was diluted with EtOAc (200 mL) and water (50 mL). The mixture was filtered through celite and the layers separated. The organic extracts were washed with saturated sodium chloride solution, dried (magnesium sulphate), filtered and evaporated. The resultant oil was purified by silica gel column chromatography eluting with a gradient of 0-40% EtOAc in iso-hexane to afford the subtitled compound as a white solid (3.87 mg, 77%). $^1$H NMR (400 MHz, CDCl$_3$): δ 7.51-7.46 (m, 2H), 7.31 (d, 2H), 7.21-7.17 (m, 3H), 7.12-7.06 (m, 1H), 4.78 (s, 1H), 3.39 (s, 3H), 3.14-2.98 (m, 2H), 1.39 (s, 9H).

ii) (2S)-2-Amino-3-[4-(3-methyl-2-oxo-2,3-dihydro-1,3-benzoxazol-5-yl)phenyl]propanenitrile

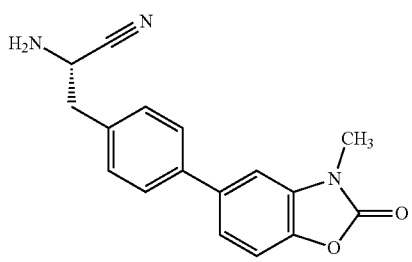 [SMILES: Cn1c(=O)oc2ccc(-c3ccc(C[C@H](N)C#N)cc3)cc21]

Formic acid (32 mL) was added to tert-butyl {(1S)-1-cyano-2-[4-(3-methyl-2-oxo-2,3-dihydro-1,3-benzoxazol-5-yl)phenyl]ethyl}carbamate (3.87 g, 9.84 mmol). The mixture was heated at 50° C. for 15 min on a pre-heated stirrer hotplate. After this time the solvents were removed under reduced pressure. The residue was dissolved in DCM, washed with saturated hydrogen carbonate solution, dried (phase separating cartridge) and concentrated under reduced pressure. The crude material was purified by silica gel column chromatography eluting with 80-100% EtOAc in iso-hexane to afford the title compound as a white solid (1.76 g, 59%). $^1$H NMR (400 MHz, CDCl$_3$): δ 7.60-7.50 (m, 2H), 7.39 (d, 2H), 7.34-7.30 (m, 1H), 7.25 (t, 1H), 7.14 (d, 1H), 4.02-3.96 (m, 1H), 3.45 (s, 3H), 3.18-3.01 (m, 2H), 1.67 (s, 2H).

Intermediate 3

(2S)-4-(tert-Butoxycarbonyl)-1,4-oxazepane-2-carboxylic acid

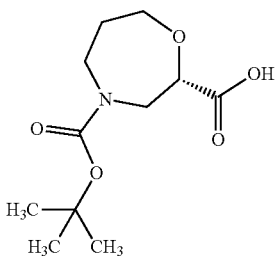 [SMILES: CC(C)(C)OC(=O)N1CCCO[C@H](C(=O)O)C1]

i) 3-{Benzyl[(2S)-3-(benzyloxy)-2-hydroxypropyl]amino}propan-1-ol

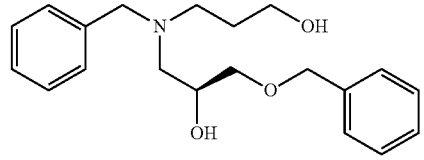 [SMILES: OCCCN(Cc1ccccc1)C[C@H](O)COCc1ccccc1]

A solution of N-benzylpropanolamine (3.3 g) and benzyl (S)-(+)-glycidyl ether (3.6 g) in ethanol (40 mL) was heated at 40° C. for 18 h. The solvent was evaporated under reduced pressure to give the subtitled compound as a colourless oil (6.8 g, 100%), which was used without further purification. $^1$H NMR (400 MHz, DMSO-d$_6$): δ 7.29 (m, 10H), 4.54 (m, 1H), 4.45 (s, 2H), 4.36 (t, 2H), 3.76 (m, 1H), 3.44 (m, 5H), 2.47 (m, 4H), 1.57 (m, 2H).

ii) (2S)-4-Benzyl-2-[(benzyloxy)methyl]-1,4-oxazepane

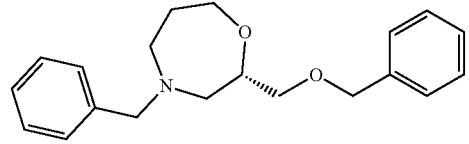 [SMILES: c1ccc(COC[C@@H]2CN(Cc3ccccc3)CCCO2)cc1]

Sodium hydride (15.2 g, 0.38 mol, 60% dispersion in oil) was added portion-wise to a stirred solution of 3-{benzyl [(2S)-3-(benzyloxy)-2-hydroxypropyl]amino}propan-1-ol (50.0 g, 0.153 mol) in THF (2.5 L) at 0° C. The reaction was stirred at 0° C. for 30 min before the portion-wise addition of p-toluenesulphonyl imidazole (37.8 g, 0.17 mol). The reaction was allowed to warm to rt and stirred for 4 h before cooling to 0° C. The reaction was quenched by the careful addition of saturated sodium hydrogen carbonate solution (70 mL). The solvents were removed under reduced pressure and the crude residue was partitioned between water (400 mL) and EtOAc (400 mL). The layers were separated and the aqueous portion was extracted with EtOAc (2×400 mL). The combined organic extracts were dried (magnesium sulfate), filtered and evaporated under reduced pressure to give an oil. The oil was purified by silica gel column chromatography eluting with a gradient of 0-50% EtOAc in iso-hexane to afford the subtitled compound as a colourless oil (12.2 g, 26%). 1H NMR (400 MHz, DMSO-$d_6$): δ 7.36-7.20 (m, 10H), 4.45-4.35 (m, 2H), 3.81-3.65 (m, 2H), 3.60-3.39 (m, 2H), 3.42-3.31 (m, 2H), 3.25 (dd, 1H), 2.86 (d, 1H), 2.78-2.70 (m, 1H), 2.54-2.46 (m, 1H) 2.37 (dd, 1H), 1.89-1.77 (m, 1H), 1.78-1.66 (m, 1H).

iii) tert-Butyl (2S)-2-hydroxymethyl)-1,4-oxazepane-4-carboxylate

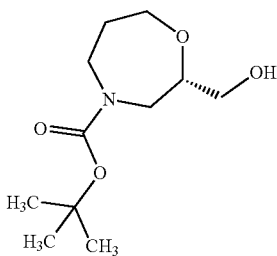 [SMILES: CC(C)(C)OC(=O)N1CCCO[C@H](CO)C1]

Di-tert-butyl dicarbonate (10.22 g, 47.1 mmol) and 20% palladium on carbon (16.5 g) were added to a solution of (2S)-4-benzyl-2-[(benzyloxy)methyl]-1,4-oxazepane (12.2 g, 39.2 mmol) in ethanol (250 mL) under nitrogen. The reaction mixture was shaken under an atmosphere of hydrogen at 50 psi for 18 h. After this time the reaction mixture was filtered through celite and washing with methanol. The solvent was evaporated under reduced pressure to give the subtitled compound as a colourless oil (11.16 g). 1H NMR (400 MHz, DMSO-$d_6$): δ 4.72-4.66 (m, 1H), 4.00-3.89 (m, 1H), 3.80-3.61 (m, 1H), 3.60-3.47 (m, 2H), 3.49-3.21 (m, 4H), 3.07-2.88 (m, 1H), 1.79-1.69 (m, 2H), 1.40 (s, 9H).

iv) (2S)-4-tert-Butoxycarbonyl)-1,4-oxazepane-2-carboxylic acid

Sodium bromide (1.46 g) and TEMPO (218 mg) were added to a solution of tert-butyl (2S)-2-(hydroxymethyl)-1,4-oxazepane-4-carboxylate (13.2 g, 46.6 mmol) in acetone (730 mL) and saturated sodium hydrogen carbonate (218 mL) at 0° C. 1,3,5-Trichloro-1,3,5-triazinane-2,4,6-trione (23.9 g, 102.5 mmol) was added portion-wise and the reaction mixture allowed to warm to rt over 18 h. The reaction was quenched by the addition of iso-propanol (30 mL) and stirred for 30 min. The reaction mixture was filtered through celite, washing with EtOAc. The filtrate was evaporated under reduced pressure, dissolved in 1 M sodium carbonate solution (100 mL) and extracted with EtOAc (2×200 mL). The aqueous solution was acidified with 2M HCl (150 mL) and extracted with EtOAc (3×400 mL). The combined organic extracts were dried (magnesium sulfate), filtered and evaporated under reduced pressure to give the title compound as a colourless solid (7.86 g, 68%). 1H NMR (400 MHz, DMSO-$d_6$): δ 12.71 (s, 1H), 4.22-4.15 (m, 1H), 3.98-3.80 (m, 2H), 3.70-3.50 (m, 2H), 3.45-3.11 (m, 1H), 3.21-3.06 (m, 1H), 1.71 (s, 2H), 1.40 (d, 9H).

Intermediate 3 (1$^{st}$ Alternative Synthesis)

(2S)-4-(tert-Butoxycarbonyl)-1,4-oxazepane-2-carboxylic acid i) Methyl(2S)-3-(dibenzylamino)-2-hydroxypropanoate

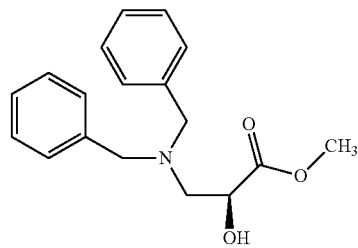 [SMILES: COC(=O)[C@@H](O)CN(Cc1ccccc1)Cc1ccccc1]

Under an atmosphere of nitrogen, (S)-methyl oxirane-2-carboxylate (117 g, 1134 mmol) and dibenzylamine (226 g, 1123 mmol) were heated at 70° C. over night. More (S)-methyl oxirane-2-carboxylate (1.15 g, 11.2 mmol) was added. Further stirred at 80° C. for 5 h. The mixture was then put under reduced pressure (0-10 mbar) over night at 50° C. This furnished the desired product as a pale brown viscous oil (342.7 g, 1145 mmol). Assay by $^1$H NMR=89% w/w, effective yield 91%. $^1$H NMR (400 MHz, CDCl$_3$): δ 2.77-2.92 (m, 2H), 3.13-3.4 (s, broad, 1H), 3.49 (d, J=13.5, 2H), 3.63 (s, 3H), 3.74 (d, J=13.5, 2H), 4.21 (dd, J=4.3, 6.7, 1H), 7.18-7.34 (m, 10H).

ii) Methyl 3-{[(2S)-3-(dibenzylamino)-1-methoxy-1-oxoproan-2-yl]oxy}prop-2-enoate

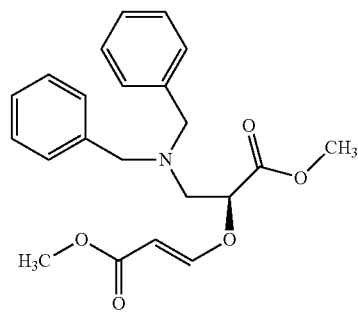 [SMILES: COC(=O)/C=C/O[C@@H](CN(Cc1ccccc1)Cc1ccccc1)C(=O)OC]

Methyl (2S)-3-(dibenzylamino)-2-hydroxypropanoate (342.7 g, 1018.8 mmol) was dissolved in toluene (200 mL). 4-methylmorpholine (22.4 mL, 203.8 mmol) was added followed by slow addition of methyl propiolate (108.8 g, 1273.6 mmol) during 60 min. The reaction temperature was kept in the interval 20-25° C. during this addition by cooling in a water/ice bath. After 3 h of stirring, the mixture was concentrated to give the desired product as a brown viscous oil (447.6 g, 1167 mmol, mixture of Z/E isomers). Assay by 1H NMR=87% w/w, (including both the Z and the E isomer). ¹H NMR (400 MHz, CDCl₃): δ 2.9-3.02 (m, 2H), 3.53 (d, 2H), 3.64 (s, 3H), 3.66 (s, 2H), 3.70 (d, 2H), 4.41 (td, 1H), 4.86 (d, 0.08H), 5.20 (d, 0.92H), 6.33 (d, 0.08H), 7.16-7.34 (m, 11H), 7.43 (d, 0.92H). ¹³C NMR (101 MHz, CDCl₃): δ 51.13 (s), 52.30 (s), 54.64 (s), 58.92 (d, J=5.6 Hz), 79.19 (s), 82.16 (s), 97.20 (s), 98.20 (s), 127.14 (s), 128.18 (d, J=8.0 Hz), 128.88 (s), 138.54 (s), 138.88 (s), 156.76 (s), 161.01 (s), 167.59 (s), 169.04 (s).

iii) Methyl (2S)-3-amino-2-(3-methoxy-3-oxo-propoxy)propanoate

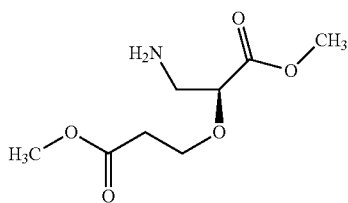

Pd(OH)₂, 20% on charcoal, 50% water (11.17 g, 79.50 mmol) was dried under a stream of nitrogen over night. This was then suspended in 1,4-dioxane (200 mL) and then added to a solution of methyl 3-{[(2S)-3-(dibenzylamino)-1-methoxy-1-oxopropan-2-yl]oxy}prop-2-enoate (438 g, 994 mmol) dissolved in 1,4-dioxane (3800 mL). The mixture was hydrogenated under 10 bar pressure of hydrogen at 30° C. over night. The temperature was increased to 40° C. and the mixture was allowed to stir for another 2 days. The mixture was filtered and rinsed with dioxane (200 mL). The dioxane solution (4527 g) was then used as such in the next step. Assay=4.6% w/w, effective yield 103%. 1H NMR (400 MHz, CDCl₃): δ 1.4 (s, 2H), 2.55-2.73 (m, 2H), 2.90-2.97 (dd, J=6.7, 13.5, 1H), 3.00-3.08 (dd, J=3.8, 13.5, 1H), 3.69 (s, 3H) 3.72-3.74 (m, 1H), 3.75 (s, 3H), 3.87-3.98 (ddd, 3.7, 6.3, 13.5, 2H).

iv) Methyl (2S)-5-oxo-1,4-oxazepane-2-carboxylate

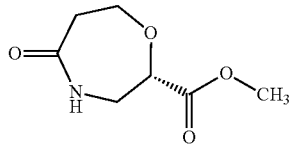

To a crude solution of methyl (2S)-3-amino-2-(3-methoxy-3-oxopropoxy)propanoate (204 g, 994 mmol) in dioxane (4.2 L) was added Novozyme 435 (immobilized, 75 g). The mixture was stirred for 2 days at 45° C. More Novozyme 435 (immobilized, 25 g) was added and the mixture was allowed to stir for another 2 days. The temperature was increased to 55° C. and the mixture was allowed to stir for 24 h. The mixture was filtered through a celite filter and rinsed with MeOH followed by concentration to a soap-like solid (254 g). This was further purified through preparative HPLC to give 85.2 g (492 mmol) of the desired product as a colorless solid (>90% w/w by ¹H NMR). ¹H NMR (400 MHz, CDCl₃): δ 6.98, (1H, s), 4.19 (2H, m), 3.77 (3H, s), 3.69 (1H, m), 3.59 (2H, m), 2.83 (1H, ddd) and 2.63 (1H, dd).

v) 4-tert-Butyl 2-methyl (2S)-5-oxo-1-oxazepane-2,4-dicarboxylate

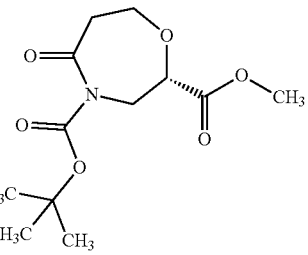

To a mixture of methyl (2S)-5-oxo-1,4-oxazepane-2-carboxylate (152.5 g, 863.0 mmol), N,N-dimethylpyridin-4-amine (2.11 g, 17.3 mmol) and THF (1200 mL) was added di-tert-butyl dicarbonate (192 g, 863.0 mmol). The resulting yellow suspension was then stirred at 30° C. for 20 h. More di-tert-butyl dicarbonate (11.30 g, 51.8 mmol) was added and the mixture was stirred at 30° C. for an additional 20 h. The mixture was concentrated to almost dryness on a 37° C. water bath. MTBE (400 mL) was added followed by concentration to almost dryness. This procedure was repeated once in order to remove t-BuOH formed in the reaction. Last, THF (300 mL) was added followed by concentration to a yellow oil that is used directly in the next step. Yield is assumed to be quantitative. ¹H NMR (400 MHz, CDCl₃): δ 1.48 (s, 9H); 2.77 (ddd, 1H, J=16.1, 7.0, 1.9 Hz); 2.94 (ddd, 1H, J=16.1, 9.3, 2.5 Hz); 3.75 (s, 3H); 3.80 (ddd, 1H, J=12.9, 9.1, 2.0 Hz); 3.91 (dd, 1H, J=16.0, 7.2 Hz); 4.12-4.30 (m, 2H); 4.38 (dd, 1H, J=16.0, 1.4 Hz). ¹³C NMR (126 MHz, CDCl₃): δ 27.9, 42.3, 48.8, 52.6, 63.4, 77.5, 83.8, 152.1, 169.0, 172.6.

vi) 4-tert-Butyl 2-methyl (2S)-1,4-oxazepane-2,4-dicarboxylate

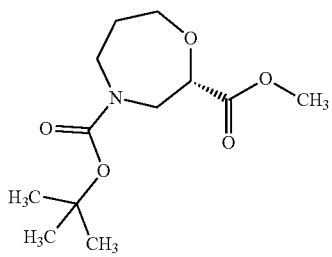 [SMILES: COC(=O)[C@@H]1CN(C(=O)OC(C)(C)C)CCCO1]

To the crude mixture of 4-tert-butyl 2-methyl (2S)-5-oxo-1,4-oxazepane-2,4-dicarboxylate (212.4 g, 777.2 mmol) in THF (2 L) from the previous step was during 30 minutes added a solution of BH₃-DMS (118 g, 1554 mmol). The reaction temperature was kept in the interval 20-23° C. during this addition. The mixture was then stirred at 23° C. for 17 h. The mixture was now slowly transferred to a solution of MeOH (1.5 L). The mixture was then combined with crude material obtained in a small scale experiment (starting from 23.6 g of 4-tert-butyl 2-methyl (2S)-5-oxo-1,4-oxazepane-2,4-dicarboxylate using the procedure as described above). The homogenous clear solution was then stirred at 20° C. for 1 h followed by concentration to almost dryness. MeOH (500 mL) was added followed by concentration to almost dryness, repeated once. ACN (500 mL) was then added followed by concentration to almost dryness, repeated once. The crude product (24% w/w, determined by ¹H NMR, bensylbensoat as internal standard) is then stored as a solution in ACN (500 mL). Effective yield=71%. ¹H NMR (400 MHz, MeOD, ~50:50 mixture of rotamers): δ 1.51 (s, 9H); 1.84-1.93 (m, 2H); 3.20-3.34 (m, 1H); 3.42-3.56 (m, 1H); 3.70-3.81 (m, 5H); 4.02-4.12 (m, 2H); 4.36-4.41 (m, 1H). ¹³C NMR (100.6 MHz, MeOD, ~50:50 mixture of rotamers) δ 28.6, 31.0, 31.5, 47.8, 48.2, 51.0, 51.2, 52.6, 68.6, 68.7, 77.6, 77.8, 81.4, 81.6, 156.7, 156.9, 172.8, 172.9.

vii) (2S)-4-(tert-Butoxycarbonyl)-1,4-oxazepane-2-carboxylic acid

LiBr (375 g, 4319 mmol) was added to a mixture of ACN (700 mL), water (30 mL), TEA (187 g, 1851 mmol) and water (30 mL). With a reaction temperature of 30° C., 4-tert-butyl 2-methyl (2S)-1,4-oxazepane-2,4-dicarboxylate (160 g, 617 mmol) dissolved in ACN (200 mL) was then added. The mixture was stirred vigorously at 20° C. over night.

Most of the ACN was removed through concentration. To the residue was added MTBE (500 mL). The yellow aqueous layer was washed with MTBE (200 mL). To the aqueous layer was then added MTBE (400 mL) followed by acidification to pH ~2 using 2M KHSO₄ solution. The aqueous layer was extracted with MTBE (2×300 mL) and the pooled organic layer was washed with water (100 mL) followed by concentration to a colorless solid (170 g, 80% w/w). The solid was suspended in 30% MTBE in heptane (600 mL) and the mixture was then stirred over night.

The mixture was filtered and the solid was washed with 25% MTBE in heptane (100 mL) followed by drying under reduced pressure at 40° C. This furnished 140.1 g (571 mmol) of the desired product, 93% w/w by ¹H NMR, 99.7% ee by HPLC. ¹H NMR (400 MHz, MeOD, mixture of 2 rotamers): δ 1.46 (s, 9H); 1.77-1.90 (m, 2H); 3.15-3.77 (m, 4H); 3.91-4.17 (m, 2H); 4.22-4.32 (m, 1H). ¹³C NMR (100.6 MHz, MeOD, mixture of 2 rotamers) δ 28.5, 28.6, 31.0, 31.3, 47.8, 47.9, 51.4, 68.6, 69.0, 77.7, 78.0, 81.4, 81.7, 156.8, 157.0, 174.0, 174.2.

Intermediate 3

(2S)-4-(tert-Butoxycarbonyl)-1,4-oxazepane-2-carboxylic acid (2ⁿᵈ Alternative Synthesis)

i) 3-{Benzyl[(2S)-3-(benzyloxy)-2-hydroxypropyl]amino}propan-1-ol

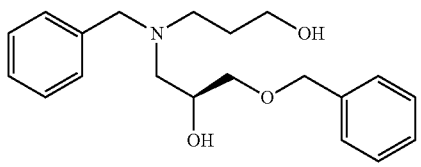 [SMILES: OCCCN(Cc1ccccc1)C[C@H](O)COCc1ccccc1]

The reactants 3-(benzylamino)propan-1-ol, 1219 g (7.16 mol) and (S)-2-((benzyloxy)methyl)oxirane, 1200 g (7.16 mol) were dissolved separately, in 2×3 L of 2-propanol and were charged separately to an inerted reactor and heated at 50° C. for 24 h. The reaction mixture was evaporated at 60° C., 110 mbar to an oil, 2.48 kg. The oil was dissolved in toluene, 1 L and evaporated to dryness. Yield: 2.45 kg Assay: ~95% Effective yield: ~98%. ¹H NMR (400 MHz, CDCl₃):

δ 1.59-1.78 (m, 2H), 2.47 (dd, J=13.3, 1H), 2.53-2.65 (m, 2H), 2.71-2.78 (ddd, 5.6, 7.7, 13.2, 1H), 3.31-3.45 (m, 3H), 3.50 (d, 1H), 3.67-3.74 (m, J=13.3, 3H), 3.93-3.99 (ddt, J=4.1, 4.1, 6.2, 8.3, 1H), 4.48 (s, 2H), 7.18-7.36 (m, 10H).

ii) 3-{Benzyl[(2S)-3-(benzyloxy)-2-hydroxypropyl]amino}propyl methanesulfonate

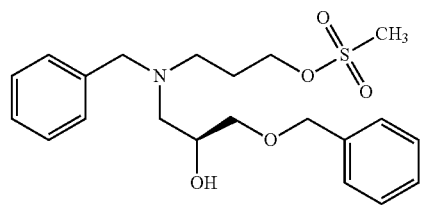 [SMILES: CS(=O)(=O)OCCCN(Cc1ccccc1)C[C@H](O)COCc1ccccc1]

The diol product from previous experiment, 147 g (446 mmol), was dissolved in 400 mL of DCM and cooled to −1° C. DIPEA, 72.3 mL (446 mmol) was added to the reactor at −1° C. The solution was cooled to −6° C. Then methane sulfonylchloride 51.1 g (446 mmol) in 200 mL of DCM was added dropwise to the diol solution at appr. −6° C. to −2° C. during 1 h. After addition the mixture was stirred for 30 min, before it was poured onto 400 mL of ice. Phase separation, wash with cold water twice, followed by brine, twice, evaporated to an oil. The oil was diluted with DCM and extracted with aq. sodium sulfate solution, filtered and evaporated to an oil, 176 g (97%), assay 85%. ¹H NMR (600 MHz, CDCl₃): δ 1.82-1.87 (m, 2H), 2.47-2.56 (m, 3H), 2.59-2.67 (m, 1H), 2.86 (s, 3H), 3.02 (s, 1H), 3.38-3.45 (m, 2H), 3.49 (d, 1H), 3.69 (d, 1H), 3.83-3.87 (m, 1H), 4.14-4.20 (m, 2H), 4.49 (s, 2H), 7.20-7.32 (m, 10H).

iii) (2S)-4-Benzyl-2-[(benzyloxy)methyl]-1,4-oxazepane

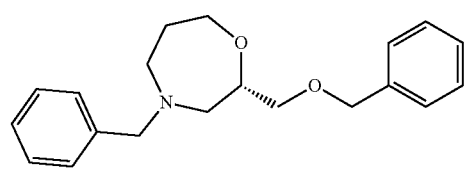 [SMILES: c1ccc(COC[C@@H]2CN(Cc3ccccc3)CCCO2)cc1]

The crude product from previous experiment, 169 g (approx assay 85%, 143.65 g, 0.35 mol) was dissolved in 300 mL dry THF and was added slowly (5 h) to NaH (1.4 eq., 18.46 g, 0.423 mol) in 200 mL of dry THF in a dry reactor under nitrogen at 25° C. (the sodium hydride paste was washed with heptane before the addition started). The reaction mixture was stirred over night at 25° C. The next day 400 mL of saturated aq. bicarbonate was added to the reaction mixture at rt. Initially gas was evolved. Phase separation, the water phase was discarded. The organic phase was evaporated to an oil. The oil was dissolved in 400 mL of isopropyl acetate. The isopropyl acetate solution was washed with 2 M NaOH (aq), 100 ml, followed by two washes with water (100 ml) and a brine wash. Evaporation gave 136 g, assay 65% w/w product. Estimated yield: 88 g (81%) 0.28 mol. Chromatography: EtOAc/heptane 254 nm.

Isolated yield: 81.6 g (0.26 mol, 74%) ¹H NMR (400 MHz, DMSO-d₆): δ 1.66-1.76 (m, 1H), 1.77-1.87 (m, 1H), 2.37

(dd, 1H), 2.46-2.5 (m, 1H), 2.68-2.77 (m, 1H), 2.81-2.89 (m, 1H), 3.24 (dd, 1H), 3.37 (dd, 1H), 3.64 (d, 2H), 3.64-3.74 (m, 1H), 3.76 (ddd, 2H), 4.35-4.43 (m, 2H), 7.18-7.37 (m, 10H).

iv) (2S)-1,4-Oxazepan-2-ylmethanol

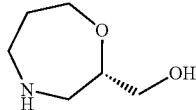

The product from previous experiment, 81.6 g (0.26 mol) was dissolved in methanol, 1 L and charged to the hydrogenation vessel under nitrogen. The catalyst, $PdOH_2$ (20%) 50% wet on charcoal, 10 g=3 mol % was slurried in ethanol and charged to the reaction vessel under nitrogen. The mixture was hydrogenated at 4.5 bars at ambient temperature for 72 h. Conversion was approx 50% and 10 g of new catalyst was added and pressure was raised to 8 bars, temperature was increased from ambient to 45° C. Hydrogenation over night. Conversion was approx 96%. 3 g of catalyst was added to the reaction mixture and the hydrogenation was continued for 6 h. Full conversion was reached and the reaction mixture was filtered and a sample of it was evaporated to give an oil. $^1$H NMR (500 MHz, MeOD): δ 1.60-1.79 (m, 2H), 2.42-2.53 (dd, J=8.8, 14, 1H), 2.62-2.81 (dddd, J=4.2, 7.3, 13.5, 49, 2H), 2.81-2.89 (dd, 1H), 2.94 (dd, 1H), 3.17 (s, 1H), 3.24-3.37 (qd, J=5.6, 11.4, 11.4, 11.4, 2H), 3.41-3.48 (m, 1H), 3.53 (td, J=3.9, 7.9, 7.8, 1H), 3.74-3.84 (dt, J=5.5, 5.5, 12.2, 1H).

v) tert-Butyl (2S)-2-(hydroxymethyl)-1,4-oxazepane-4-carboxylate

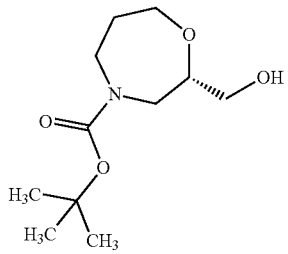 [SMILES: CC(C)(C)OC(=O)N1CCCO[C@H](CO)C1]

The product from previous experiment (approx 0.26 mol) in it's methanol solution approx 1.2 L after filtration of catalyst was treated with 54.3 g (0.25 mol) of Boc-anhydride at rt. $CO_2$ (g) started to form directly. The reaction was left over night with stirring under nitrogen.
The reaction mixture was evaporated to dryness to give a light yellow liquid, 59 g (98%). $^1$H NMR (500 MHz, MeOD): δ 1.47 (s, 9H), 1.81-1.93 (qt, J=3.51, 3.51, 6.3, 6.3, 6.3, 2H), 3.03-3.16 (ddd, J=9.5, 14.4, 21.8, 1H), 3.29-3.32 (dt, J=1.6, 1.6, 3.3, 1H), 3.32-3.41 (m, 1H), 3.43-3.56 (m, 3H), 3.56-3.71 (m, 2H), 3.78 (dd, 1H), 4.07 (tq, 1H).

vi) (2S)-4-(tert-Butoxycarbonyl)-1-oxazepane-2-carboxylic acid
tert-Butyl (2S)-2-(hydroxymethyl)-1,4-oxazepane-4-carboxylate, 52.5 g (assay 85%, 40.7 g) was dissolved in 300 mL of DCM. TEMPO, 0.5 g was dissolved 100 mL of DCM. Tetrabutylammonium hydrogensulfate, 3.88 g was dissolved in 100 mL of DCM.

The three DCM solutions were charged to a reactor and 100 mL of water was added. 350 mL of sodium hypochlorite solution, 10-15%, was pH adjusted with sodium hydrogen carbonate (liquid+solids) (approx 100 ml) to pH of approx 8-9. 58 mL of sodium bromide, 0.5 M solution, was added to the above buffered solution. The resulting water solution was added dropwise at 0° C. to the two-phase system consisting of the mixed DCM solutions and water, with high stirring. The reaction generated heat. The addition could be followed by a color change (yellow to pale yellow) that indicated when the oxidant was consumed. After 10 min the jacket was set to −5° C. to keep the inner temperature at approx. 10° C. Addition was completed in 45 min and the reaction mixture was left over night. Work up: At rt, the off white reaction mixture was pH adjusted to approx 2-3 with potassium hydrogensulfate, approx 40 g and the phases were separated, water phase was washed with DCM, 3×100 ml. The resulting DCM (800 ml) solution was evaporated to an oil, approx 100 g. The oil was dissolved in bicarbonate solution, 400 ml, and was extracted with DCM, 2×75 ml. The residual water phase was acidified to pH 2-3 with potassium hydrogen sulfate, approx 35-40 g, and was extracted with DCM (5×75 ml). The DCM was evaporated to give 40.7 g of white crystals; yield: 40.7 g, 85% yield based on the assay of the starting material. Product contained 10% water.
Purification: product was slurried in 200 mL of toluene and heated to 60° C. where it went in to solution. Approx 100 mL of toluene was evaporated off and the acid product started to crystallize at 60° C. The mixture was cooled to rt. Product was filtered off and was washed with toluene. Product was dried under reduced pressure. $^1$H NMR (600 MHz, $CDCl_3$): δ 1.46 (s, 9H), 1.93 (s, 2H), 3.23 (ddt, 1H), 3.33-3.78 (m, 3H), 3.95-4.38 (m, 3H), 9.91 (s, 1H).

Intermediate 4 tert-Butyl (2S)-2-{[(2S)-1-amino-3-(4-iodophenyl)-1-oxopropan-2-yl]carbamoyl}-1,4-oxazepane-4-carboxylate (2S)-4-(tert-Butoxycarbonyl)-1,4-oxazepane-2-carboxylic acid (Intermediate 3, 7.9 g, 32.2 mmol) and (S)-2-amino-3-(4-iodophenyl) propanamide (9.0 g, 32.2 mmol, prepared according to the procedure in WO 2009/074829, p. 45) were added to T3P (25 g, 39.3 mmol, 50% solution in DMF) in DMF (200 mL). TEA (25 mL, 180.3 mmol) was added and the reaction was stirred at rt for 4 h. After this time the reaction mixture was concentrated under reduced pressure. The resultant oil was dissolved in EtOAc and washed successively with 2 M aqueous hydrochloric acid, saturated aqueous solution of sodium hydrogen carbonate and sodium chloride solution. The organic extracts were dried (magnesium sulfate), filtered and concentrated under reduced pressure to afford the title compound as a foaming yellow oil (13.1 g, 79%) which was used without further purification.

Intermediate 5 tert-Butyl (2S)-2-{[(1S)-1-cyano-2-(4-iodophenyl) ethyl]carbamoyl}-1,4-oxazepane-4-carboxylate Burgess reagent (8.16 g, 34.27 mmol) was added to a solution of tert-butyl (2S)-2-{[(2S)-1-amino-3-(4-iodophenyl)-1-oxopropan-2-yl]carbamoyl}-1,4-oxazepane-4-carboxylate (Intermediate 4, 8.86 g, 17.13 mmol) in DCM (740 mL). The reaction mixture was stirred at rt for 24 h after which time the reaction was transferred to a separating funnel and washed with water. The organic extracts were dried (phase separator cartridge) and concentrated under reduced pressure. The resultant solid was purified by silica gel column chromatography eluting with 25% EtOAc in iso-hexane to afford a yellow oil. Trituration with diethyl ether afforded the title compound as an off-white solid (6.05 g, 71%). $^1$H NMR (400 MHz, CDCl$_3$): δ 7.66 (d, 2H), 6.98 (m, 3H), 5.06 (s, 1H), 4.22-3.92 (m, 3H), 3.70 (m, 0.5H), 3.54-3.20 (m, 2.5H), 3.09-2.89 (m, 3H), 1.88 (s, 2H), 1.42 (s, 9H).

Intermediate 6 tert-Butyl (2S)-2-[[(1S)-2-amino-2-oxo-1-[[4-(4,4,5,5-tetramethyl-1,3,2-dioxaborolan-2-yl)phenyl] methyl]ethyl] carbamoyl]-1,4-oxazepane-4-carboxylate Pin$_2$B$_2$ (0.32 g, 1.26 mmol), potassium acetate (0.28 g, 2.9 mmol) and Pd(dppf)Cl$_2$.DCM (0.039 g, 5 mol %) were added to a stirred solution of tert-butyl (2S)-2-{[(2S)-1-amino-3-(4-iodophenyl)-1-oxopropan-2-yl]carbamoyl}-1,4-oxazepane-4-carboxylate (Intermediate 4, 0.5 g, 0.97 mmol) in dry DMSO (2.5 mL) under nitrogen. The reaction was heated at 85° C. for 5 h and allowed to stand at rt overnight. Water (15 mL) was added and the mixture was extracted with EtOAc (2×50 mL). The combined extracts were washed with saturated sodium chloride (20 mL), dried (magnesium sulfate) and evaporated under reduced pressure. The resulting oil was purified by silica gel column chromatography eluting with EtOAc to give the title compound (0.3 g, 60%) as a colourless oil. $^1$H NMR (400 MHz, CDCl$_3$): δ 7.75 (d, 2H), 7.28-7.21 (m, 2H), 5.30 (s, 1H), 4.60 (m, 1H), 4.18-3.98 (m, 2H), 3.51-3.42 (m, 1H), 3.12 (t, 2H), 2.80 (s, 1H), 2.05 (s, 2H), 1.88 (s, 1H), 1.60 (s, 4H), 1.54-1.33 (m, 6H), 1.40-1.16 (m, 12H) (three exchangeable protons not observed).

EXAMPLES

Example 1

(2S)—N-[(1S)-1-Cyano-2-(4'-cyanobiphenyl-4-yl)ethyl]-1,4-oxazepane-2-carboxamide

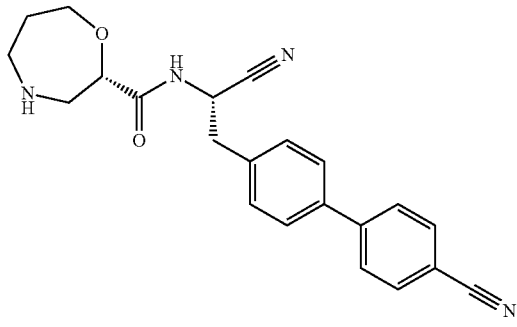 [SMILES: N#Cc1ccc(-c2ccc(C[C@@H](C#N)NC(=O)[C@@H]3CNCCCO3)cc2)cc1]

i) tert-Butyl (2S)-2-{[(1S)-1-cyano-2-(4'-cyanobiphenyl-4-yl)ethyl]carbamoyl}-1,4-oxazepane-4-carboxylate 2-Pyridinol-1-oxide (0.155 g, 1.4 mmol), TEA (0.36 g, 3.6 mmol) and 1-ethyl-3-(3-dimethylaminopropyl)carbodiimide hydrochloride (0.268 g, 1.4 mmol) were added to a solution of (2S)-4-(tert-butoxycarbonyl)-1,4-oxazepane-2-carboxylic acid (Intermediate 3, 0.294 g, 1.2 mmol) in DCM (15 mL). After 20 min 4'-[(2S)-2-amino-2-cyanoethyl]biphenyl-4-carbonitrile (Intermediate 1, 0.296 g, 1.2 mmol) was added and the mixture was stirred for 3 h and allowed to stand at rt for 18 h. The mixture was heated at 40° C. for 4 h before water (15 mL) was added. After 10 min the DCM was dried (phase separating cartridge) and evaporated under reduced pressure. The resultant yellow oil was purified by silica gel column chromatography to give the subtitled compound (0.29 g, 52%). Used without further purification in the next step.

ii) (2S)—N-[(1S)-1-Cyano-2-(4'-cyanobiphenyl-4-yl)ethyl]-1,4-oxazepane-2-carboxamide Prepared according to procedure in Method A step ii) using tert-butyl (2S)-2-{[(1S)-1-cyano-2-(4'-cyanobiphenyl-4-yl)ethyl]carbamoyl}-1,4-oxazepane-4-carboxylate to afford the title compound as a white solid (60 mg, 28%). $^1$H NMR (400 MHz, CDCl$_3$): δ 7.77-7.65 (m, 4H), 7.62-7.57 (m, 2H), 7.40 (d, 2H), 7.11 (d, 1H), 5.18-5.11 (m, 1H), 4.19-4.14 (m, 1H), 4.06-3.96 (m, 2H), 3.75-3.69 (m, 1H), 3.56-3.48 (m, 2H), 3.18-3.05 (m, 3H), 2.95-2.90 (m, 1H), 2.70 (ddd, 1H) (1 exchangeable proton not observed).

LCMS (10 cm_ESCI_Formic_MeCN) t$_R$ 2.57 (min) m/z 375 (MH$^+$).

Example 2

(2S)—N-{(1S)-1-Cyano-2-[4-(3-methyl-2-oxo-2,3-dihydro-1,3-benzoxazol-5-yl)phenyl]ethyl}-1,4-oxazepane-2-carboxamide

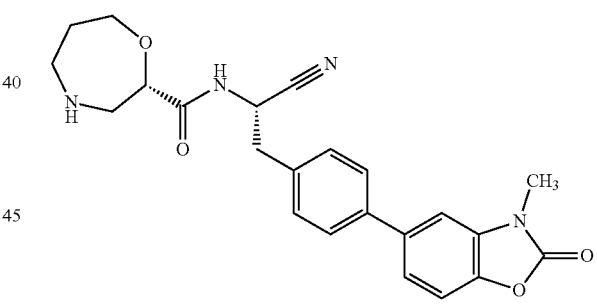

i) tert-Butyl (2S)-2-({(1S)-1-cyano-2-[4-(3-methyl-2-oxo-2,3-dihydro-1,3-benzoxazol-5-yl)phenyl]ethyl}carbamoyl)-1,4-oxazepane-4-carboxylate

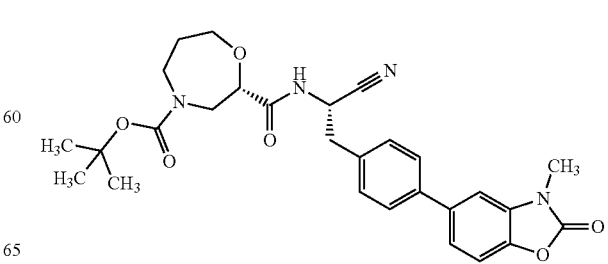

N-(3-Dimethylaminopropyl)-N'-ethylcarbodiimide hydrochloride (468 mg, 2.44 mmol) and 2-pyridinol 1-oxide (271 mg, 2.44 mmol) were added to a solution of (2S)-4-(tert-butoxycarbonyl)-1,4-oxazepane-2-carboxylic acid (Intermediate 3, 490 mg, 2.0 mmol) in DCM (15 mL). The reaction was stirred at rt for 30 min before the addition of (2S)-2-amino-3-[4-(3-methyl-2-oxo-2,3-dihydro-1,3-benzoxazol-5-yl)phenyl]propanenitrile (Intermediate 2, 586 mg, 2.0 mmol) and DiPEA (1.79 mL, 10 mmol). The reaction was stirred at rt for 18 h before transferring to a separating funnel. The mixture was washed with 2 M hydrochloric acid, saturated sodium hydrogen carbonate solution and brine. The organic extract was run through a hydrophobic frit/phase separator and concentrated under reduced pressure. The crude material was purified by silica gel column chromatography eluting with 0-60% EtOAc in iso-hexane to afford the subtitled compound as an oil (457 mg, 44%). $^1$H NMR (400 MHz, CDCl$_3$): δ 7.63-7.52 (m, 2H), 7.38 (d, 2H), 7.36-7.24 (m, 2H), 7.35-6.98 (m, 2H), 5.18 (t, 1H), 4.22-3.97 (m, 2H), 3.76-3.67 (m, 0.5H), 4.10-2.94 (m, 4.5H), 3.35-3.26 (m, 1H), 3.24-3.04 (m, 3H), 2.06-1.82 (m, 2H), 1.47 (s, 10H).

ii) (2S)—N-{(1S)-1-Cyano-2-[4-(3-methyl-2-oxo-2,3-dihydro-1,3-benzoxazol-5-yl)phenyl]ethyl}-1,4-oxazepane-2-carboxamide tert-Butyl (2S)-2-({(1S)-1-cyano-2-[4-(3-methyl-2-oxo-2,3-dihydro-1,3-benzoxazol-5-yl)phenyl]ethyl}carbamoyl)-1,4-oxazepane-4-carboxylate (457 mg, 0.85 mmol) was dissolved in formic acid (3 mL) and heated at 50° C. for 10 min on a pre-heated stirrer hotplate. After this time the reaction was concentrated under reduced pressure, dissolved in DCM and washed with saturated sodium hydrogen carbonate solution. The organic extract was run through a hydrophobic frit/phase separator and concentrated under reduced pressure. The resultant foam was purified by silica gel column chromatography eluting with 0-5% methanolic ammonia (7 N) in DCM to afford the title compound as solid material (230 mg, 64%). $^1$H NMR (400 MHz, CDCl$_3$): δ 7.59-7.51 (m, 2H), 7.39 (dd, 2H), 7.33-7.23 (m, 3H), 7.14 (d, 1H), 5.23-5.12 (m, 1H), 4.12-4.06 (m, 1H), 4.05-3.95 (m, 1H), 3.81-3.71 (m, 1H), 3.46 (s, 3H), 3.34-3.26 (m, 1H), 3.19-3.00 (m, 3H), 2.99-2.82 (m, 2H), 1.92-1.77 (m, 2H) (one exchangeable proton not observed).

LCMS (10 cm_ESCI_Formic_MeCN) t$_R$ 2.48 (min) m/z 375 (MH$^+$).

Example 2 (Alternative Synthesis (2S)—N-{(1S)-1-Cyano-2-[4-(3-methyl-2-oxo-2,3-dihydro-1,3-benzoxazol-5-yl)phenyl]ethyl}-1,4-oxazepane-2-carboxamide i) 5-Chloro-1,3-benzoxazol-2-(3H)-one

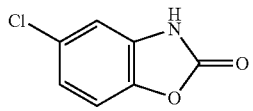 [SMILES: O=c1[nH]c2cc(Cl)ccc2o1]

To a solution of 2-amino-4-chlorophenol (400 g, 2.79 mol) in 2-MeTHF (6 L) was added CDI (497 g, 3.07 mol) under N$_2$ (exotherm 11.0° C.-22.0° C.). The reaction mixture was heated at reflux for 1 h. The mixture was cooled to rt, washed with 2 M HCl(aq) (6 L), 8% NaHCO$_3$ (aq) (6 L) and brine (3 L). The organic layer was dried over MgSO$_4$, filtered and evaporated. This gave the product as a pale brown solid (456.1 g, 97% yield, LC purity >99%). $^1$H NMR (270 MHz, DMSO-d$_6$): δ 12.0-11.5 (br s, 1H), 7.31 (d, 1H), 7.12 (m, 2H). LCMS (5 cm_ESCI, aq. formic acid_methanol) t$_R$ 3.87 (min) m/z 169.8 (MH$^+$).

ii) 5-Chloro-3-methyl-1,3-benzoxazol-2(3H)-one

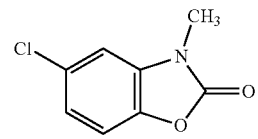

To a solution of 5-chloro-1,3-benzoxazol-2(3H)-one (stage i) (1111.8 g, 6.56 mol) in DMF (4.12 L) was added Cs$_2$CO$_3$ (2136.4 g, 6.56 mol) maintaining the temperature between 0-5° C. MeI (450 ml, 7.21 mol) was then added slowly maintaining the temperature between 0-5° C. The reaction mixture was allowed to warm-up to rt and stirred overnight. The mixture was cooled to 0-5° C. and H$_2$O (4.12 L) was added slowly. The reaction mixture was then warmed to rt and stirred for 15 min. The solids were filtered off and washed with water (4×980 ml). The filter cake was dried under vacuum at 55° C. overnight (1149.9 g, 96% yield, LC purity >99%, H$_2$O: (Karl Fischer) 0.1%). $^1$H NMR (270 MHz, DMSO-d$_6$): δ 7.45 (d, 1H), 7.35 (d, 1H), 7.15 (dd, 1H), 3.35 (s, 3H). LCMS (5 cm_ESCI_aq. formic acid_methanol) t$_R$ 4.13 (min) m/z 183.8 (M$_+$).

ii) 3-Methyl-5-(4,4,5,5-tetramethyl-1,3,2-dioxaborolan-2-yl)-1,3-benzoxazol-2(3H)-one

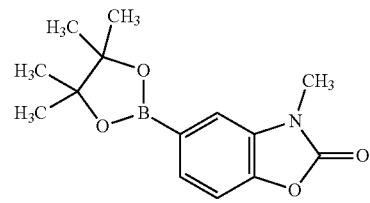 [SMILES: Cn1c(=O)oc2ccc(B3OC(C)(C)C(C)(C)O3)cc21]

A solution of 5-chloro-3-methyl-1,3-benzoxazol-2(3H)-one (stage ii)) (350 g, 1.91 mol), B$_2$pin$_2$ (581.0 g, 2.29 mol) and KOAc (561.3 g, 5.72 mol) was vacuum degassed and purged with N$_2$ (×3). Pd(OAc)$_2$ (12.9 g, 57.2 mmol) and XPhos (54.6 g, 114 mmol) were added and the mixture was vacuum degassed and purged with N$_2$ (×3). The mixture was heated to 75° C. A large exotherm was observed at ~70° C. which warmed-up the mixture to reflux (100° C.). The reaction mixture was stirred for 1 h with no heating. HPLC analysis indicated 2.5% of the starting material remaining therefore the mixture was heated at 85° C. for 1 h. At this stage, no further change was observed. Additional portions of B$_2$pin$_2$ (14.6 g, 57.2 mmol), KOAc (5.7 g, 57.2 mmol), Pd(OAc)$_2$ (12.9 g, 57.2 mmol) and XPhos (27.3 g, 57.2 mmol) were added and the mixture was stirred for 1 h at 75° C. HPLC analysis showed no starting material remaining. The mixture was cooled to rt, filtered through a pad of Celite (501 g) and the cake was washed with EtOAc (2240 ml). The filtrate was combined with two other batches prepared in the same way (2×350 g) and evaporated. This gave 1865.1 g of the product as a grey solid (97% yield, 90.0% pure by LC, 82±2% pure by 1H NMR (DMSO-$d_6$) assay vs TCNB). $^1$H NMR (270 MHz, DMSO-$d_6$): δ 7.40-7.50 (m, 2H), 7.30 (d, 1H), 3.40 (s, 3H), 1.30 (s, 12H).

LCMS (5 cm_ESCI_aq. formic acid_methanol_) $t_R$ 4.91 (min) m/z 276.1 (MH$^+$).

iv) Nα-(tert-Butoxycarbonyl)-4-(3-methyl-2-oxo-2, 3-dihydro-1,3-benzoxazol-5-yl)-L-phenylalaninamide

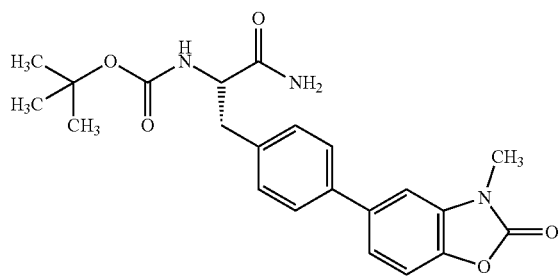

To a suspension of 5-(4,4,5,5-tetramethyl-1,3,2-dioxaborolan-2-yl)-1,3-benzoxazol-2(3H)-one (stage iii)) (859 g, 700 g active, 2.544 mol) and tert-butyl (S)-1-carbamoyl-2-(4-iodophenyl)ethylcarbamate (prepared according to the procedure in WO 2009/074829 p. 47), (903 g, 2.313 mol) in dioxane (4.1 L) was added 2 M $K_2CO_3$ (2.3 L). The suspension was vacuum degassed and purged with $N_2$ (×3). Pd(dppf)Cl$_2$-DCM (28.33 g, 0.0347 mol) was added and the reaction mixture was heated at 75° C. for 3 h. The mixture was cooled to rt and diluted with water (6.4 L). The suspension was stirred at rt overnight; the solid was filtered off and washed with water (3×1 L). The product was dried at 45° C. for 3 days (1269.1 g, yield 133%—by 1H NMR contains pinacol related impurity and dioxane, LC 94.3% pure, H$_2$O: (Karl Fischer) 3.35%). $^1$H NMR (270 MHz, DMSO-$d_6$): δ 7.62-7.34 (m, 7H), 7.04 (brs, 2H), 6.86 (d, 1H) 4.12 (m, 1H), 3.40 (s, 3H), 3.00 (dd, 1H), 2.78 (dd, 1H), 1.30 (s, 9H).

LCMS (5 cm_ESI_Water_MeCN) $t_R$ 4.51 (min) m/z 312 (MH$^+$).

v) 4-(3-Methyl-2-oxo-2,3-dihydro-1,3-benzoxazol-5-yl)-L-phenylalaninamide

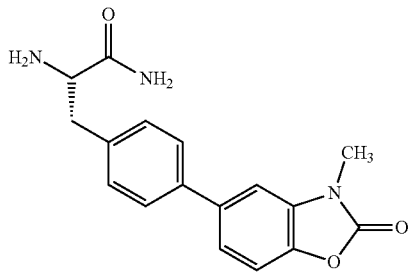

To a very thick suspension of Nα-(tert-butoxycarbonyl)-4-(3-methyl-2-oxo-2,3-dihydro-1,3-benzoxazol-5-yl)-L-phenylalaninamide (stage iv)) (1269 g, active 952 g assumed 100% conversion at stage iv), 2.3138 mol) in DCM (2.1 L) under $N_2$ was added dropwise 4.1 M HCl in dioxane (2.7 L, 11.06 mol) over 1 h maintaining the temperature at ~15° C. (suspension became more mobile after addition of approx. 0.5 L of 4.1 M HCl dioxane). After 2 h, the mixture was diluted with water (5.6 L) and stirred for 30 min at rt. The mixture was then filtered through a pad of Celite (500 g) to remove undissolved material—very slow filtration; the Celite was checked for product by LC. The pad was washed with water (400 ml). The layers DCM/dioxane-water were separated. The aqueous layer was cooled to −5° C. and 35% $NH_3$ (aq) (700 ml) was added slowly to achieve pH=9-10. The suspension was stirred overnight then the product was filtered off and washed with water (3×400 ml). The product was dried at 45° C. in vacuo for 2 days (off white solid, 489.4 g, 68% yield over two stages, 99.4% pure by LC, >99% EP, 98±2% pure by $^1$H NMR assay vs TCNB in DMSO, H$_2$O: (Karl Fischer) 0.92%). $^1$H NMR (270 MHz, DMSO-$d_6$): δ 7.59-7.30 (m, 7H), 6.98 (brs, 1H), 3.36 (m, 4H), 2.95 (dd, 1H), 2.67 (dd, 1H) 1.86 (brs, 2H).

LCMS (5 cm_ESI_Water_MeCN) $t_R$ 2.76 (min) m/z 312 (MH$^+$).

vi) tert-Butyl (2S)-2-({(1S)-1-cyano-2-[4-(3-methyl-2-oxo-2,3-dihydro-1,3-benzoxazol-5-yl)phenyl]ethyl}carbamoyl)-1,4-oxazepane-4-carboxylate

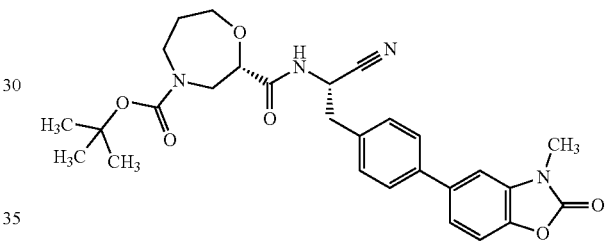

To a solution of 4-(3-methyl-2-oxo-2,3-dihydro-1,3-benzoxazol-5-yl)-L-phenylalaninamide (stage v)) (756 g, active 733 g, 2.354 mol) and (2S)-4-(tert-butoxycarbonyl)-1,4-oxazepane-2-carboxylic acid (577 g, 2.354) (Intermediate 3) in DMF (3 L) was added DiPEA (1230 ml, 7.062 mol) under $N_2$. T3P in DMF (50% w/w, 1924 ml, 3.296 mol) was added dropwise over 1.5 h maintaining the temperature <25° C. After 30 min, LC completion check indicated completion of the coupling reaction. DiPEA (1230 ml, 7.062 mol) was then added and the reaction mixture was heated to 50° C. T3P in DMF (50% w/w, 3986 ml, 6.827 mol) was added portionwise over 1 h (no exotherm observed). The reaction mixture was stirred at 50° C. for 4 h and then at rt overnight. The mixture was cooled to 10° C., diluted with 2-MeTHF (4 L) and water (5.6 L, exothermic). The layers were separated and the aqueous layer was extracted with 2-MeTHF (2×4 L). The combined organic extracts were dried over MgSO$_4$, filtered and concentrated under reduced pressure. This delivered the product as a pale brown solid in 98% yield (1242 g (active 1205 g), corrected yield 98%, LC purity 98.4%, $^1$H NMR assay vs TCNB 97±2%, main impurities by $^1$H NMR: 2-MeTHF 1.9%, DMF 0.6%).

vii) (2S)—N-{(1S)-1-Cyano-2-[4-(3-methyl-2-oxo-2,3-dihydro-1,3-benzoxazol-5-yl)phenyl]ethyl}-1,4-oxazepane-2-carboxamide A solution of tert-butyl (2S)-2-({(1S)-1-cyano-2-[4-(3-methyl-2-oxo-2,3-dihydro-1,3-benzoxazol-5-yl)phenyl]ethyl}carbamoyl)-1,4-oxazepane-4-carboxylate (stage vi)) (1776 g, active 1671 g, 3.210 mol) in formic acid/water (4.2 L/440 ml) was stirred on a buchi at 35-37° C. under reduced pressure (300-500 mbar). After 3 h, LCMS completion check indicated 93.95% of the product and 0.5% of the starting material. The mixture was concentrated (4 h) to give an oily residue. The residue was dissolved in water (4.4 L) and washed with TBME (2.2 L). The aqueous layer was vigorously stirred and treated with $NH_3$ (aq) (1.8 L) at <25° C. to achieve pH=9-10. The mixture was stirred at rt for 3 h. The solid was filtered off and washed with water (3×1 L). The filter cake was dried at 45° C. overnight. This gave the product as a pale brown solid (1498 g, active 1333 g, LC 91.5%, $^1$H NMR assay vs TCNB 89±2%, $H_2O$: (Karl Fischer) 4.63%).

The crude product was re-crystallised from EtOH/$H_2O$ in two batches (2×747 g).

Batch A: The crude product (747 g) was dissolved in EtOH (8 L) at reflux under $N_2$. Water (1.6 L) was added slowly. The mixture was hot filtered (65° C.) to remove black particles (filtrate temperature 50° C.) and then stirred at 40° C. overnight. The suspension was cooled to 10° C. over 4 h and held at that temperature for 3 h. The product was filtered off and washed with EtOH/$H_2O$ (8:2, 3×500 ml) then water (3×500 ml). The filter cake was dried at 45° C. overnight (473 g, 97.7% pure by LC, Pd level 71.4 ppm).

Batch B gave 436 g of the product (95.8% pure by LC, Pd level 65.8 ppm).

The liquors from both batches were combined and concentrated to ~8 L. The liquors were left overnight at rt. The solids were filtered off and washed with EtOH/$H_2O$ (8:2, 3×400 ml) then water (3×400 ml). The product was dried at 45° C. overnight. This gave additional 88 g of the product (LC purity 95.0%).

The products (LC purity of the blend 95.69%) were re-crystallised from EtOH/$H_2O$ in two batches (Batch C: 520 g, Batch D: 520 g).

Batch C: The crude product (520 g) was dissolved in EtOH (6.24 L) at reflux under $N_2$. Water (1248 ml) was added slowly. The mixture was allowed to cool down to 40° C. (3 h), seeded with 0.5 g of the title compound and stirred at 40° C. for 10 h. The mixture was then cooled to 26° C. over 7 h. The resulting suspension was cooled to 10° C. and stirred at that temperature for 6 h. The product was filtered off, washed with EtOH/water (8:2, 3×500 ml) and water (3×500 ml). The filter cake was dried at 45° C. for 2 d. The product was obtained as a grey solid (418 g, yield ~56%, LCMS purity 97.5%, chiral LC 100%, $^1$H NMR (DMSO-$d_6$) assay vs TCNB 100±2%).

Batch D: 418 g, yield ~56%, LCMS purity 97.5%, chiral LC 100%, $^1$H NMR (DMSO-$d_6$) assay vs TCNB 100±2%

The product was blended with the material from an intermediate scale reaction performed in the same way and re-analysed (968 g, LC purity 98.04%, chiral LC 100%, $^1$H NMR assay vs TCNB 99±2%, 0.35% EtOH by 1H NMR, $H_2O$: (Karl Fischer) 4.58%, Pd 57.6 ppm, XRPD (X-ray powder diffraction) Form A.

TABLE 1

Five peaks of highest intensity of Example 2, Form A

| °2-theta | Relative intensity |
| --- | --- |
| 12.2 | str |
| 14.3 | str |
| 16.2 | str |
| 19.1 | med |
| 20.6 | vs |

TABLE 2

Ten peaks of highest intensity of Example 2, Form A

| °2-theta | Relative intensity |
| --- | --- |
| 8.9 | w |
| 12.2 | str |
| 14.3 | str |
| 16.2 | med |
| 17.9 | vw |
| 19.1 | med |
| 20.6 | vs |
| 25.0 | w |
| 28.9 | w |
| 34.7 | w |

Example 2, Preparation of Crystalline Form B (2S)—N-{(1S)-1-Cyano-2-[4-(3-methyl-2-oxo-2,3-dihydro-1,3-benzoxazol-5-yl)phenyl]ethyl}-1,4-oxazepane-2-carboxamide, Form A (5 g), prepared by the process described above, was charged into a reaction vessel. Acetone (35 ml) was added and the mixture heated to 60-65° C. in a heating block. The resulting solution was left to cool to rt by switching the heating block off. The resulting suspension was filtered and the filtrate dried in a vacuum oven at 40° C. and <600 mbar overnight. XRPD (X-ray powder diffraction), Form B

TABLE 3

Five peaks of highest intensity of Example 2, Form B

| °2-theta | Relative intensity |
| --- | --- |
| 12.3 | str |
| 14.3 | str |
| 15.6 | vs |
| 16.3 | str |
| 17.2 | str |

TABLE 4

Ten peaks of highest intensity of Example 2, Form B

| °2-theta | Relative intensity |
| --- | --- |
| 12.3 | str |
| 14.3 | str |
| 15.6 | vs |
| 16.3 | str |

TABLE 4-continued

Ten peaks of highest intensity of Example 2, Form B

| °2-theta | Relative intensity |
| --- | --- |
| 17.2 | str |
| 18.3 | med |
| 18.5 | med |
| 19.7 | med |
| 21.2 | w |
| 23.6 | w |

Example 2, Preparation of Crystalline Form C (2S)—N-{(1S)-1-Cyano-2-[4-(3-methyl-2-oxo-2,3-dihydro-1,3-benzoxazol-5-yl)phenyl]ethyl}-1,4-oxazepane-2-carboxamide, Form A (50 mg), prepared by the process described above, was charged into a 1.5 mL scintillation vial. Propan-2-ol (1 ml) was added and the mixture placed in a orbital shaker fitted with a heating block at 500 rpm and approximately 40° C. for 1 day. The resulting suspension was filtered and the filtrate dried. XRPD (X-ray powder diffraction), Form C

TABLE 5

Five peaks of highest intensity of Example 2, Form C

| °2-theta | Relative intensity |
| --- | --- |
| 9.0 | vs |
| 14.0 | med |
| 16.0 | str |
| 16.4 | str |
| 21.0 | str |

TABLE 6

Ten peaks of highest intensity of Example 2, Form C

| °2-theta | Relative intensity |
| --- | --- |
| 7.8 | w |
| 9.0 | vs |
| 14.0 | med |
| 14.4 | med |
| 16.0 | str |
| 16.4 | vs |
| 17.9 | w |
| 18.9 | med |
| 19.6 | w |
| 21.0 | med |

Example 2, Preparation of Xinafoate Salt, Crystalline Form A (2S)—N-{(1S)-1-Cyano-2-[4-(3-methyl-2-oxo-2,3-dihydro-1,3-benzoxazol-5-yl)phenyl]ethyl}-1,4-oxazepane-2-carboxamide, Form A (100 mg), prepared by the process described above, was charged into a 1.5 mL scintillation vial. Approximately 48 mg of 1-hydroxy-2-naphthoic acid was added. Subsequently 1.5 mL of ACN and 0.03 mL of water were added and the mixture was stirred at rt for approximately 6 h using a magnetic stirring bar. The vial was closed during the stirring. The resulting suspension was centrifuged at 7500 rpm for 5 min and the supernatant removed with a pasteur pipette. The wet solid residue was dried in a vacuum oven at 30° C. and 30 mbar for approximately 60 h. XRPD (X-ray powder diffraction), xinafoate salt of Form A

TABLE 7

Five peaks of highest intensity of Example 2, xinafoate salt of crystalline Form A

| °2-theta | Relative intensity |
| --- | --- |
| 7.4 | vs |
| 12.5 | med |
| 13.0 | str |
| 15.1 | vs |
| 15.5 | str |

TABLE 8

Ten peaks of highest intensity of Example 2, xinafoate salt of crystalline Form A

| °2-theta | Relative intensity |
| --- | --- |
| 7.4 | vs |
| 10.2 | med |
| 12.5 | med |
| 13.0 | str |
| 13.6 | med |
| 14.8 | med |
| 15.1 | vs |
| 15.5 | str |
| 15.7 | med |
| 17.9 | med |

Example 2, Preparation of R-Mandalate Salt, Crystalline Form A (2S)—N-{(1S)-1-Cyano-2-[4-(3-methyl-2-oxo-2,3-dihydro-1,3-benzoxazol-5-yl)phenyl]ethyl}-1,4-oxazepane-2-carboxamide, Form A (120 mg), prepared by the process described above, was charged into a 1.5 mL scintillation vial. Approximately 45 mg of R-(−)-mandelic acid was added. Subsequently 1.5 mL of ACN and 0.04 mL of water were added and the mixture was stirred at rt for approximately 6 h using a magnetic stirring bar. The vial was closed during the stirring. The resulting suspension was centrifuged at 7500 rpm for 5 min and the supernatant removed with a pasteur pipette. The wet solid residue was dried in a vacuum oven at 30° C. and 30 mbar for approximately 60 h. XRPD (X-ray powder diffraction), R-mandelate salt of Form A.

TABLE 9

Five peaks of highest intensity of Example 2, R-mandelate salt of crystalline Form A

| °2-theta | Relative intensity |
|---|---|
| 13.0 | med |
| 14.5 | med |
| 15.5 | vs |
| 17.0 | med |
| 21.4 | med |

TABLE 10

Ten peaks of highest intensity of Example 2, R-mandelate salt of crystalline Form A

| °2-theta | Relative intensity |
|---|---|
| 8.0 | w |
| 13.0 | med |
| 14.5 | med |
| 15.5 | vs |
| 15.7 | w |
| 15.9 | med |
| 17.0 | med |
| 18.2 | w |
| 18.7 | w |
| 21.4 | med |

Example 3 (Method A (2S)—N-{(1S)-1-Cyano-2-[4-(3,7-dimethyl-2-oxo-2,3-dihydro-1,3-benzoxazol-5-yl)phenyl]ethyl}-1,4-oxazepane-2-carboxamide

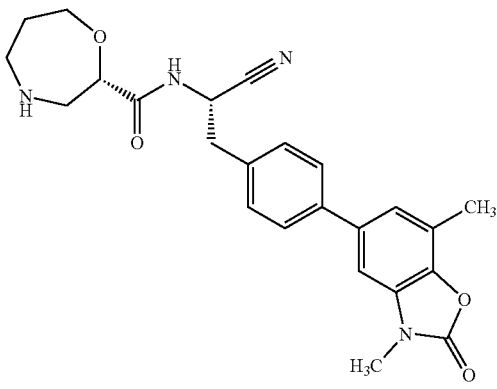 [SMILES: Cc1cc(-c2ccc(C[C@@H](C#N)NC(=O)[C@@H]3CNCCCO3)cc2)cc2c1oc(=O)n2C]

i) tert-Buty 3(2S)-2-({(1S)-1-cyano-2-[4-(3,7-dimethyl-2-oxo-2,3-dihydro-1,3-benzoxazol-5-yl)phenyl]ethyl}carbamoyl)-1,4-oxazepane-4-carboxylate 5-(5,5-Dimethyl-1,3,2-dioxaborinan-2-yl)-3,7-dimethyl-1,3-benzoxazol-2(3H)-one (Boronate ester 1, 154 mg, 0.56 mmol) and tert-butyl (2S)-2-{[(1S)-1-cyano-2-(4-iodophenyl)ethyl]carbamoyl}-1,4-oxazepane-4-carboxylate (Intermediate 5, 266 mg, 0.53 mmol) were dissolved in ACN (13 mL) and water (0.5 mL). Potassium carbonate (110 mg, 0.80 mmol) was added and the reaction mixture was degassed for 20 min before the addition of Pd(dppf)Cl$_2$.DCM (43 mg, 0.053 mmol). The reaction mixture was heated at 80° C. for 90 min. After this time the reaction was concentrated under reduced pressure and purified by silica gel column chromatography eluting with a gradient of 0-80% EtOAc in isohexane to afford the subtitled compound as a light brown solid (242 mg, 85%). $^1$H NMR (400 MHz, CDCl$_3$): δ 7.55 (d, 2H), 7.36 (d, 2H), 7.16-7.02 (m, 3H), 6.96 (s, 1H), 5.16 (s, 1H), 4.17-4.00 (m, 3H), 3.56-3.48 (m, 1H), 3.53-3.36 (m, 3H), 3.21-3.12 (m, 2H), 2.44 (s, 3H), 1.95 (d, 2H), 1.47 (s, 9H), 0.94-0.87 (m, 2H).

ii) (2S)—N-{(1S)-1-Cyano-2-[4-(3,7-dimethyl-2-oxo-2,3-dihydro-1,3-benzoxazol-5-yl)phenyl]ethyl}-1,4-oxazepane-2-carboxamide tert-Butyl (2S)-2-({(1S)-1-cyano-2-[4-(3,7-dimethyl-2-oxo-2,3-dihydro-1,3-benzoxazol-5-yl)phenyl]ethyl}carbamoyl)-1,4-oxazepane-4-carboxylate (240 mg, 0.45 mmol) was dissolved in formic acid (3 mL) and heated at 50° C. for 10 min on a pre-heated stirrer hotplate. After this time the reaction was concentrated under reduced pressure, dissolved in DCM and washed with saturated sodium hydrogen carbonate solution. The organic extract was dried (phase separator cartridge) and concentrated under reduced pressure. The solid was purified by silica gel column chromatography eluting with 0-2% methanolic ammonia (7 N) in DCM to afford the title compound as a white solid (54 mg, 27%).

1H NMR (400 MHz, DMSO-d$_6$): δ 8.62 (d, 1H), 7.65 (d, 2H), 7.38 (d, 3H), 7.28 (s, 1H), 5.03 (q, 1H), 4.00 (dd, 1H), 3.90-3.82 (m, 1H), 3.73 (ddd, 1H), 3.39 (s, 3H), 3.32 (s, 3H), 3.24-3.13 (m, 2H), 3.04 (dd, 1H), 2.82-2.74 (m, 1H), 2.38 (s, 2H), 1.80-1.68 (m, 2H) (one exchangeable proton not observed).

LCMS (10 cm_ESCI_Formic_MeCN) t$_R$ 2.58 (min) m/z 435 (MH$^+$).

Example 4 (Method B

4'-[(2S)-2-Cyano-2-{[(2S)-1,4-oxazepan-2-ylcarbonyl]amino}ethyl]biphenyl-3-yl methanesulfonate

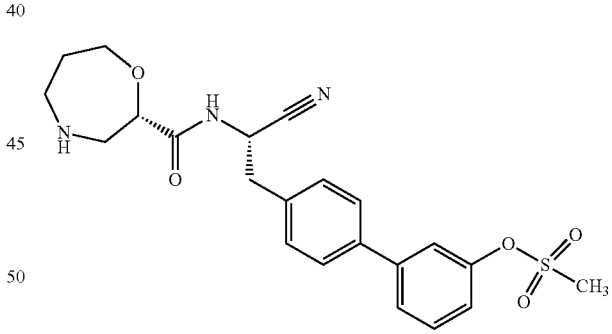

i) tert-Butyl (2S)-2-{[(2S)-1-amino-3-{3'-[(methylsulfonyl)oxy]biphenyl-4-yl}-1-oxopropan-2-yl]carbamoyl}-1,4-oxazepane-4-carboxylate A suspension of tert-butyl (2S)-2-[[(1S)-2-amino-2-oxo-1-[[4-(4,4,5,5-tetramethyl-1,3,2-dioxaborolan-2-yl)phenyl]methyl]ethyl] carbamoyl]-1,4-oxazepane-4-carboxylate tert-butyl 2-({(2S)-1-amino-1-oxo-3-[4-(4,4,5,5-tetramethyl-1,3,2-dioxaborolan-2-yl)phenyl]propan-2-yl}carbamoyl)-1,4-oxazepane-4-carboxylate (Intermediate 6, 0.21 g, 0.4 mmol), (3-iodophenyl) methanesulfonate (0.13 g, 0.44 mmol) and potassium carbonate (0.16 g, 1.2 mmol) in ACN (30 mL) and water (1.2 mL) were degassed under nitrogen for 10 min. Pd(dppf)Cl$_2$.DCM complex (0.032 g, 10 mol %) was added and the reaction mixture was heated at 80° C. for 120 min. The solvent was removed under reduced pressure and the residue was treated with water (20 mL) and DCM (25 mL). The DCM was dried (phase separating cartridge) and evaporated under reduced pressure to give the subtitled compound as a dark brown glass (0.24 g, >100%). $^1$H NMR (400 MHz, CDCl$_3$): δ 7.54-7.43 (m, 5H), 7.35-7.19 (m, 3H), 5.58 (m, 1H), 4.71 (s, 1H), 4.21-3.94 (m, 3H), 3.81-3.76 (m, 1H), 3.52-3.44 (m, 3H), 3.23-3.14 (m, 4H), 2.80 (s, 1H), 2.20-1.54 (m, 1H), 1.45 (s, 9H) (three exchangeable protons not observed).

ii) tert-Butyl (2S)-2-{[(1S)-1-cyano-2-{3'-[(methylsulfonyl)oxy]biphenyl-4-yl}ethyl]carbamoyl}-1,4-oxazepane-4-carboxylate Burgess reagent (0.11 g, 0.046 mmol) was added to a stirred solution of tert-butyl (2S)-2-{[(2S)-1-amino-3-{3'-[(methylsulfonyl)oxy]biphenyl-4-yl}-1-oxopropan-2-yl]carbamoyl}-1,4-oxazepane-4-carboxylate (0.24 g) in DCM (20 mL). After 3 days additional reagent (0.11 g, 0.046 mmol) was added and stirring was continued for 6 h. The reaction was allowed to stand overnight before washing with water (20 mL). The organic extract was dried (phase separating cartridge) and evaporated under reduced pressure. The residue was purified by silica gel column chromatography eluting with 0-100% EtOAc in iso-hexane to give the subtitled compound as a colourless glass (0.18 g, 83% over two steps). $^1$H NMR (400 MHz, CDCl$_3$): δ 7.61-7.45 (m, 5H), 7.38 (m, 3H), 7.06 (s, 1H), 5.17 (s, 1H), 4.20-3.99 (m, 2H), 3.75-3.63 (m, 1H), 3.57-3.37 (m, 3H), 3.49-2.85 (m, 3H), 1.94 (s, 2H), 1.57 (s, 1H), 1.51-1.35 (m, 9H), 1.33 (s, 1H) (one exchangeable proton not observed).

iii) 4'-[(2)-2-Cyano-2-{[(2S)-1,4-oxazepan-2-ylcarbonyl]amino}ethyl]biphenyl-3-yl methanesulfonate A solution of tert-butyl (2S)-2-{[(1S)-1-cyano-2-{3'-[(methylsulfonyl)oxy]biphenyl-4-yl}ethyl]carbamoyl}-1,4-oxazepane-4-carboxylate (0.18 g, 0.33 mmol) in formic acid (3 mL) was heated at 50° C. for 15 min. The mixture was evaporated under reduced pressure. The residue was dissolved in DCM (20 mL) and stirred with saturated sodium bicarbonate (30 mL). The layers were separated and the organic extract was dried (phase separating cartridge) and evaporated under reduced pressure. The residue was purified by silica gel column chromatography eluting with 2% 7 N methanolic ammonia in DCM. The resultant solid which was recrystallized from 1:1 di-isopropyl ether:EtOAc to afford the title compound as a colourless solid (50 mg, 34%). $^1$H NMR (400 MHz, CDCl$_3$): δ 7.61-7.46 (m, 5H), 7.40 (dd, 2H), 7.38-7.18 (m, 1H), 7.18 (d, 1H), 5.23-5.12 (m, 1H), 4.12-4.06 (m, 1H), 4.05-3.95 (m, 1H), 3.81-3.71 (m, 1H), 3.35-3.26 (m, 1H), 3.22-3.09 (m, 4H), 3.07-2.81 (m, 3H), 1.91-1.77 (m, 2H) (two exchangeable protons not observed).

LCMS (10 cm_ESCI_Bicarb_MeCN) t$_R$ 2.75 (min) m/z 444 (MH$^+$).

Examples 5-33

The following compounds were prepared in using the aforementioned methods and intermediates:

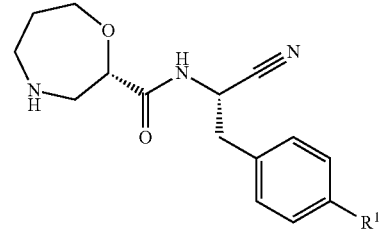

Example 5
(2S)-N-{(1S)-1-Cyano-2-[4-(3-methyl-1,2-benzoxazol-5-yl)phenyl]ethyl}-1,4-oxazepane-2-carboxamide Prepared using Method A
Boronate ester: Commercial
Intermediate: 5

R$^1$ = 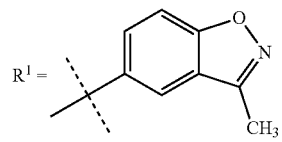

$^1$H NMR (400 MHz, CDCl$_3$): δ 7.79-7.75 (m, 2H), 7.63-7.58 (m, 3H), 7.43 (d, 2H), 7.20 (d, 1H), 5.21 (dt, 1H), 4.10 (dd, 1H), 3.99 (dt, 1H), 3.76 (ddd, 1H), 3.32 (dd, 1H), 3.20-3.12 (m, 2H), 3.05 (dd, 1H), 2.96 (dt, 1H), 2.91-2.82 (m, 1H), 2.63 (s, 3H), 1.91-1.77 (m, 2H) (one exchangeable proton not observed). m/z: 405

Example 6
(2S)-N-{(1S)-1-Cyano-2-[4'-(trifluoromethyl)biphenyl-4-yl]ethyl}-1,4-oxazepane-2-carboxamide Prepared using Method A
Boronate ester: Commercial
Intermediate: 5

R$^1$ = 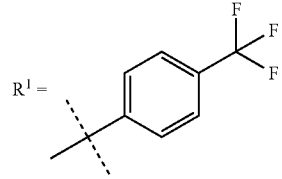

$^1$H NMR (400 MHz, CDCl$_3$): δ 7.74-7.64 (m, 4H), 7.62-7.55 (m, 2H), 7.43 (d, 2H), 7.20 (d, 1H), 5.21 (dt, 1H), 4.09 (dd, 1H), 3.98 (dt, 1H), 3.75 (ddd, 1H), 3.30 (dd, 1H), 3.16 (d, 2H), 3.07-2.80 (m, 3H), 1.92-1.76 (m, 2H) (one exchangeable proton not observed). m/z: 418

Example 7
(2S)-N-[(1S)-1-Cyano-2-(3',4'-difluorobiphenyl-4-yl)ethyl]-1,4-oxazepane-2-carboxamide Prepared using Method A
Boronate ester: Commercial
Intermediate: 5

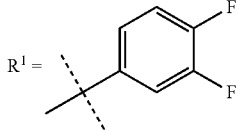

$^1$H NMR (400 MHz, CDCl$_3$): δ 7.54-7.49 (m, 2H), 7.41-7.34 (m, 3H), 7.48-7.05 (m, 3H), 5.23-5.16 (m, 1H), 4.09 (dd, 1H), 4.03-3.95 (m, 1H), 3.75 (ddd, 1H), 3.30 (dd, 1H), 3.18-3.10 (m, 2H), 3.04 (dd, 1H), 3.00-2.90 (m, 1H), 2.92-2.82 (m, 1H), 1.88-1.78 (m, 2H) (one exchangeable proton not observed). m/z: 386

Example 8
(2S)-N-{(1S)-1-Cyano-2-[4-(6-cyanopyridin-3-yl)phenyl]ethyl}-1,4-oxazepane-2-carboxamide Prepared using Method A
Boronate ester: Commercial
Intermediate: 5

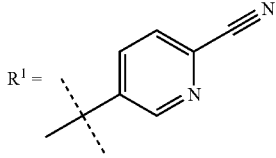

$^1$H NMR (400 MHz, DMSO-d$_6$): δ 9.10 (dd, 1H), 8.64 (d, 1H), 8.38-8.33 (m, 1H), 8.15-8.08 (m, 1H), 7.81 (t, 2H), 7.48 (d, 2H), 5.10-5.01 (m, 1H), 4.00 (dd, 1H), 3.85 (ddd, 1H), 3.76-3.67 (m, 1H), 3.33-3.18 (m, 3H), 3.02 (dd, 1H), 2.81-2.70 (m, 1H), 2.64-2.55 (m, 1H), 1.78-1.65 (m, 2H) (one exchangeable proton not observed). m/z: 376

Example 9
(2S)-N-{(1S)-1-Cyano-2-[4-(4-methyl-3-oxo-3,4-dihydro-2H-1,4-benzothiazin-6-yl)phenyl]ethyl}-1,4-oxazepane-2-carboxamide Prepared using Method A
Boronate ester: 20
Intermediate: 5

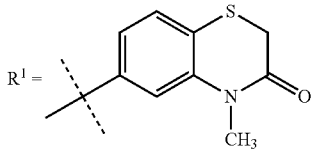

$^1$H NMR (400 MHz, CDCl$_3$): δ 7.60-7.53 (m, 2H), 7.46-7.37 (m, 3H), 7.28-7.23 (m, 2H), 7.22 (d, 1H), 5.23-5.16 (m, 1H), 4.10 (dd, 1H), 4.03-3.95 (m, 1H), 3.75 (ddd, 1H), 3.51 (s, 3H), 3.45 (s, 2H), 3.31 (dd, 1H), 3.19-3.11 (m, 2H), 3.04 (dd, 1H), 3.01-2.91 (m, 1H), 2.92-2.82 (m, 1H), 1.89-1.78 (m, 2H) (one exchangeable proton not observed). m/z: 451

Example 10
(2S)-N-{(1S)-1-Cyano-2-[4-(3-ethyl-7-methyl-2-oxo-2,3-dihydro-1,3-benzoxazol-5-yl)phenyl]ethyl}-1,4-oxazepane-2-carboxamide Prepared using Method A
Boronate ester: 4
Intermediate: 5

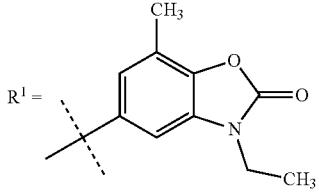

$^1$H NMR (400 MHz, CDCl$_3$): δ 7.53 (t, 2H), 7.40 (d, 2H), 7.19 (d, 1H), 7.12 (s, 1H), 6.99-6.96 (m, 1H), 5.19 (dt, 1H), 4.10 (dd, 1H), 4.04-3.90 (m, 3H), 3.75 (ddd, 1H), 3.32 (dd, 1H), 3.16-3.10 (m, 2H), 3.04 (dd, 1H), 2.96 (dt, 1H), 2.92-2.84 (m, 1H), 2.44 (s, 3H), 1.89-1.78 (m, 2H), 1.41 (t, 3H) (one exchangeable proton not observed). m/z: 449

Example 11
(2S)-N-[(1S)-1-Cyano-2-{4-[3-(2-hydroxy-2-methylpropyl)-2-oxo-2,3-dihydro-1,3-benzoxazol-5-yl]phenyl}ethyl]-1,4-oxazepane-2-carboxamide Prepared using Method A
Boronate ester: 5
Intermediate: 5

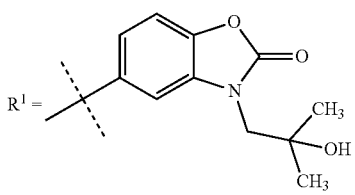

¹H NMR (400 MHz, CDCl₃): δ 7.53-7.46 (m, 2H), 7.39-7.34 (m, 3H), 7.20-7.11 (m, 3H), 5.21-5.14 (m, 1H), 4.12-4.07 (m, 1H), 4.02-3.94 (m, 3H), 3.75 (ddd, 1H), 3.31 (dd, 1H), 3.15-3.10 (m, 2H), 3.03 (dd, 1H), 2.99-2.91 (m, 1H), 2.91-2.82 (m, 1H), 1.90-1.78 (m, 2H), 1.63 (s, 6H) (two exchangeable protons not observed). m/z: 479

Example 12
(2S)-N-[(1S)-1-Cyano-2-{4-[3-(2,2-difluoroethyl)-7-fluoro-2-oxo-2,3-dihydro-1,3-benzoxazol-5-yl]phenyl}ethyl]-1,4-oxazepane-2-carboxamide Prepared using Method A
Boronate ester: 7
Intermediate: 5

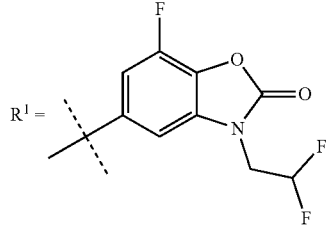

¹H NMR (400 MHz, DMSO-d₆): δ 8.62 (d, 1H), 7.69 (d, 2H), 7.60 (s, 1H), 7.48 (dd, 1H), 7.42 (d, 2H), 6.59-6.29 (m, 1H), 5.04 (q, 1H), 4.42 (td, 2H), 4.00 (dd, 1H), 3.85 (ddd, 1H), 3.72 (ddd, 1H), 3.27-3.15 (m, 2H), 3.03 (dd, 1H), 2.81-2.73 (m, 1H), 2.64-2.51 (m, 2H), 1.78-1.68 (m, 2H) (one exchangeable proton not observed). m/z: 489

Example 13
(2S)-N-[(1S)-1-Cyano-2-(4-{3-[2-(dimethylamino)ethyl]-2-oxo-2,3-dihydro-1,3-benzoxazol-5-yl}phenyl)ethyl]-1,4-oxazepane-2-carboxamide Prepared using Method A
Boronate ester: 8
Intermediate: 5

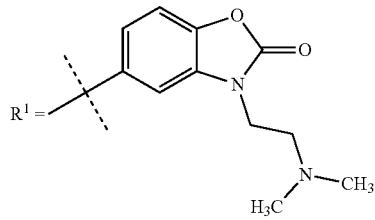

¹H NMR (400 MHz, CDCl₃): δ 7.57-7.50 (m, 2H), 7.44-7.36 (m, 2H), 7.33-7.22 (m, 2H), 7.22-7.15 (m, 2H), 5.20 (dt, 1H), 4.12-4.07 (m, 1H), 4.03-3.94 (m, 3H), 3.75 (ddd, 1H), 3.35-3.28 (m, 1H), 3.17-3.12 (m, 2H), 3.05 (dd, 1H), 3.00-2.92 (m, 1H), 2.92-2.84 (m, 1H), 2.71 (t, 2H), 2.33 (s, 6H), 1.89-1.78 (m, 2H) (one exchangeable proton not observed). m/z: 478

Example 14
(2S)-N-{(1S)-1-Cyano-2-[4-(3,3-difluoro-1-methyl-2-oxo-2,3-dihydro-1H-indol-6-yl)phenyl]ethyl}-1,4-oxazepane-2-carboxamide Prepared using Method A
Boronate ester: 9
Intermediate: 5

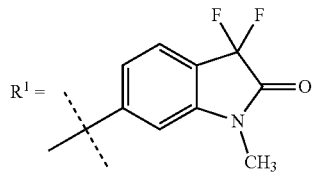

¹H NMR (400 MHz, CDCl₃): δ 7.60 (dd, 3H), 7.44 (d, 2H), 7.36 (d, 1H), 7.20 (d, 1H), 7.06 (s, 1H), 5.21 (dd, 1H), 4.11 (dd, 1H), 4.00 (dt, 1H), 3.79-3.74 (m, 1H), 3.36-3.26 (m, 4H), 3.16 (d, 2H), 3.05 (dd, 1H), 2.97-2.86 (m, 2H), 1.86-1.80 (m, 2H) (one exchangeable proton not observed). m/z: 455

Example 15
(2S)-N-{(1S)-1-Cyano-2-[4-(7-fluoro-3-methyl-2-oxo-2,3-dihydro-1,3-benzoxazol-5-yl)phenyl]ethyl}-1,4-oxazepane-2-carboxamide Prepared using Method A
Boronate ester: 6
Intermediate: 5

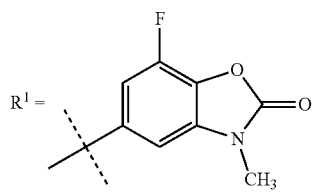

¹H NMR (400 MHz, DMSO-d₆): δ 8.62 (d, 1H), 7.71 (d, 2H), 7.49 (s, 1H), 7.42 (t, 3H), 5.04 (q, 1H), 4.00 (d, 1H), 3.89-3.82 (m, 1H), 3.73 (d, 1H), 3.39-3.10 (m, 4H), 3.03 (d, 1H), 2.81-2.73 (m, 1H), 2.65-2.53 (m, 2H), 2.22 (s, 1H), 1.73 (s, 2H) (one exchangeable proton not observed). m/z: 439

Example 16
(2S)-N-{(1S)-1-Cyano-2-[4-(3-ethyl-2-oxo-2,3-dihydro-1,3-benzoxazol-5-yl)phenyl]ethyl}-1,4-oxazepane-2-carboxamide Prepared using Method A
Boronate ester: 3
Intermediate: 5

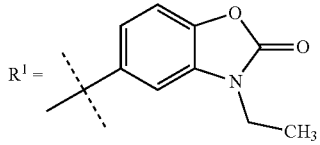

$^1$H NMR (400 MHz, CDCl$_3$): δ 7.58-7.51 (m, 2H), 7.41 (d, 2H), 7.33-7.26 (m, 2H), 7.20 (d, 1H), 7.15 (d, 1H), 5.20 (dt, 1H), 4.10 (dd, 1H), 4.04-3.90 (m, 3H), 3.75 (ddd, 1H), 3.31 (dd, 1H), 3.20-3.10 (m, 2H), 3.04 (dd, 1H), 2.96 (dt, 1H), 2.91-2.82 (m, 1H), 1.92-1.77 (m, 2H), 1.42 (t, 3H) (one exchangeable proton not observed). m/z: 435

Example 17
(2S)-N-[(1S)-1-Cyano-2-{4-[3-(cyclopropylmethyl)-2-oxo-2,3-dihydro-1,3-benzoxazol-5-yl]phenyl}ethyl]-1,4-oxazepane-2-carboxamide Prepared using Method A
Boronate ester: 10
Intermediate: 5

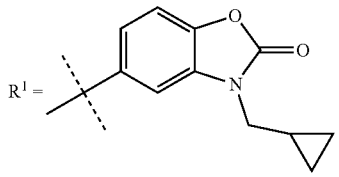

$^1$H NMR (400 MHz, CDCl$_3$): δ 7.57-7.50 (m, 2H), 7.42-7.33 (m, 2H), 7.35-7.25 (m, 4H), 5.20 (dt, 1H), 4.10 (dd, 1H), 3.99 (dt, 1H), 3.79-3.70 (m, 3H), 3.31 (dd, 1H), 3.20-3.12 (m, 2H), 3.05 (dd, 1H), 2.96 (dt, 1H), 2.91-2.82 (m, 1H), 1.91-1.77 (m, 2H), 1.33-1.23 (m, 1H), 0.66-0.59 (m, 2H), 0.50-0.44 (m, 2H) (one exchangeable proton not observed). m/z: 461

Example 18
(2S)-N-[(1S)-1-Cyano-2-{4-[3-(2-methoxyethyl)-2-oxo-2,3-dihydro-1,3-benzothiazol-5-yl]phenyl}ethyl]-1,4-oxazepane-2-carboxamide Prepared using Method A
Boronate ester: 11
Intermediate: 5

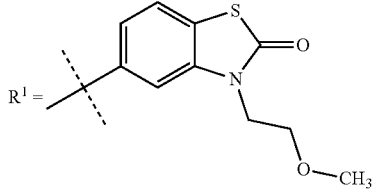

$^1$H NMR (400 MHz, CDCl$_3$): δ 7.58 (d, 2H), 7.48 (d, 1H), 7.43-7.32 (m, 4H), 7.21 (d, 1H), 5.21 (dt, 1H), 4.19 (t, 2H), 4.10 (dd, 1H), 3.99 (dt, 1H), 3.80-3.70 (m, 3H), 3.43-3.21 (m, 4H), 3.23-3.09 (m, 2H), 3.05 (dd, 1H), 3.00-2.82 (m, 2H), 1.93-1.77 (m, 2H) (one exchangeable proton not observed). m/z: 481

Example 19
(2S)-N-[(1S)-1-Cyano-2-{4-[2-oxo-3-(propan-2-yl)-2,3-dihydro-1,3-benzoxazol-5-yl]phenyl}ethyl]-1,4-oxazepane-2-carboxamide Prepared using Method A
Boronate ester: 12
Intermediate: 5

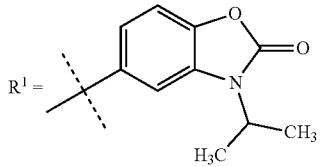

$^1$H NMR (400 MHz, CDCl$_3$): δ 7.61-7.51 (m, 2H), 7.40 (dd, 2H), 7.30-7.24 (m, 3H), 7.21 (d, 1H), 5.24-5.14 (m, 1H), 4.65-4.55 (m, 1H), 4.13-4.07 (m, 1H), 4.05-3.95 (m, 1H), 3.82-3.72 (m, 1H), 3.36-3.27 (m, 1H), 3.19-3.11 (m, 2H), 3.05 (dd, 1H), 2.99-2.82 (m, 2H), 1.93-1.76 (m, 2H), 1.59 (d, 6H) (one exchangeable proton not observed). m/z: 449

Example 20
(2S)-N-{(1S)-1-Cyano-2-[4-(4-methyl-3-oxo-3,4-dihydro-2H-1,4-benzoxazin-6-yl)phenyl]ethyl}-1,4-oxazepane-2-carboxamide -continued Prepared using Method A
Boronate ester: 13
Intermediate: 5

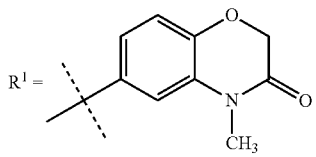

¹H NMR (400 MHz, DMSO-d₆): δ 7.54 (d, 2H), 7.43-7.33 (m, 2H), 7.24-7.18 (m, 2H), 7.15 (d, 1H), 7.06 (d, 1H), 5.23-5.13 (m, 1H), 4.66 (s, 2H), 4.12-4.06 (m, 1H), 4.05-3.95 (m, 1H), 3.81-3.71 (m, 1H), 3.43 (s, 3H), 3.37-3.28 (m, 1H), 3.17-3.10 (m, 2H), 3.09-2.99 (m, 1H), 2.99-2.82 (m, 2H), 1.93-1.77 (m, 2H) (one exchangeable proton not observed) m/z: 435

Example 21
(2S)-N-[(1S)-1-Cyano-2-{4-[3-(2-methoxyethyl)-2-oxo-2,3-dihydro-1,3-benzoxazol-5-yl]phenyl}ethyl]-1,4-oxazepane-2-carboxamide Prepared using Method A
Boronate ester: 21
Intermediate: 5

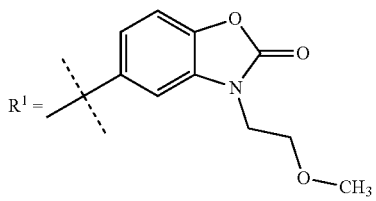

¹H NMR (400 MHz, CDCl₃): δ 7.60-7.51 (m, 2H), 7.39 (dd, 2H), 7.34-7.24 (m, 3H), 7.20 (d, 1H), 5.23-5.14 (m, 1H), 4.12-3.95 (m, 4H), 3.81-3.70 (m, 3H), 3.43-3.20 (m, 4H), 3.19-3.10 (m, 2H), 3.04 (dd, 1H), 2.99-2.82 (m, 2H), 1.92-1.77 (m, 2H) (one exchangeable proton not observed). m/z: 465

Example 22
(2S)-N-{(1S)-1-Cyano-2-[4-(5-cyanothiophen-2-yl)phenyl]ethyl}-1,4-oxazepane-2-carboxamide Prepared using Method A
Boronate ester: Commercial
Intermediate: 5

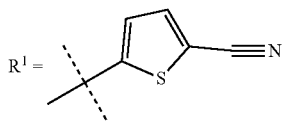

¹H NMR (400 MHz, CDCl₃): δ 7.61-7.56 (m, 3H), 7.40 (d, 2H), 7.31-7.25 (m, 1H), 7.20 (d, 1H), 5.19 (dt, 1H), 4.09 (dd, 1H), 3.99 (dt, 1H), 3.75 (ddd, 1H), 3.30 (dd, 1H), 3.13 (d, 2H), 3.07-2.81 (m, 3H), 1.91-1.76 (m, 2H) (one exchangeable proton not observed). m/z: 381

Example 23
(2S)-N-[(1S)-2-(4'-Carbamoyl-3'-fluorobiphenyl-4-yl)-1-cyanoethyl]-1,4-oxazepane-2-carboxamide Prepared using Method A
Boronate ester: Commercial
Intermediate: 5

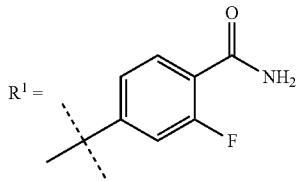

¹H NMR (400 MHz, DMSO-d₆): δ 8.65-8.58 (m, 1H), 7.78-7.69 (m, 4H), 7.67-7.55 (m, 3H), 7.41 (d, 2H), 5.09-4.99 (m, 1H), 3.99 (dd, 1H), 3.84 (ddd, 1H), 3.76-3.67 (m, 1H), 3.29-3.15 (m, 2H), 3.02 (dd, 1H), 2.80-2.68 (m, 1H), 2.63-2.49 (m, 2H), 1.79-1.64 (m, 2H) (one exchangeable proton not observed). m/z: 411

Example 24
(2S)-N-{(1S)-1-Cyano-2-[4-(1-methyl-2-oxo-1,2-dihydroquinolin-7-yl)phenyl]ethyl}-1,4-oxazepane-2-carboxamide Prepared using Method A
Boronate ester: 14
Intermediate: 5

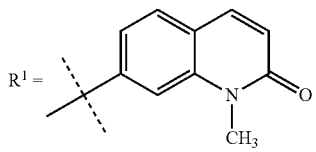

¹H NMR (400 MHz, CDCl₃): δ 7.71 (d, 1H), 7.68-7.60 (m, 3H), 7.52 (s, 1H), 7.45 (dd, 3H), 7.21 (d, 1H), 6.73 (d, 1H), 5.25-5.18 (m, 1H), 4.10 (dd, 1H), 4.04-3.96 (m, 1H), 3.83-3.69 (m, 4H), 3.32 (dd, 1H), 3.19-3.15 (m, 2H), 3.05 (dd, 1H), 3.00-2.92 (m, 1H), 2.91-2.83 (m, 1H) 1.89-1.78 (m, 2H), (one exchangeable proton not observed). m/z: 431

Example 25
(2S)-N-[(1S)-1-Cyano-2-{4-[2-oxo-3-(tetrahydro-2H-pyran-4-ylmethyl)-2,3-dihydro-1,3-benzoxazol-5-yl]phenyl}ethyl]-1,4-oxazepane-2-carboxamide Prepared using Method A
Boronate ester: 15
Intermediate: 5

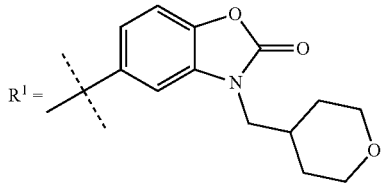

$^1$H NMR (400 MHz, CDCl$_3$): δ 7.53 (t, 2H), 7.42 (d, 2H), 7.33-7.26 (m, 2H), 7.21 (d, 1H), 7.12 (d, 1H), 5.23-5.16 (m, 1H), 4.10 (dd, 1H), 4.03-3.96 (m, 3H), 3.80-3.72 (m, 3H), 3.40-3.27 (m, 3H), 3.17-3.13 (m, 2H), 3.07-2.83 (m, 3H), 2.19 (ddd, 1H), 1.90-1.79 (m, 2H), 1.54-1.42 (m, 3H), (one proton under water peak and one exchangeable proton not observed). m/z: 505

Example 26
(2S)-N-{(1S)-2-[4-(7-Chloro-3-methyl-2-oxo-2,3-dihydro-1,3-benzoxazol-5-yl)phenyl]-1-cyanoethyl}-1,4-oxazepane-2-carboxamide Prepared using Method A
Boronate ester: 16
Intermediate: 5

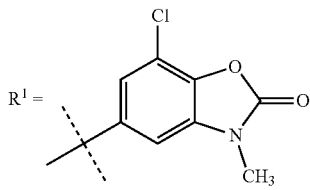

$^1$H NMR (400 MHz, CDCl$_3$): δ 7.56-7.52 (m, 2H), 7.42 (d, 2H), 7.31 (d, 1H), 7.19 (d, 1H), 7.03 (d, 1H), 5.20 (dt, 1H), 4.10 (dd, 1H), 4.00 (dt, 1H), 3.76 (ddd, 1H), 3.46 (s, 3H), 3.31 (dd, 1H), 3.16-3.12 (m, 2H), 3.04 (dd, 1H), 3.00-2.84 (m, 2H), 1.89-1.80 (m, 2H), 1.25 (s, 1H). m/z: 455

Example 27
(2S)-N-[(1S)-1-Cyano-2-{4-[3-(2,2-difluoroethyl)-2-oxo-2,3-dihydro-1,3-benzoxazol-5-yl]phenyl}ethyl]-1,4-oxazepane-2-carboxamide Prepared using Method A
Boronate ester: 17
Intermediate: 5

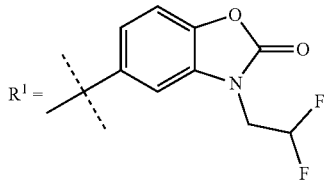

$^1$H NMR (400 MHz, CDCl$_3$): δ 7.54 (d, 2H), 7.41 (d, 2H), 7.36 (dd, 1H), 7.30 (d, 1H), 7.24 (s, 1H), 7.19 (d, 1H), 6.28-5.95 (m, 1H), 5.23-5.16 (m, 1H), 4.28-4.17 (m, 2H), 4.10 (dd, 1H), 4.03-3.95 (m, 1H), 3.75 (ddd, 1H), 3.31 (dd, 1H), 3.20-3.12 (m, 2H), 3.04 (dd, 1H), 3.00-2.82 (m, 2H), 1.91-1.77 (m, 2H) (one exchangeable proton not observed). m/z: 471

Example 28
(2S)-N-[(1S)-1-Cyano-2-{4-[2-oxo-3-(2,2,2-trifluoroethyl)-2,3-dihydro-1,3-benzoxazol-5-yl]phenyl}ethyl]-1,4-oxazepane-2-carboxamide Prepared using Method A
Boronate ester: 18
Intermediate: 5

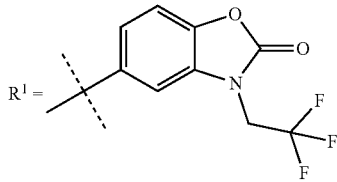

$^1$H NMR (400 MHz, CDCl$_3$): δ 7.56-7.49 (m, 2H), 7.45-7.29 (m, 4H), 7.24-7.15 (m, 2H), 5.23-5.16 (m, 1H), 4.47 (q, 2H), 4.10 (dd, 1H), 4.03-3.95 (m, 1H), 3.75 (ddd, 1H), 3.31 (dd, 1H), 3.20-3.12 (m, 2H), 3.04 (dd, 1H), 3.00-2.82 (m, 2H), 1.90-1.77 (m, 2H) (one exchangeable proton not observed). m/z: 489

Example 29
(2S)-N-{(1S)-1-Cyano-2-[4-(3-methyl-2-oxo-2,3-dihydro-1,3-benzothiazol-5-yl)phenyl]ethyl}-1,4-oxazepane-2-carboxamide Prepared using Method A
Boronate ester: 19
Intermediate: 5

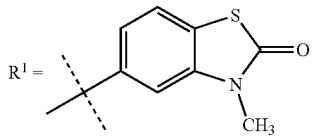

¹H NMR (400 MHz, CDCl₃): δ 7.59 (d, 2H), 7.53-7.48 (m, 1H), 7.44-7.35 (m, 3H), 7.22-7.17 (m, 2H), 5.21 (dt, 1H), 4.10 (dd, 1H), 3.99 (dt, 1H), 3.76 (ddd, 1H), 3.52 (s, 3H), 3.31 (dd, 1H), 3.17-3.12 (m, 2H), 3.05 (dd, 1H), 2.99-2.92 (m, 1H), 2.91-2.84 (m, 1H), 1.89-1.80 (m, 2H) (one exchangeable proton not observed). m/z: 437

Example 30
(2S)-N-{(1S)-1-Cyano-2-[4'-(methylsulfonyl)biphenyl-4-yl]ethyl}-1,4-oxazepane-2-carboxamide Prepared using Method B
Aryl iodide: Commercial
Intermediate: 6

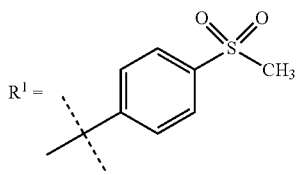

¹H NMR (400 MHz, CDCl₃): δ 8.02 (d, 2H), 7.77 (d, 2H), 7.61 (d, 2H), 7.44 (dd, 2H), 7.29-7.16 (m, 1H), 5.25-5.13 (m, 1H), 4.12-4.06 (m, 1H), 4.05-3.95 (m, 1H), 3.77 (dtd, 1H), 3.36-3.28 (m, 1H), 3.17 (t, 2H), 3.14-2.97 (m, 2H), 3.00-2.82 (m, 6H), 1.91-1.77 (m, 1H). m/z: 428

Example 31
(2S)-N-{(1S)-2-[4'-(Azetidin-1-ylsulfonyl)biphenyl-4-yl]-1-cyanoethyl}-1,4-oxazepane-2-carboxamide Prepared using Method B
Aryl iodide: Commercial
Intermediate: 6

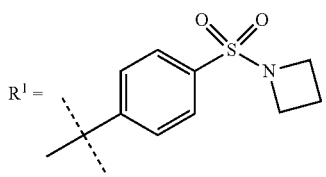

¹H NMR (400 MHz, CDCl₃): δ 7.92 (d, 2H), 7.77 (d, 2H), 7.66-7.56 (m, 2H), 7.44 (dd, 2H), 7.31-7.14 (m, 1H), 5.25-5.12 (m, 1H), 4.13-4.07 (m, 1H), 4.06-3.95 (m, 1H), 3.86-3.69 (m, 5H), 3.36-3.27 (m, 1H), 3.24-3.10 (m, 2H), 3.10-2.84 (m, 3H), 2.12 (m, 2H), 1.91-1.76 (m, 2H) (one exchangeable proton not observed). m/z: 469

Example 32
(2S)-N-[(1S)-1-Cyano-2-(4'-fluorobiphenyl-4-yl)ethyl]-1,4-oxazepane-2-carboxamide Prepared using Method A
Boronate ester: Commercial
Intermediate: 5

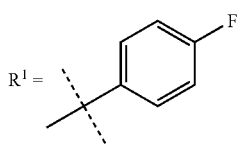

¹H NMR (400 MHz, CDCl₃): δ 7.56-7.51 (m, 4H), 7.38 (d, 2H), 7.21-7.08 (m, 3H), 5.20 (dt, 1H), 4.09 (dd, 1H), 3.98 (dt, 1H), 3.74 (ddd, 1H), 3.30 (dd, 1H), 3.13 (d, 2H), 3.03 (dd, 1H), 2.98-2.81 (m, 2H), 1.89-1.76 (m, 2H) (one exchangeable proton not observed). m/z: 368

Example 33
(2S)-N-{(1S)-2-[4-(1,3-Benzothiazol-5-yl)phenyl]-1-cyanoethyl}-1,4-oxazepane-2-carboxamide Prepared using Method A
Boronate ester: Commercial
Intermediate: 5

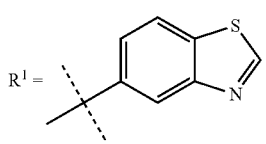

¹H NMR (400 MHz, DMSO-d₆): δ 9.43 (s, 1H), 8.61 (d, 1H), 8.33 (d, 1H), 8.23 (d, 1H), 7.82-7.72 (m, 3H), 7.41 (d, 2H), 5.08-4.98 (m, 1H), 3.98 (dd, 1H), 3.84 (ddd, 1H), 3.75-3.66 (m, 1H), 3.27-3.14 (m, 2H), 3.02 (dd, 1H), 2.78-2.69 (m, 1H), 2.64-2.51 (m, 3H), 1.79-1.64 (m, 2H). m/z: 407

Example 34

Diastereomeric mixture of (2S)—N-[(1S)-1-cyano-2-(4'-cyanobiphenyl-4-yl)ethyl]-1,4-oxazepane-2-carboxamide and (2R)—N-[(1S)-1-cyano-2-(4'-cyanobiphenyl-4-yl)ethyl]-1,4-oxazepane-2-carboxamide

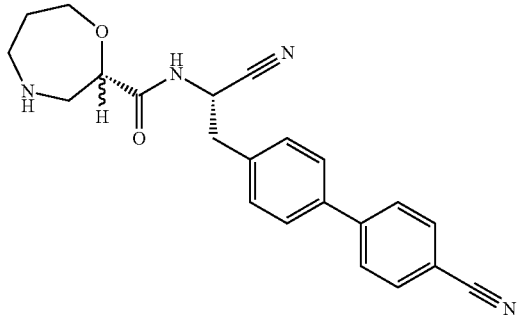

i) tert-Butyl 2-{[(1S)-1-cyano-2-(4'-cyanobiphenyl-4-yl)ethyl]carbamoyl}-1,4-oxazepane-4-carboxylate rac-4-(tert-Butoxycarbonyl)-1,4-oxazepane-2-carboxylic acid (248 mg, 1.01 mmol) and 4'-[(2S)-2-amino-2-cyanoethyl]biphenyl-4-carbonitrile (Intermediate 1, 1200 mg, 0.81 mmol) were added to T3P (700 mg, 50% solution in DMF) in DMF (2 mL). TEA (640 µL, 4.54 mmol) was added and the reaction stirred at rt for 18 h. After this time the reaction mixture was concentrated under reduced pressure. The resultant oil was dissolved in EtOAc and washed successively with 2 M aqueous hydrochloric acid, saturated aqueous solution of sodium hydrogen carbonate and sodium chloride solution. The organic extracts were dried (magnesium sulfate), filtered and concentrated under reduced pressure to afford the subtitled compound as a yellow oil which was used without further purification in the next step.

ii) Diastereomeric mixture of (2S)—N-[(1S)-1-cyano-2-(4'-cyanobiphenyl-4-yl)ethyl]-1,4-oxazepane-2-carboxamide and (2R)—N-[(1S)-1-cyano-2-(4'-cyanobiphenyl-4-yl)ethyl]-1,4-oxazepane-2-carboxamide Prepared according to procedure in Method A step ii) using tert-butyl 2-{[(1S)-1-cyano-2-(4'-cyanobiphenyl-4-yl)ethyl]carbamoyl}-1,4-oxazepane-4-carboxylate to afford the title compound as a white solid (150 mg, 50% over two steps). The isolated compound was a mixture of two diastereomers, which were not separated. $^1$H NMR (400 MHz, CDCl$_3$): δ 7.75-7.64 (m, 4H), 7.59 (dd, 2H), 7.43 (dd, 2H), 7.30-7.22 (m, 1H), 5.25-5.11 (m, 1H), 4.12-4.06 (m, 1H), 4.05-3.95 (m, 1H), 3.81-3.70 (m, 1H), 3.33 (ddd, 1H), 3.25-3.09 (m, 2H), 3.08-3.00 (m, 1H), 2.98-2.81 (m, 2H), 1.92-1.75 (m, 2H) (one exchangeable proton not observed).

LCMS (10 cm_ESCI_Formic_MeCN) $t_R$ 2.58 (min) m/z 375 (MH$^+$).

Example 35

(2S)—N-{(1S)-1-Cyano-2-[4-(4-methyl-3-oxo-1,2,3,4-tetrahydroquinoxalin-6-yl)phenyl]ethyl}-1,4-oxazepane-2-carboxamide

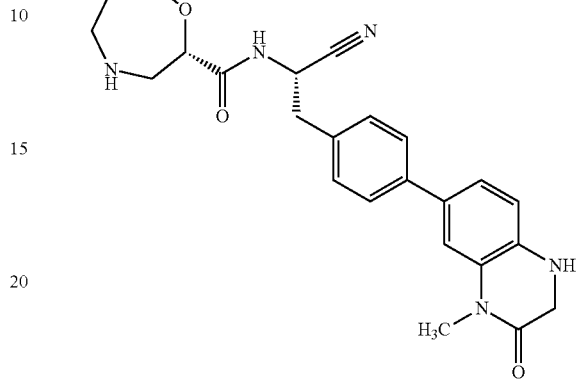

i) tert-Butyl (2S)-2-({(2S)-1-amino-3-[4-(4-methyl-3-oxo-1,2,3,4-tetrahydroquinoxalin-6-yl)phenyl]-1-oxopropan-2-yl}carbamoyl)-1,4-oxazepane-4-carboxylate 7-(5,5-Dimethyl-1,3,2-dioxaborinan-2-yl)-1-methylquinoxalin-2(1H)-one (Boronate ester 2, 100 mg, 0.37 mmol) and tert-butyl (2S)-2-{[(2S)-1-amino-3-(4-iodophenyl)-1-oxopropan-2-yl]carbamoyl}-1,4-oxazepane-4-carboxylate (Intermediate 4, 182 mg, 0.35 mmol) were dissolved in ACN (9 mL) and water (0.4 mL). The reaction mixture was degassed under nitrogen for 30 min before the addition of potassium carbonate (73 mg, 0.53 mmol) and Pd(dppf)Cl$_2$.DCM (29 mg, 0.035 mmol). The reaction mixture was heated at 80° C. for 1 h. After this time the reaction was concentrated under reduced pressure. Purified by silica gel column chromatography eluting with 8% methanol in EtOAc to afford the subtitled compound as a brown oil (192 mg, 100%). Used without further purification in the next step.

ii) tert-Butyl (2S)-2-({(1S)-1-cyano-2-[4-(4-methyl-3-oxo-1,2,3,4-tetrahydroquinoxalin-6-yl)phenyl]ethyl}carbamoyl)-1,4-oxazepane-4-carboxylate Burgess reagent (167 mg, 0.70 mmol) was added to a solution of tert-butyl (2S)-2-({(2S)-1-amino-3-[4-(4-methyl-3-oxo-1,2,3,4-tetrahydroquinoxalin-6-yl)phenyl]-1-oxopropan-2-yl}carbamoyl)-1,4-oxazepane-4-carboxylate (192 mg, 0.35 mmol) in DCM (15 mL). The reaction mixture was stirred at rt for 24 h. After which time the reaction was transferred to a separating funnel and washed with water. The organic extracts were dried (phase separator cartridge) and concentrated under reduced pressure. The resultant solid was purified by silica gel column chromatography eluting with 65% EtOAc in iso-hexane to afford a yellow oil. Trituration with diethyl ether afforded the subtitled compound as an oil (101 mg, 54%). 1H NMR (400 MHz, CDCl$_3$): δ 8.32 (s, 1H), 7.95 (d, 1H), 7.67 (d, 2H), 7.58 (dd, 1H), 7.49 (d, 1H), 7.43 (d, 2H), 7.10-7.03 (m, 1H), 5.25-5.12

(m, 1H), 4.23-4.10 (m, 3H), 3.77 (s, 3H), 3.54-3.49 (m, 3H), 3.28-3.19 (m, 3H), 2.05-1.89 (m, 2H), 1.47 (s, 9H).

iii) (2S)—N-{(1S)-1-Cyano-2-[4-(4-methyl-3-oxo-1,2,3,4-tetrahydroquinoxalin-6-yl)phenyl]ethyl}-1,4-oxazepane-2-carboxamide tert-Butyl (2S)-2-({(1S)-1-cyano-2-[4-(4-methyl-3-oxo-1,2,3,4-tetrahydroquinoxalin-6-yl)phenyl]ethyl}carbamoyl)-1,4-oxazepane-4-carboxylate (101 mg, 0.19 mmol) was dissolved in formic acid (2 mL) and heated at 50° C. for 10 min on a pre-heated stirrer hotplate. After this time the reaction was concentrated under reduced pressure, dissolved in DCM and washed with saturated sodium hydrogen carbonate solution. The organic extract was run through a hydrophobic frit/phase separator and concentrated under reduced pressure. The solid was purified by silica gel column chromatography eluting with 0-2% methanolic ammonia (7 N) in DCM to afford the title compound as a yellow solid (65 mg, 80%). $^1$H NMR (400 MHz, CDCl$_3$): δ 8.32 (s, 1H), 7.95 (d, 1H), 7.65 (d, 2H), 7.57 (dd, 1H), 7.47 (m, 3H), 7.21 (d, 1H), 5.22 (dt, 1H), 4.11 (dd, 1H), 4.00 (dt, 1H), 3.75 (m, 5H), 3.32 (dd, 1H), 3.17 (m, 2H), 3.06 (dd, 1H), 2.99-2.87 (m, 2H), 1.89-1.81 (m, 2H) (two exchangeable protons not observed). LCMS (10 cm_ESCI_Formic_MeCN) $t_R$ 2.38 (min) m/z 432 (MH-+).

Example 36

(2S)-2-[(3S,4E)-6-(2,3-Dihydro-1H-indol-1-yl)-6-oxohex-4-en-3-yl]-1,4-oxazepane-2-carboxamide trifluoroacetate

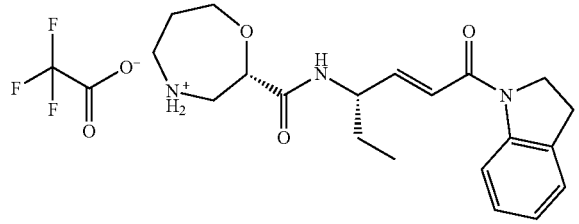 [SMILES: O=C([O-])C(F)(F)F ; CC[C@@H](/C=C/C(=O)N1CCc2ccccc21)NC(=O)[C@@H]1CNCCCO1]

i) tert-Butyl (2S)-2-{[(3S,4E)-6-(2,3-dihydro-1H-indol-1-yl)-6 oxohex-4-en-3-yl]carbamoyl}-1,4-oxazepane-4-carboxylate

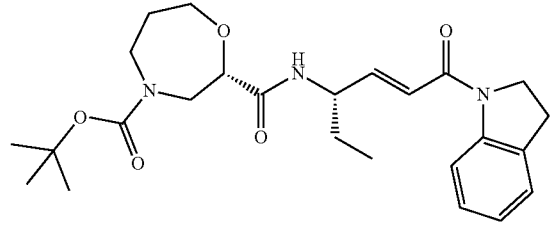 [SMILES: CC[C@@H](/C=C/C(=O)N1CCc2ccccc21)NC(=O)[C@@H]1CN(C(=O)OC(C)(C)C)CCCO1]

HATU (2.33 g, 6.12 mmol) was added to (2S)-4-(tert-butoxycarbonyl)-1,4-oxazepane-2-carboxylic acid (Intermediate 3, 1.25 g, 5.10 mmol), [(1S,2E)-4-(2,3-dihydro-1H-indol-1-yl)-1-ethyl-4-oxo-buten-1-yl]amine trifluoroacetate (Intermediate 6 in WO2012109415, 1.76 g, 5.10 mmol) and DiPEA (4.45 ml, 25.5 mmol) in DCM (25 ml) at rt. The resulting mixture was stirred at rt for 4 h. The reaction mixture was diluted with DCM (100 mL), and washed sequentially with 0.1 M aq. HCl (100 mL), saturated aq. NaHCO$_3$ (100 mL), and saturated brine (100 mL). The organic layer was dried over Na$_2$SO$_4$, filtered and evaporated to afford the sub-titled product (1.50 g, 64%). LC-MS m/z 358 (M-Boc+H$^+$). A sample of the crude product (190 mg, 0.42 mmol) was purified by preparative chiral-HPLC on a CHIRALPAK IC-3 column, eluting isocratically with 50% EtOH in hexane as eluent. Fractions containing the desired compound were evaporated to dryness to afford the sub-titled product (180 mg, 95%) as a colourless oil. LC-MS m/z 358 (M-Boc+H$^+$).

TFA (2 mL, 26.0 mmol) was added to tert-butyl (2S)-2-{[(3S,4E)-6-(2,3-dihydro-1H-indol-1-yl)-6-oxohex-4-en-3-yl]carbamoyl}-1,4-oxazepane-4-carboxylate (180 mg, 0.39 mmol) in DCM (10 mL) at rt. The resulting solution was stirred at rt for 4 h. The solvent was removed under reduced pressure. The crude product was purified by preparative Flash (C18 column), using decreasingly polar mixtures of water (containing 0.10% TFA) and MeCN as eluents. Fractions containing the desired compound were dried by lyophilization to afford the title product (100 mg, 54%) as a white solid. $^1$H NMR (300 MHz, DMSO-d$_6$): δ 8.80-9.10 (m, 2H), 8.30 (d, 1H), 8.15 (d, 1H), 7.10-7.30 (m, 2H), 6.95-7.10 (m, 1H), 6.70-6.85 (m, 1H), 6.45 (d, 1H), 4.10-4.70 (m, 4H), 3.90-4.10 (m, 1H), 3.75-3.85 (m, 1H), 3.55-3.70 (m, 1H), 3.05-3.40 (m, 5H), 1.90-2.10 (m, 2H), 1.50-1.75 (m, 2H), 0.85 (t, 3H). LCMS m/z 358 (MH$^+$).

Example 37

(2S)-2-[(2E,4S)-1-(2,3-Dihydro-1H-indol-1-yl)-6-methyl-1-oxohept-2-en-4-yl]-1,4-oxazepane-2-carboxamide trifluoroacetate

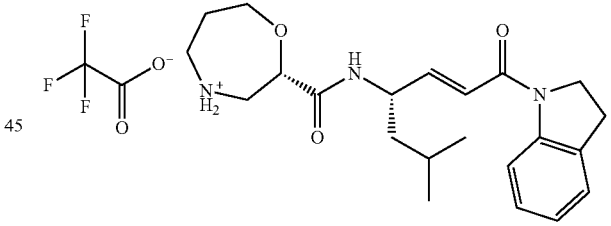

i) tert-Butyl (2S)-2-{[(2E,4S)-1-(2,3-dihydro-1H-indol-1-yl)-6-methyl-1-oxohept-2-en-4-yl]carbamoyl}-1,4-oxazepane-4-carboxylate

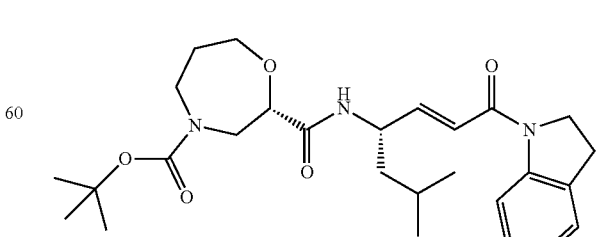

HATU (465 mg, 1.22 mmol) was added to (2S)-4-(tert-butoxycarbonyl)-1,4-oxazepane-2-carboxylic acid (Intermediate 3, 150 mg, 0.61 mmol), [(1S,2E)-4-(2,3-dihydro-1H-indol-1-yl)-1-(2-methylpropyl)-4-oxo-2-buten-1-yl]amine trifluoroacetate (Intermediate 13 in WO2012109415, 174 mg, 0.47 mmol) and DiPEA (0.427 mL, 2.45 mmol) in DMF (5.0 mL) at 0° C. The resulting solution was stirred at rt for 2.5 h. The reaction mixture was evaporated to dryness and redissolved in EtOAc (25 mL), and washed sequentially with saturated aq. NH$_4$Cl (4×20 mL), saturated brine (3×20 mL), and water (3×20 mL). The organic layer was dried over Na$_2$SO$_4$, filtered and evaporated to afford crude sub-titled product (200 mg, 67%) as a yellow oil. LC-MS m/z 486 (MH$^+$). The crude product was used without further purification in the next step.

TFA (0.635 mL, 8.24 mmol) was added to tert-butyl (2S)-2-{[(2E,4S)-1-(2,3-dihydro-1H-indol-1-yl)-6-methyl-1-oxohept-2-en-4-yl]carbamoyl}-1,4-oxazepane-4-carboxylate (200 mg, 0.41 mmol) in DCM (5.0 mL) at 0° C. The resulting solution was stirred at rt for 2 h. The solvent was removed under reduced pressure. The crude product was purified by preparative HPLC (Waters XBridge Prep C18 OBD column, 5p silica, 19 mm diameter, 150 mm length), using decreasingly polar mixtures of water (containing 0.5% TFA) and MeCN as eluents. Fractions containing the desired compound were evaporated to dryness to afford the title product (130 mg, 63%) as a yellow gum.

LC-MS m/z 386 (MH$^+$). 1H-NMR (300 MHz, CD$_3$OD): δ 8.15 (1H, d), 7.10-7.30 (2H, m), 7.05 (1H, t), 6.75-6.90 (1H, m), 6.50 (1H, d), 4.60-4.80 (1H, m), 4.40-4.55 (1H, m), 4.10-4.30 (3H, m), 3.70-3.95 (2H, m), 3.15-3.50 (5H, m), 2.05-2.25 (2H, m), 1.40-1.70 (3H, m), 0.95 (6H, t), 1.35 (1H, d) (two exchangeable protons not observed).

Pharmacological Activity

Test A1: Fluorescence Assay for Recombinant Human (RH) DPP1

The activity of DPP1 was determined by measuring the enzymatic release of aminomethyl coumarin (AMC) from the peptide substrate (H-Gly-Arg-AMC), which leads to an increase in fluorescence intensity at λex=350 nm and λem=450 nm. The assay was carried out in black 384 well plates in a final volume of 50 µl at 22° C. The assay conditions contained the following: 25 mM piperazine buffer pH 5.0; 50 mM NaCl, 5 mM DTT; 0.01% (v/v) Triton X-100; 100 µM H-Gly-Arg-AMC and rhDPP1 (~50 pM). Potential inhibitors were made up in DMSO and then diluted in the assay to give a final concentration of not exceeding 1% (v/v) DMSO. A 10-point half-log dilution series of the inhibitors (highest concentration typically 10 µM) was tested and the pIC$_{50}$ determined using a 4-parameter logistic equation in a non-linear curve fitting routine. A standard DPP1 inhibitor, 4-amino-N-[(1S)-1-cyano-2-(4'-cyanobiphenyl-4-yl)ethyl]tetrahydro-2H-pyran-4-carboxamide (WO2010/128324, Ex. 3) was used as a positive control in the assay. Routinely, inhibitors were pre-incubated with rhDPP1 for 30-60 min prior to the addition of the peptide substrate to start the reaction for a further 60 min at 22° C. After that the plates were immediately read in a fluorescence plate reader using the above emission and excitation wavelengths [modified from Kam, C M, Gotz, M G, Koot, G, McGuire, M J, Thiele, D L, Hudig, D & Powers, J C (2004). Arch Biochem Biophys, 427, 123-134 & McGuire, M J, Lipsky, P E & Thiele, D L (1992). Arch Biochem Biophys, 295, 280-288]. The results obtained are shown in Table 11 below (Examples 1-35).

Test A2: Fluorescence Assay for Recombinant Human (RH) DPP1

The activity of DPP1 was determined by measuring the enzymatic release of aminomethyl coumarin (AMC) from the peptide substrate (H-Gly-Arg-AMC), which leads to an increase in fluorescence intensity at λex=350 nm and λem=450 nm. The assay was carried out in black 384 well plates in a final volume of 10 µl at rt. The assay conditions contained the following: 25 mM piperazine buffer pH 5.0; 50 mM NaCl, 5 mM DTT; 0.005 (v/v) Triton X-100; 50 µM H-Gly-Arg-AMC and 96.4 pM rhDPP1—Potential inhibitors were diluted in DMSO to generate 100× of the final assay concentration. The compounds were tested at 10 concentrations with half-log dilution steps (highest concentration typically 1 µM) and with a final DMSO concentration of 1% (v/v). Routinely, inhibitors were pre-incubated with rhDPP1 for 30 min prior to the addition of the peptide substrate to start the reaction for a further 30 min. After incubation the plates were read in a fluorescence plate reader using the above emission and excitation wavelengths. The pIC$_{50}$ were determined using a 4-parameter logistic equation in a non-linear curve fitting routine (Smartfit, Genedata Screener®). A standard DPP1 inhibitor, 4-amino-N-[(1S)-1-cyano-2-(4'-cyanobiphenyl-4-yl)ethyl]tetrahydro-2H-pyran-4-carboxamide (WO2010/128324, Ex. 3) was used as a positive control and 1% (v/v) DMSO was used as a negative control in the assay. [modified from Kam, C M, Gotz, M G, Koot, G, McGuire, M J, Thiele, D L, Hudig, D & Powers, J C (2004). Arch Biochem Biophys, 427, 123-134 & McGuire, M J, Lipsky, P E & Thiele, D L (1992). Arch Biochem Biophys, 295, 280-288]. The results obtained are shown in Table 11 below (Examples 36-37).

TABLE 11

| Compound of Example | DPP1 activity, pIC$_{50}$ |
| --- | --- |
| 1 | 7.45 |
| 2 | 8.35 |
| 3 | 7.99 |
| 4 | 7.1 |
| 5 | 7.79 |
| 6 | 7.44 |
| 7 | 7.16 |
| 8 | 7.06 |
| 9 | 7.89 |
| 10 | 7.67 |
| 11 | 7.05 |
| 12 | 8.0 |
| 13 | 8.14 |
| 14 | 7.78 |
| 15 | 8.29 |
| 16 | 8.24 |
| 17 | 8.2 |
| 18 | 8.5 |
| 19 | 7.84 |
| 20 | 7.9 |
| 21 | 8.09 |
| 22 | 7.71 |
| 23 | 7.17 |
| 24 | 7.86 |
| 25 | 7.97 |
| 26 | 7.87 |
| 27 | 8.18 |
| 28 | 8.09 |
| 29 | 8.62 |
| 30 | 7.43 |
| 31 | 7.67 |
| 32 | 7.37 |
| 33 | 7.21 |
| 34 | 7.22 |
| 35 | 7.61 |
| 36 | 8.3 |
| 37 | 8.28 |

Aortic Binding

A number of compounds have been described in literature to be retained selectively in the aorta in quantitative whole-body autoradiography (QWBA) studies, leading to concomitant ultra-structural changes when examined by electron microscopy (see e.g. muzolimine (Schmidt et al. 1984, Biochem. Pharmacol., 33, 1915-1921)). Further, the α-amino amide nitrile 4-amino-N-[(1S)-1-cyano-2-(4'-cyanobiphenyl-4-yl)ethyl]tetrahydro-2H-pyran-4-carboxamide, disclosed as a DPP1 inhibitor (WO2010/128324, Ex. 3), showed a high level of aortic retention in rat QWBA studies. To assist the design of DPP1 inhibitors with a decreased risk of binding to elastin rich tissues, such as the aorta, the in-vitro competitive aortic binding assay disclosed below (Test B) was developed to facilitate the selection process. Reference compounds and selected compounds representing the present disclosure were tested in Test B and the results obtained are shown in Table 12.

Test B: In-Vitro Competitive Aortic Tissue Binding Assay

Aortic homogenate was prepared from the thoracic aortae of Han Wistar rats. Freshly isolated thoracic aortae were frozen, and later thawed and stripped of non-elastic material. Stripped aortae were then weighed, cut into small pieces and homogenised first with a rotor-stator homogeniser; and then with a loose-fit, and then a tight-fit, Dounce homogeniser in Puck's saline (137 mM NaCl, 5.37 mM KCl, 4.17 mM $NaHCO_3$, and 5.55 mM D-glucose). Homogenate concentration was adjusted to 30 mg/mL in Puck's saline, and aliquots were stored at −80° C. until use. Positive and negative control compounds and test compounds were made up to 100 mM in DMSO, and added to 1 mL aliquots of aortic homogenate in Puck's saline for a final concentration of 100 μM. Homogenate samples were pre-incubated with test compounds at 37° C., rotating, overnight. [$^{14}C$]4-Amino-N-[(1S)-1-cyano-2-(4'-cyanobiphenyl-4-yl)ethyl]tetrahydro-2H-pyran-4-carboxamide was then added to all samples to a final concentration of 100 μM, and samples were incubated at 37° C., rotating, for a further 2 h. Protein was precipitated from each sample by the addition of 10 mL acetone, pre-chilled to −20° C. Samples were left overnight at −20° C. to allow complete precipitation. Precipitate was pelleted by centrifugation at 4,500×g at 4° C. for 20 min, an aliquot of supernatant was removed for analysis, and the remainder of the supernatant discarded. Precipitate was washed by resuspension in 10 mL 80% methanol in distilled water, and re-pelleted by centrifugation at 4,500×g at 4° C. for 20 min. Washing was repeated for a total of 4 washes in 80% methanol, and 2 further washes in 100% methanol, an aliquot of supernatant being removed for analysis at each stage. After final wash, precipitate was air-dried, and dissolved overnight in 1 mL NCSII Tissue Solubiliser. 1 mL aliquots of supernatants were added to 5 mL Ultima Gold scintillation fluid (Perkin Elmer, MA, U.S.A.), and 1 mL solubilised pellets were added to 5 mL Hionic-Fluor scintillation fluid (Perkin Elmer, MA, U.S.A.). Radioactivity of samples was determined on a Beckman LS6500 multipurpose scintillation counter (Beckman Coulter, IN, U.S.A.). On each occasion, 4-amino-N-[(1S)-1-cyano-2-(4'-cyanobiphenyl-4-yl)ethyl]tetrahydro-2H-pyran-4-carboxamide was run as a positive control, and N-(1-{(3R)-3-(3,5-difluorophenyl)-3-[1-(methylsulfonyl)piperidin-4-yl]propyl}piperidin-4-yl)-N-ethyl-2-[4-(methylsulfonyl)phenyl]acetamide (compound 1, WO2006/001751) and DMSO vehicle were run as negative controls. Duplicate samples were tested for each compound on each experimental occasion, and at least two experiments were run for each test compound. Mean radioactivity of the samples pre-incubated with DMSO vehicle control was taken to be 100% binding, and results for samples pre-incubated with other compounds were expressed as % difference from vehicle control. 1-way ANOVA and Bonferroni's multiple comparison tests were performed to calculate significance of differences from vehicle control.

The results obtained are shown in Table 12 below. The results are quantified into four different categories: strong binder, medium binder, binder and no binder.

TABLE 12

| Compound | Structure | Aortic Tissue Binding |
|---|---|---|
| WO2010/128324 (Ex. 3) | [chemical structure] | Strong binder (reference) |

TABLE 12-continued

| Compound | Structure | Aortic Tissue Binding |
| --- | --- | --- |
| WO2010/128324 (Example 17) | 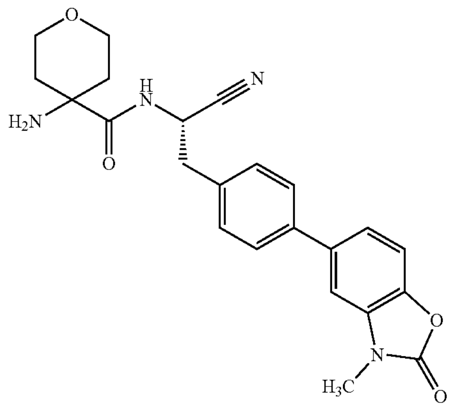 [SMILES: Cn1c(=O)oc2ccc(-c3ccc(C[C@@H](C#N)NC(=O)C4(N)CCOCC4)cc3)cc21] | Strong binder |
| WO2009/074829 (Example 96) | 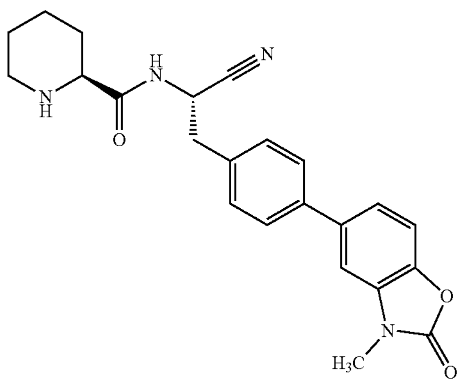 [SMILES: Cn1c(=O)oc2ccc(-c3ccc(C[C@@H](C#N)NC(=O)[C@@H]4CCCCN4)cc3)cc21] | Medium binder |
| WO2009/074829 (Example 24) | 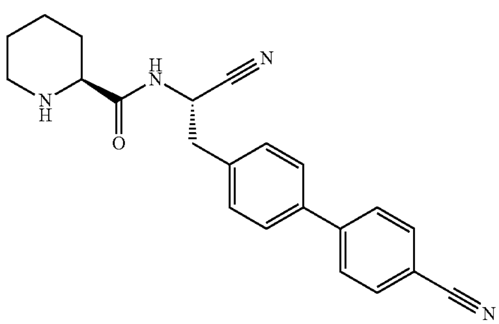 [SMILES: N#Cc1ccc(-c2ccc(C[C@@H](C#N)NC(=O)[C@@H]3CCCCN3)cc2)cc1] | Binder |
| Example 2 | 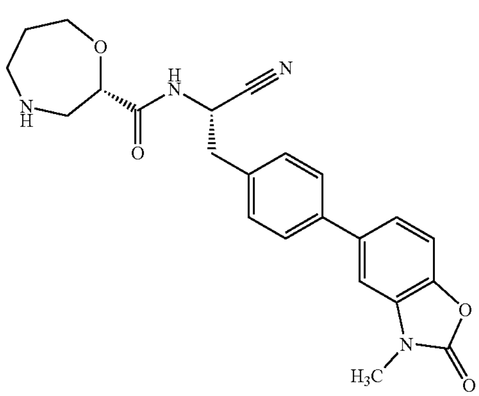 [SMILES: Cn1c(=O)oc2ccc(-c3ccc(C[C@@H](C#N)NC(=O)[C@@H]4CNCCCO4)cc3)cc21] | No binder |

TABLE 12-continued

| Compound | Structure | Aortic Tissue Binding |
|---|---|---|
| Example 16 | 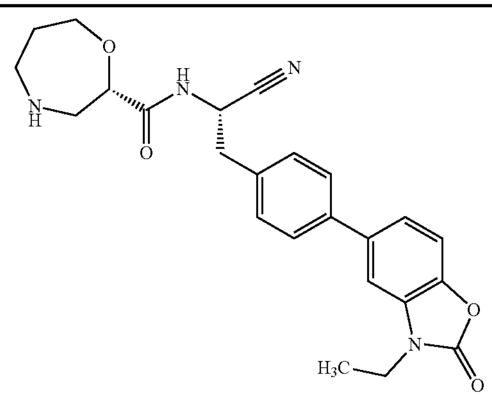 | No binder |

[$^{14}$C] 4-Amino-N-[(1S)-1-cyano-2-(4'-cyanobiphenyl-4-yl)ethyl]tetrahydro-2H-pyran-4-carboxamide

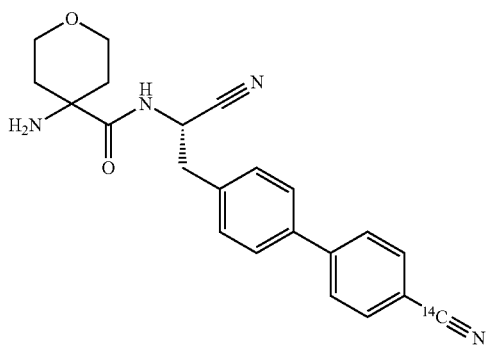 [SMILES: N#C[C@H](Cc1ccc(-c2ccc([14C]#N)cc2)cc1)NC(=O)C1(N)CCOCC1]

i) 4-Bromobenzo-[$^{14}$C]-nitrile

1-Bromo-4-iodobenzene (473 mg, 1.67 mmol) and copper (I)[$^{14}$C]cyanide (1850 MBq, 77 mg, 0.84 mmol) were dissolved in 1-methylpyrrolidin-2-one (4 mL) and heated in the microwave for 3 h at 150° C. The reaction was diluted with EtOAc (150 ml) and washed with 2% aq ferric chloride (100 ml), 2% w/v aq sodium thiosulphate (100 ml) and saturated brine (25 mL×3). The organics were passed through a phase separator and the solvent removed to afford the crude product. The crude material was purified by silica gel column chromatography eluting with 2% EtOAc in isoheptane to afford the title compound as a white solid (442 MBq, 37 mg, 24%).

ii) (S)-tert-Butyl 4-(1-amino-3-(4'-[$^{14}$C]-cyanobiphenyl-4-yl)-1-oxopropan-2-ylcarbamoyl)tetrahydro-2H-pyran-4-ylcarbamate (S)-tert-Butyl-4-(1-amino-1-oxo-3-(4-(4,4,5,5-tetramethyl-1,3,2-dioxaborolan-2-yl)phenyl)propan-2-ylcarbamoyl)tetrahydro-2H-pyran-4-ylcarbamate (243 mg, 0.47 mmol), Pd-118 (30.6 mg, 0.05 mmol) and potassium carbonate (195 mg, 1.41 mmol) were added to a flask under an atmosphere of nitrogen. 4-Bromobenzo-[$^{14}$C]-nitrile (973 MBq, 86 mg, 0.47 mmol) in degassed ACN (6 mL) was added to the reaction flask, followed by water (3 mL). The mixture was heated at 73° C. under nitrogen for 4 h and allowed to stand overnight at rt. The reaction was diluted with water (50 ml) and the product extracted into DCM (25 mL×4). The combined organics were washed with saturated brine (50 ml) and the organic portion passed through a phase separator containing magnesium sulphate. The organics were concentrated in vacuo to give a dark brown oil. The crude material was purified by silica gel column chromatography eluting with 0-100% EtOAc in heptane to afford a gum which on tituration with ether/heptane gave the title compound as an off-white solid (802 MBq, 189 mg, 82%). m/z (ES+) 395 [M+2H-BOC]$^+$ iii) (S)-tert-Butyl 4-(1-cyano-2-(4'-[$^{14}$C]-cyanobiphenyl-4-yl)ethylcarbamoyl)tetrahydro-2H-pyran-4-ylcarbamate (S)-tert-Butyl 4-(1-amino-3-(4'-[$^{14}$C]-cyanobiphenyl-4-yl)-1-oxopropan-2-ylcarbamoyl)tetrahydro-2H-pyran-4-ylcarbamate (802 MBq, 189 mg, 0.38 mmol) was dissolved in DCM (4 mL) and stirred under nitrogen at rt. Burgess reagent (137 mg, 0.57 mmol) was added and the reaction was allowed to stir for 6.5 h. The crude mixture was purified by silica gel column chromatography eluting with 25-100% EtOAc in heptane to give the title compound as a white solid (714 MBq, 164 mg, 90%). $^1$H NMR (500 MHz, DMSO-d$_6$): δ 1.38 (s, 9H), 1.55-1.77 (m, 2H), 1.84-2.02 (m, 1H), 3.07-3.25 (m, 3H), 3.43-3.53 (m, 1H), 3.54-3.62 (m, 1H), 5.04-5.13 (m, 1H), 7.04 (s, 1H), 7.43 (d, 2H), 7.71 (d, 2H), 7.87 (d, 2H), 7.93 (d, 2H), 8.46 (s, 1H). m/z (ES−) 475 [M−H]$^−$ iv) (S)-4-Amino-N-(1-cyano-2-(4'-[$^{14}$C]-cyanobiphenyl-4-yl)ethyl)tetrahydro-2H-pyran-4-carboxamide (S)-tert-Butyl 4-(1-cyano-2-(4'-[$^{14}$C]-cyanobiphenyl-4-yl)ethylcarbamoyl)tetrahydro-2H-pyran-4-ylcarbamate (133 MBq, 29 mg, 0.06 mmol) was added to a preheated solution of formic acid (500 μl, 13.04 mmol, 50° C.) and the reaction heated with stirring for 15 min at 50° C. The reaction was rapidly cooled and added to a cooled mixture of saturated sodium hydrogen carbonate (5 ml) and DCM (5 ml). The aqueous portion was washed with two further aliquots of DCM (5 ml) and the combined organics washed with water (10 ml) and dried over sodium sulphate. The organics were removed to give a colourless oil, which on tituration with ether gave a white solid. The crude mixture was purified by silica gel column chromatography eluting with 0-2% methanol in DCM to give the title compound (93 MBq, 68%) which was stored as an MeCN solution. $^1$H NMR (500 MHz, DMSO-$d_6$): δ 1.12 (d, 1H), 1.20 (d, 1H), 1.73 (ddd, 1H), 1.89 (ddd, 1H), 3.18-3.25 (m, 2H), 3.45 (dt, 1H), 3.53-3.66 (m, 3H), 5.02 (t, 1H), 7.43 (d, 2H), 7.71 (d, 2H), 7.89 (dd, 4H). m/z (ES+) 377 [M+H]$^+$

The invention claimed is:

1. Crystal form B of (2S)-N-{(1S)-1-cyano-2-[4-(3-methyl-2-oxo-2,3-dihydro-1,3-benzoxazol-5-yl)phenyl]ethyl}-1,4-oxazepane-2-carboxamide:

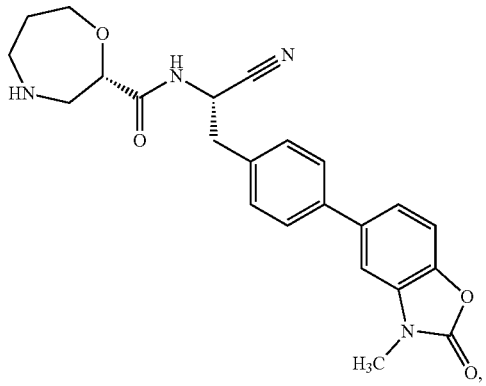 [SMILES: Cn1c(=O)oc2ccc(-c3ccc(C[C@@H](C#N)NC(=O)[C@@H]4CNCCCO4)cc3)cc21]

having X-ray powder diffraction peaks (° 2Θ) at 12.3±0.1, 14.3±0.1, 15.6±0.1, 16.3±0.1, and 17.2±0.1.

2. The crystal form B of (2S)-N-{(1S)-1-cyano-2-[4-(3-methyl-2-oxo-2,3-dihydro-1,3-benzoxazol-5-yl)phenyl]ethyl}-1,4-oxazepane-2-carboxamide of claim 1, having X-ray powder diffraction peaks (° 2Θ) at 18.3±0.1, 18.5±0.1, 19.7±0.1, 21.2±0.1, and 23.6±0.1.

3. A pharmaceutical composition comprising the crystal form B of (2S)-N-{(1S)-1-cyano-2-[4-(3-methyl-2-oxo-2,3-dihydro-1,3-benzoxazol-5-yl)phenyl]ethyl}-1,4-oxazepane-2-carboxamide of claim 1, and a pharmaceutically acceptable adjuvant, diluent or carrier.

4. A pharmaceutical composition comprising the crystal form B of (2S)-N-{(1S)-1-cyano-2-[4-(3-methyl-2-oxo-2,3-dihydro-1,3-benzoxazol-5-yl)phenyl]ethyl}-1,4-oxazepane-2-carboxamide of claim 2, and a pharmaceutically acceptable adjuvant, diluent or carrier.

5. A method for treating an obstructive disease of the airway, comprising orally administering to a patient in need thereof, the pharmaceutical composition of claim 3.

6. A method for treating an obstructive disease of the airway, comprising orally administering to a patient in need thereof, the pharmaceutical composition of claim 4.

7. The method of claim 5, wherein the obstructive disease of the airway is bronchiectasis.

8. The method of claim 5, wherein the obstructive disease of the airway is cystic fibrosis.

9. The method of claim 5, wherein the obstructive disease of the airway is asthma.

10. The method of claim 5, wherein the obstructive disease of the airway is chronic obstructive pulmonary disease (COPD).

11. The method of claim 6, wherein the obstructive disease of the airway is bronchiectasis.

12. The method of claim 6, wherein the obstructive disease of the airway is cystic fibrosis.

13. The method of claim 6, wherein the obstructive disease of the airway is asthma.

14. The method of claim 6, wherein the obstructive disease of the airway is chronic obstructive pulmonary disease (COPD).

* * * * *